US007567695B2

(12) United States Patent
Frost et al.

(10) Patent No.: US 7,567,695 B2
(45) Date of Patent: Jul. 28, 2009

(54) METHOD AND APPARATUS FOR READING REPORTER LABELED BEADS

(75) Inventors: Keith L. Frost, Seattle, WA (US); David A. Basiji, Seattle, WA (US); Richard A. Bauer, Kirkland, WA (US); Rosalynde J. Finch, Seattle, WA (US); William E. Ortyn, Bainbridge Island, WA (US); David J. Perry, Woodinville, WA (US)

(73) Assignee: Amnis Corporation, Seattle, WA (US)

( * ) Notice: Subject to any disclaimer, the term of this patent is extended or adjusted under 35 U.S.C. 154(b) by 992 days.

(21) Appl. No.: 11/078,009

(22) Filed: Mar. 11, 2005

(65) Prior Publication Data

US 2006/0029267 A1    Feb. 9, 2006

Related U.S. Application Data

(62) Division of application No. 09/976,237, filed on Oct. 12, 2001, now Pat. No. 6,934,408.

(60) Provisional application No. 60/240,125, filed on Oct. 12, 2000, provisional application No. 60/242,734, filed on Oct. 23, 2000.

(51) Int. Cl.
  *G06K 9/00* (2006.01)
(52) U.S. Cl. ..................... 382/129; 382/128
(58) Field of Classification Search ................. 382/129, 382/173; 356/39, 300; 250/591
See application file for complete search history.

(56) References Cited

U.S. PATENT DOCUMENTS 3,922,069 A  11/1975  Kishikawa et al. .......... 359/633

| 4,635,293 A | 1/1987 | Watanabe .................... 382/130 |
| 4,677,680 A | 6/1987 | Harima et al. ............... 382/112 |
| 4,770,992 A | 9/1988 | Van den Engh et al. ......... 435/6 |
| 4,777,525 A | 10/1988 | Preston, Jr. .................. 348/111 |

(Continued)

FOREIGN PATENT DOCUMENTS

WO     WO 98/53093     11/1998

(Continued)

OTHER PUBLICATIONS

Hecht, Eugene. "Optics $4^{th}$ ed." 2002. Addison-Wesley Longman, Inc., XP-002465391. ISBN: 0-8053-8566-5.

(Continued)

*Primary Examiner*—Duy M Dang
(74) *Attorney, Agent, or Firm*—Ronald M. Anderson

(57) ABSTRACT

Combinatorially-synthesized deoxyribonucleic acid (DNA) oligonucleotides attached to encoded beads that are hybridized to amplified and labeled genomic DNA or ribonucleic acid (RNA) are analyzed using a flow imaging system. Oligonucleotides and corresponding reporters are bound to the surfaces of a plurality of small beads such that different beads bear different oligo sequences. Each bead bears a unique optical signature comprising a predefined number of unique reporters, where each reporter comprises a predefined combination of different fluorochromes. The composite spectral signature in turn identifies the unique nucleotide sequence of its attached oligo chains. This optical signature is rapidly decoded using an imaging system to discriminate the different reporters attached to each bead in a flow in regard to color and spatial position on the bead.

28 Claims, 28 Drawing Sheets

U.S. PATENT DOCUMENTS

| | | | | |
|---|---|---|---|---|
| 4,786,165 | A | 11/1988 | Yamamoto et al. | 356/23 |
| 5,096,807 | A | 3/1992 | Leaback | 435/6 |
| 5,141,609 | A | 8/1992 | Sweedler et al. | 356/344 |
| 5,153,916 | A | 10/1992 | Inagaki et al. | 382/151 |
| 5,159,397 | A | 10/1992 | Kosaka et al. | 356/73 |
| 5,159,398 | A | 10/1992 | Maekawa et al. | 356/73 |
| 5,159,642 | A | 10/1992 | Kosaka | 382/6 |
| 5,247,339 | A | 9/1993 | Ogino | 356/73 |
| 5,272,354 | A | 12/1993 | Kosaka | 250/574 |
| 5,351,311 | A | 9/1994 | Rogers | 382/156 |
| 5,422,712 | A | 6/1995 | Ogino | 356/73 |
| 5,444,527 | A | 8/1995 | Kosaka | 356/73 |
| 5,471,294 | A | 11/1995 | Ogino | 356/73 |
| 5,548,349 | A | 8/1996 | Mizuguchi et al. | 348/766 |
| 5,548,395 | A | 8/1996 | Kosaka | 356/73 |
| 5,568,315 | A | 10/1996 | Shuman | 359/487 |
| 5,596,401 | A | 1/1997 | Kusuzawa | 356/23 |
| 5,621,460 | A | 4/1997 | Hatlestad et al. | 348/265 |
| 5,633,503 | A | 5/1997 | Kosaka | 250/458.1 |
| 5,644,388 | A | 7/1997 | Maekawa et al. | 356/73 |
| 5,674,743 | A | 10/1997 | Ulmer | 435/287.2 |
| 5,695,934 | A | 12/1997 | Brenner | 435/6 |
| 5,754,291 | A | 5/1998 | Kain | 356/338 |
| 5,760,899 | A | 6/1998 | Eismann | 356/326 |
| RE35,868 | E | 8/1998 | Kosaka | 250/574 |
| 5,831,723 | A | 11/1998 | Kubota et al. | 356/73 |
| 5,848,123 | A | 12/1998 | Strommer | 378/98.8 |
| 5,855,753 | A | 1/1999 | Trau et al. | 204/484 |
| 5,900,942 | A | 5/1999 | Spiering | 356/400 |
| 5,929,986 | A | 7/1999 | Slater et al. | 356/326 |
| 5,959,953 | A | 9/1999 | Alon | 369/44.41 |
| 6,007,994 | A | 12/1999 | Ward et al. | 435/6 |
| 6,013,445 | A | 1/2000 | Albrecht et al. | 435/6 |
| 6,014,468 | A | 1/2000 | McCarthy et al. | 382/254 |
| 6,066,459 | A | 5/2000 | Garini et al. | 435/6 |
| 6,116,739 | A | 9/2000 | Ishihara et al. | 353/31 |
| 6,156,465 | A | 12/2000 | Cao et al. | 430/30 |
| 6,210,973 | B1 | 4/2001 | Pettit | 436/172 |
| 6,211,955 | B1 | 4/2001 | Basiji et al. | 356/326 |
| 6,249,341 | B1 | 6/2001 | Basiji et al. | 356/73 |
| 6,256,096 | B1 | 7/2001 | Johnson | 356/335 |
| 6,330,081 | B1 | 12/2001 | Scholten | 358/463 |
| 6,330,361 | B1 | 12/2001 | Mitchell et al. | 382/211 |
| 6,381,363 | B1 | 4/2002 | Murching et al. | 382/164 |
| 6,522,781 | B1 | 2/2003 | Norikane et al. | 382/203 |
| 6,549,664 | B1 | 4/2003 | Daiber et al. | 382/232 |
| 6,743,581 | B1 | 6/2004 | Vo-Dinh | 435/6 |
| 6,763,149 | B2 | 7/2004 | Riley et al. | 382/294 |
| 7,006,710 | B2 | 2/2006 | Riley et al. | 382/294 |
| 2001/0006416 | A1 | 7/2001 | Johnson | 356/73 |
| 2002/0090613 | A1 | 7/2002 | Seul et al. | 435/6 |
| 2002/0119470 | A1 | 8/2002 | Nerenberg et al. | 435/6 |
| 2002/0126275 | A1 | 9/2002 | Johnson | 356/317 |
| 2002/0192717 | A1 | 12/2002 | Kantor et al. | 435/7.2 |
| 2003/0016897 | A1 | 1/2003 | Walt et al. | 385/12 |
| 2003/0020908 | A1 | 1/2003 | Frost et al. | 356/317 |
| 2003/0027126 | A1 | 2/2003 | Walt et al. | 435/4 |
| 2003/0086608 | A1 | 5/2003 | Frost et al. | 382/173 |
| 2003/0134330 | A1 | 7/2003 | Ravkin et al. | 435/7.1 |
| 2003/0165951 | A1 | 9/2003 | Bruchez et al. | 435/6 |
| 2004/0021078 | A1 | 2/2004 | Hagler | 250/339.13 |

FOREIGN PATENT DOCUMENTS

| | | |
|---|---|---|
| WO | WO 98/53300 | 11/1998 |
| WO | WO 99/24458 | 5/1999 |
| WO | WO 00/14545 | 3/2000 |
| WO | WO 00/42412 | 7/2000 |
| WO | WO 01/46675 | 6/2001 |

OTHER PUBLICATIONS

Kubota, Fumio et al. 1995. "Flow Cytometer and Imaging Device Used in Combination." *Cytometry*: 21:129-132.

Kubota, F. 2003. "Analysis of red cell and platelet morphology using an imaging-combined flow cytometer." *Clin. Lab. Haem.*: 25:71-76.

Ong, S.H. and P.M. Nickolls. 1991. "Optical Design in a Flow System For Imagina Cells." *Sciences in Medicine*: 14:2:74-80.

Ong, S.H. and P.M. Nickolls. 1994. "Analysis of MTF Degradation in the Imaging of Cells in a Flow System." *International Journal of Imaging Systems & Technology*: 5:243-250.

Ong, S.-H.; Horne, D.; Yeung, C.-K.; Nickolls, P.; Cole, T. "Development of an Image Flow Cytometer." Analytical and Quantitative Cytology and Histology. XIVth International Conference on Medical and Biological Engineering and the VIIth International Conference on Medical Physics, Espoo, Finland. Aug. 11-15, 1985. pp. 375-382.

Ong, Sim Heng. "Development of a System for Imaging and Classifying Biological Cells in a Flow Cytometer." Doctor of Philosophy Thesis. University of Sydney, School of Electrical Engineering. Aug. 1985.

Satoh, Kaneo et al. 2002. "Small Aggregates of Platelets Can Be Detected Sensitively by a Flow Cytometer Equipped With an Imaging Device: Mechanisms of Epinephrine-Induced Aggregation and Antiplatelet Effects of Beraprost." *Cytometry*: 48:194-201.

Wang, Fu-sheng and Fumio Kubota. 2002. "A Novel Apoptosis Research Method With Imaging-Combined Flow Cytometer and HITC OR IR-125 Staining." *Cytometry*: 50:267-274.

Wietzorrek, Joachim et al. 1999. "A New Multiparameter Flow Cytometer: Optical and Electrical Cell Analysis in Combination With Video Microscopy in Flow." *Cytometry*: 35:291-301.

*1ST POSITION*

*2ND POSITION*

*3RD POSITION*

*4TH POSITION*

*REPORTER LEGEND*

SEQUENCE LISTING

```
<160> NUMBER OF SEQ ID NOS: 44

<210> SEQ ID NO 1
<211> LENGTH: 30
<212> TYPE: DNA
<213> ORGANISM: Artificial Sequence
<220> FEATURE:
<223> OTHER INFORMATION: Exemplary Sequence intended to illustrate how
      inventive reporter labeled beads can be used

<400> SEQUENCE: 1
atcgaaatcg aatagtgcca taatttagct                                    30
```

```
<210> SEQ ID NO 2
<211> LENGTH: 10
<212> TYPE: DNA
<213> ORGANISM: Artificial Sequence
<220> FEATURE:
<223> OTHER INFORMATION: Exemplary Sequence intended to illustrate how
      inventive reporter labeled beads can be used

<400> SEQUENCE: 2
tagctttagc                                                          10

<210> SEQ ID NO 3
<211> LENGTH: 10
<212> TYPE: DNA
<213> ORGANISM: Artificial Sequence
<220> FEATURE:
<223> OTHER INFORMATION: Exemplary Sequence intended to illustrate how
      inventive reporter labeled beads can be used

<400> SEQUENCE: 3
agctttagct                                                          10

<210> SEQ ID NO 4
<211> LENGTH: 10
<212> TYPE: DNA
<213> ORGANISM: Artificial Sequence
<220> FEATURE:
<223> OTHER INFORMATION: Exemplary Sequence intended to illustrate how
      inventive reporter labeled beads can be used

<400> SEQUENCE: 4
gctttagctt                                                          10

<210> SEQ ID NO 5
<211> LENGTH: 10
<212> TYPE: DNA
<213> ORGANISM: Artificial Sequence
<220> FEATURE:
<223> OTHER INFORMATION: Exemplary Sequence intended to illustrate how
      inventive reporter labeled beads can be used

<400> SEQUENCE: 5
ctttagctta                                                          10

<210> SEQ ID NO 6
<211> LENGTH: 10
<212> TYPE: DNA
<213> ORGANISM: Artificial Sequence
<220> FEATURE:
<223> OTHER INFORMATION: Exemplary Sequence intended to illustrate how
      inventive reporter labeled beads can be used

<400> SEQUENCE: 6
tttagcttat                                                          10

<210> SEQ ID NO 7
<211> LENGTH: 10
<212> TYPE: DNA
<213> ORGANISM: Artificial Sequence
<220> FEATURE:
<223> OTHER INFORMATION: Exemplary Sequence intended to illustrate how
      inventive reporter labeled beads can be used

<400> SEQUENCE: 7
ttagcttatc                                                          10
```

```
<210> SEQ ID NO 8
<211> LENGTH: 10
<212> TYPE: DNA
<213> ORGANISM: Artificial Sequence
<220> FEATURE:
<223> OTHER INFORMATION: Exemplary Sequence intended to illustrate how
      inventive reporter labeled beads can be used

<400> SEQUENCE: 8
tagcttatca                                                            10

<210> SEQ ID NO 9
<211> LENGTH: 10
<212> TYPE: DNA
<213> ORGANISM: Artificial Sequence
<220> FEATURE:
<223> OTHER INFORMATION: Exemplary Sequence intended to illustrate how
      inventive reporter labeled beads can be used

<400> SEQUENCE: 9
agcttatcac                                                            10

<210> SEQ ID NO 10
<211> LENGTH: 10
<212> TYPE: DNA
<213> ORGANISM: Artificial Sequence
<220> FEATURE:
<223> OTHER INFORMATION: Exemplary Sequence intended to illustrate how
      inventive reporter labeled beads can be used

<400> SEQUENCE: 10
gcttatcacg                                                            10

<210> SEQ ID NO 11
<211> LENGTH: 10
<212> TYPE: DNA
<213> ORGANISM: Artificial Sequence
<220> FEATURE:
<223> OTHER INFORMATION: Exemplary Sequence intended to illustrate how
      inventive reporter labeled beads can be used

<400> SEQUENCE: 11
cttatcacgg                                                            10

<210> SEQ ID NO 12
<211> LENGTH: 10
<212> TYPE: DNA
<213> ORGANISM: Artificial Sequence
<220> FEATURE:
<223> OTHER INFORMATION: Exemplary Sequence intended to illustrate how
      inventive reporter labeled beads can be used

<400> SEQUENCE: 12
ttatcacggt                                                            10

<210> SEQ ID NO 13
<211> LENGTH: 10
<212> TYPE: DNA
<213> ORGANISM: Artificial Sequence
<220> FEATURE:
<223> OTHER INFORMATION: Exemplary Sequence intended to illustrate how
      inventive reporter labeled beads can be used

<400> SEQUENCE: 13
tatcacggta                                                            10
```

```
<210> SEQ ID NO 14
<211> LENGTH: 10
<212> TYPE: DNA
<213> ORGANISM: Artificial Sequence
<220> FEATURE:
<223> OTHER INFORMATION: Exemplary Sequence intended to illustrate how
      inventive reporter labeled beads can be used

<400> SEQUENCE: 14
atcacggtat                                                          10

<210> SEQ ID NO 15
<211> LENGTH: 10
<212> TYPE: DNA
<213> ORGANISM: Artificial Sequence
<220> FEATURE:
<223> OTHER INFORMATION: Exemplary Sequence intended to illustrate how
      inventive reporter labeled beads can be used

<400> SEQUENCE: 15
tcacggtatt                                                          10

<210> SEQ ID NO 16
<211> LENGTH: 10
<212> TYPE: DNA
<213> ORGANISM: Artificial Sequence
<220> FEATURE:
<223> OTHER INFORMATION: Exemplary Sequence intended to illustrate how
      inventive reporter labeled beads can be used

<400> SEQUENCE: 16
cacggtatta                                                          10

<210> SEQ ID NO 17
<211> LENGTH: 10
<212> TYPE: DNA
<213> ORGANISM: Artificial Sequence
<220> FEATURE:
<223> OTHER INFORMATION: Exemplary Sequence intended to illustrate how
      inventive reporter labeled beads can be used

<400> SEQUENCE: 17
acggtattaa                                                          10

<210> SEQ ID NO 18
<211> LENGTH: 10
<212> TYPE: DNA
<213> ORGANISM: Artificial Sequence
<220> FEATURE:
<223> OTHER INFORMATION: Exemplary Sequence intended to illustrate how
      inventive reporter labeled beads can be used

<400> SEQUENCE: 18
cggtattaaa                                                          10

<210> SEQ ID NO 19
<211> LENGTH: 10
<212> TYPE: DNA
<213> ORGANISM: Artificial Sequence
<220> FEATURE:
<223> OTHER INFORMATION: Exemplary Sequence intended to illustrate how
      inventive reporter labeled beads can be used

<400> SEQUENCE: 19
ggtattaaat                                                          10

<210> SEQ ID NO 20
```

```
<211> LENGTH: 10
<212> TYPE: DNA
<213> ORGANISM: Artificial Sequence
<220> FEATURE:
<223> OTHER INFORMATION: Exemplary Sequence intended to illustrate how
      inventive reporter labeled beads can be used

<400> SEQUENCE: 20
gtattaaatc                                                            10

<210> SEQ ID NO 21
<211> LENGTH: 10
<212> TYPE: DNA
<213> ORGANISM: Artificial Sequence
<220> FEATURE:
<223> OTHER INFORMATION: Exemplary Sequence intended to illustrate how
      inventive reporter labeled beads can be used

<400> SEQUENCE: 21
tattaaatcg                                                            10

<210> SEQ ID NO 22
<211> LENGTH: 10
<212> TYPE: DNA
<213> ORGANISM: Artificial Sequence
<220> FEATURE:
<223> OTHER INFORMATION: Exemplary Sequence intended to illustrate how
      inventive reporter labeled beads can be used

<400> SEQUENCE: 22
attaaatcga                                                            10

<210> SEQ ID NO 23
<211> LENGTH: 30
<212> TYPE: DNA
<213> ORGANISM: Artificial Sequence
<220> FEATURE:
<223> OTHER INFORMATION: Exemplary Sequence intended to illustrate how
      inventive reporter labeled beads can be used

<400> SEQUENCE: 23
atcgaaatcg aatagggcca taatttagct                                      30

<210> SEQ ID NO 24
<211> LENGTH: 10
<212> TYPE: DNA
<213> ORGANISM: Artificial Sequence
<220> FEATURE:
<223> OTHER INFORMATION: Exemplary Sequence intended to illustrate how
      inventive reporter labeled beads can be used

<400> SEQUENCE: 24
tagctttagc                                                            10

<210> SEQ ID NO 25
<211> LENGTH: 10
<212> TYPE: DNA
<213> ORGANISM: Artificial Sequence
<220> FEATURE:
<223> OTHER INFORMATION: Exemplary Sequence intended to illustrate how
      inventive reporter labeled beads can be used

<400> SEQUENCE: 25
agctttagct                                                            10

<210> SEQ ID NO 26
<211> LENGTH: 10
```

-continued

<212> TYPE: DNA
<213> ORGANISM: Artificial Sequence
<220> FEATURE:
<223> OTHER INFORMATION: Exemplary Sequence intended to illustrate how
      inventive reporter labeled beads can be used

<400> SEQUENCE: 26
gctttagctt                                                                10

<210> SEQ ID NO 27
<211> LENGTH: 10
<212> TYPE: DNA
<213> ORGANISM: Artificial Sequence
<220> FEATURE:
<223> OTHER INFORMATION: Exemplary Sequence intended to illustrate how
      inventive reporter labeled beads can be used

<400> SEQUENCE: 27
ctttagctta                                                                10

<210> SEQ ID NO 28
<211> LENGTH: 10
<212> TYPE: DNA
<213> ORGANISM: Artificial Sequence
<220> FEATURE:
<223> OTHER INFORMATION: Exemplary Sequence intended to illustrate how
      inventive reporter labeled beads can be used

<400> SEQUENCE: 28
tttagcttat                                                                10

<210> SEQ ID NO 29
<211> LENGTH: 10
<212> TYPE: DNA
<213> ORGANISM: Artificial Sequence
<220> FEATURE:
<223> OTHER INFORMATION: Exemplary Sequence intended to illustrate how
      inventive reporter labeled beads can be used

<400> SEQUENCE: 29
ttagcttatc                                                                10

<210> SEQ ID NO 30
<211> LENGTH: 10
<212> TYPE: DNA
<213> ORGANISM: Artificial Sequence
<220> FEATURE:
<223> OTHER INFORMATION: Exemplary Sequence intended to illustrate how
      inventive reporter labeled beads can be used

<400> SEQUENCE: 30
tagcttatcc                                                                10

<210> SEQ ID NO 31
<211> LENGTH: 10
<212> TYPE: DNA
<213> ORGANISM: Artificial Sequence
<220> FEATURE:
<223> OTHER INFORMATION: Exemplary Sequence intended to illustrate how
      inventive reporter labeled beads can be used

<400> SEQUENCE: 31
agcttatcac                                                                10

<210> SEQ ID NO 32
<211> LENGTH: 10
<212> TYPE: DNA

```
<213> ORGANISM: Artificial Sequence
<220> FEATURE:
<223> OTHER INFORMATION: Exemplary Sequence intended to illustrate how
      inventive reporter labeled beads can be used

<400> SEQUENCE: 32
gcttatcacg                                                              10

<210> SEQ ID NO 33
<211> LENGTH: 10
<212> TYPE: DNA
<213> ORGANISM: Artificial Sequence
<220> FEATURE:
<223> OTHER INFORMATION: Exemplary Sequence intended to illustrate how
      inventive reporter labeled beads can be used

<400> SEQUENCE: 33
cttatcccgg                                                              10

<210> SEQ ID NO 34
<211> LENGTH: 10
<212> TYPE: DNA
<213> ORGANISM: Artificial Sequence
<220> FEATURE:
<223> OTHER INFORMATION: Exemplary Sequence intended to illustrate how
      inventive reporter labeled beads can be used

<400> SEQUENCE: 34
ttatcacggt                                                              10

<210> SEQ ID NO 35
<211> LENGTH: 10
<212> TYPE: DNA
<213> ORGANISM: Artificial Sequence
<220> FEATURE:
<223> OTHER INFORMATION: Exemplary Sequence intended to illustrate how
      inventive reporter labeled beads can be used

<400> SEQUENCE: 35
tatcccggta                                                              10

<210> SEQ ID NO 36
<211> LENGTH: 10
<212> TYPE: DNA
<213> ORGANISM: Artificial Sequence
<220> FEATURE:
<223> OTHER INFORMATION: Exemplary Sequence intended to illustrate how
      inventive reporter labeled beads can be used

<400> SEQUENCE: 36
atcccggtat                                                              10

<210> SEQ ID NO 37
<211> LENGTH: 10
<212> TYPE: DNA
<213> ORGANISM: Artificial Sequence
<220> FEATURE:
<223> OTHER INFORMATION: Exemplary Sequence intended to illustrate how
      inventive reporter labeled beads can be used

<400> SEQUENCE: 37
tcacggtatt                                                              10

<210> SEQ ID NO 38
<211> LENGTH: 10
<212> TYPE: DNA
<213> ORGANISM: Artificial Sequence
```

```
<220> FEATURE:
<223> OTHER INFORMATION: Exemplary Sequence intended to illustrate how
      inventive reporter labeled beads can be used

<400> SEQUENCE: 38
cccggtatta                                                                10

<210> SEQ ID NO 39
<211> LENGTH: 10
<212> TYPE: DNA
<213> ORGANISM: Artificial Sequence
<220> FEATURE:
<223> OTHER INFORMATION: Exemplary Sequence intended to illustrate how
      inventive reporter labeled beads can be used

<400> SEQUENCE: 39
acggtattaa                                                                10

<210> SEQ ID NO 40
<211> LENGTH: 10
<212> TYPE: DNA
<213> ORGANISM: Artificial Sequence
<220> FEATURE:
<223> OTHER INFORMATION: Exemplary Sequence intended to illustrate how
      inventive reporter labeled beads can be used

<400> SEQUENCE: 40
cggtattaaa                                                                10

<210> SEQ ID NO 41
<211> LENGTH: 10
<212> TYPE: DNA
<213> ORGANISM: Artificial Sequence
<220> FEATURE:
<223> OTHER INFORMATION: Exemplary Sequence intended to illustrate how
      inventive reporter labeled beads can be used

<400> SEQUENCE: 41
ggtattaaat                                                                10

<210> SEQ ID NO 42
<211> LENGTH: 10
<212> TYPE: DNA
<213> ORGANISM: Artificial Sequence
<220> FEATURE:
<223> OTHER INFORMATION: Exemplary Sequence intended to illustrate how
      inventive reporter labeled beads can be used

<400> SEQUENCE: 42
gtattaaatc                                                                10

<210> SEQ ID NO 43
<211> LENGTH: 10
<212> TYPE: DNA
<213> ORGANISM: Artificial Sequence
<220> FEATURE:
<223> OTHER INFORMATION: Exemplary Sequence intended to illustrate how
      inventive reporter labeled beads can be used

<400> SEQUENCE: 43
tattaaatcg                                                                10

<210> SEQ ID NO 44
<211> LENGTH: 10
<212> TYPE: DNA
<213> ORGANISM: Artificial Sequence
<220> FEATURE:
```

-continued

```
<223> OTHER INFORMATION: Exemplary Sequence intended to illustrate how
      inventive reporter labeled beads can be used

<400> SEQUENCE: 44
attaaatcga                                                          10
```

METHOD AND APPARATUS FOR READING REPORTER LABELED BEADS

RELATED APPLICATIONS

This application is a divisional application of prior conventional application Ser. No. 09/976,237, filed on Oct. 12, 2001 and issued as U.S. Pat. No. 6,934,408 on Aug. 23, 2005, which itself is based on prior provisional application Ser. No. 60/240,125, filed on Oct. 12, 2000, and prior provisional application Ser. No. 60/242,734, filed on Oct. 23, 2000, the benefits of the filing dates of which are hereby claimed under 35 U.S.C. § 119(e) and under 35 U.S.C. § 120. Application Ser. No. 09/976,237, the immediate parent of this divisional application, is further based on prior conventional application Ser. No. 09/939,292, filed on Aug. 24, 2001 and issued as U.S. Pat. No. 6,532,061 on Mar. 11, 2003, which is based on a prior provisional application Ser. No. 60/228,076, filed on Aug. 25, 2000, the benefits of the filing dates of which are hereby claimed under 35 U.S.C. § 119(e) and under 35 U.S.C. § 120.

FIELD OF THE INVENTION

The present invention generally relates to a method and apparatus employed to image an encoded reporter labeled bead, and more specifically, to a method and apparatus that enable encoded reporter labeled beads to be imaged in stasis or when entrained in a flow of fluid, such that imaging data thus obtained can be employed to decode each encoded bead by determining the identity of reporters bound to that bead.

BACKGROUND OF THE INVENTION

Single nucleotide polymorphisms (SNPs) are locations in the genome where a single base substitution has occurred. SNPs are estimated to occur in the human genome at a frequency of approximately 1:1000, implying that there are three million
SNPs in the three billion nucleotide human genome. Since most known gene sequences are on the order of 1,000 base pairs in length, each gene is expected to contain one SNP. It is estimated that there are 100,000 human genes, meaning that there are 100,000 SNPs, which may directly affect the function and/or expression of the resulting proteins.

The relative abundance of SNPs in the genome has stimulated efforts to quantify the location and frequency of occurrence of single base substitutions as a tool for the analysis of gene function. Methods for the detection of SNPs include the oligonucleotide ligation assay (OLA), single-strand conformation polymorphism analysis, allele-specific oligonucleotide (ASO) hybridization, and the single base chain extension (SBCE) assay.

While SNPs are abundant, an individual SNP is not rich in information. Most SNPs are in non-coding or non-regulatory regions of the genome and may not affect gene expression at all. Of those SNPs that occur within the coding regions, many are likely to occur in non-critical regions of the resulting protein or may result in a benign (or nonexistent) amino acid substitution and therefore have little or no bearing on the protein's function. Further, only a fraction of the total number of genes are actively expressed at a given time, so the presence of an SNP within a gene does not indicate a priori that it has significant phenotypic relevance. Since the fraction of phenotypically relevant SNPs is small, it is useful to have a high throughput means of analyzing SNPs in order to identify those of biological importance. Once the genome has been thoroughly analyzed and the locations and relative abundances of important SNPs have been identified, a multiplexed method of SNP analysis from an individual's deoxyribonucleic acid (DNA) will be clinically useful. It would therefore be desirable to have a high throughput method for analyzing numerous SNPs in a short period of time.

The locations of SNP and other polymorphic loci within the genome can be determined by sequencing and comparing the same sections of the genome from numerous individuals. Those locations within the genome that are statistically variable across individuals are polymorphic. The biological relevance of a given polymorphism can be determined by correlating the different alleles to the presence of disease or other phenotypic traits. Hence, there is a need for a robust, inexpensive, and widely available method for sequencing gene-sized lengths of DNA in order to discover the locations and biological relevance of polymorphic sites.

One SNP analysis method calls for the binding of oligonucleotides to supports such that numerous identical oligos are bound to a solid support, and so that different supports bear different oligo sequences. One method of encoding an oligonucleotide library useful for SNP analysis is to place unique optical reporters on solid supports during combinatorial chemical synthesis. The attachment of reporters to the supports may be by means of covalent bonds, colloidal forces or other such means, to ensure that reporters stay in contact with, or in close proximity to, the solid support. The solid supports are typically beads of polystyrene, silica, resin, or any another substance on which compounds can be readily synthesized and to which reporters can be affixed in a split/add/pool (SAP) combinatorial process. Each reporter encodes both the identity of a molecular component as well as its place in the synthetic process. By enumerating the optical characteristics of each reporter bound to a solid substrate it is possible to decode libraries of unique compounds numbering in the billions. As noted above, useful genetic assays can be performed by combinatorially synthesizing oligonucleotides on a bead library such that a given bead bears numerous identical covalently bound oligos and each bead in the library bears a different oligo sequence. In addition to its oligo sequence, each bead bears a unique optical signature comprising a predefined number of unique reporters, where each reporter has a predefined combination of different fluorochromes. A bead's optical signature is correlated to the addition sequence of each reporter during the synthetic process to enable identifying the unique nucleotide sequence on that bead. By imaging the beads, the optical signatures can be read and correlated to the corresponding oligo sequences.

In addition to DNA analyses, the reporter labeling method is also useful for synthesizing diverse libraries of chemical compounds on beads for subsequent analyses in drug candidate screening. Likewise the same method can be used for synthesis of protein libraries on beads where the base unit of synthesis is one of twenty amino acid sequences.

Generally, with only a few reporters and colors, the number of unique signatures that can be created is quite substantial. For example, using only five colors and five reporters, more than 10,000 unique signatures can be generated. Using six colors and 10 reporters, over 115 million unique signatures can be generated to create a very diverse bead library. Clearly, the number of unique combinations that can be identified using reporter labeled beads is substantial. The nature of the apparatus required to identify the unique spectral signatures of such beads is discussed in greater detail below.

Substrate-Based Approach to Analyzing Reporter Labeled Beads

In order to read the reporter signature of a bead, an image of the bead must be acquired with sufficient spatial resolution to discriminate the locations of individual reporters. If reporter size or shape are used in the signature scheme, the spatial resolution must be sufficient to discriminate these parameters as well. Further, the acquired image must have sufficient spectral resolution to accurately discriminate the multiple colors emitted from a single reporter. Further still, the quality of the imagery of each bead acquired must be sufficient to ensure that at least one copy of every unique reporter on a bead is evident in the view. Even when multiples of each reporter are bound to a bead, there remains a probability that not every unique reporter will be resolved in a given image. Reporters may not be in clear focus or they may not be exposed to the optical collection system because of their disposition on the bead. In such cases, multiple images should be acquired of each bead at different focal planes or from different perspectives to ensure at least one copy of every unique reporter is successfully discriminated.

One technique that might be used to read the reporter signature on beads using a conventional fluorescence microscopy apparatus would require that the beads be laid down on a planar substrate in order to present an optically readable bead array. If the beads were used in an assay prior to being affixed to a substrate, the assaying process should not disrupt the bound reporter signature. In the case where beads are affixed to a substrate before being used in an assay, the advantageous kinetics associated with the large surface area to volume ratio of free beads is lost. Nevertheless, the limitations of conventional microscopy techniques impose the requirement that beads be affixed to a substrate prior to analysis, thereby adding numerous preparatory steps to bead-based assays. These preparatory steps add time and expense, while simultaneously reducing the flexibility and utility of bead-based analytical processes.

In one bead arraying method, described in U.S. Pat. No. 5,855,753, beads are placed on a substrate and caused to form a fixed monolayer through the use of an electric field. An "electrochemical sandwich" is formed by suspending the beads in an electrolytic fluid placed between an anode and a cathode. Using either an alternating current (AC) and or a direct current (DC) field applied to the sandwich in an appropriate manner, over time, the beads are caused to aggregate in specific groups, in a monolayer on the substrate.

Another bead arraying method is described in International Patent Application WO97/40385, which indicates that the electrochemical sandwich method is further enhanced by use of a specialized electrode in conjunction with externally applied illumination patterns that serve to further control the electrokinetic forces, which mediate bead aggregation on a substrate. U.S. Pat. No. 5,695,934 discloses yet another method in which beads are laid on a substrate and affixed by chemical affinity between the functionalized surface of the substrate and bead-bound moieties. Other methods for arraying beads on substrates exist, but in all such methods, the goal is to ensure that the bead layer is fixed in place, preventing movement of the beads during the process of reading the beads. Typically, in any microscopy process for reading beads, it would be necessary to affix the bead-substrate to a two-axis stage and move the stage in a pattern that enables each portion of the substrate to be read. This process involves numerous cycles of acceleration and deceleration of the substrate as it is moved on the stage, which would likely induce independent movement of the beads, if they are not securely affixed to the substrate.

Bead movement is not the only complication associated with reading labeled beads on a planar substrate. Another consideration is the need for achieving an accurate focus across the field of view (FOV), which can be compromised by any non-planarity of the packed beads on the substrate or by any non-planarity of the substrate itself. For these reasons, the focus on each portion of the bead array must be individually achieved to ensure proper resolution. Although autofocus systems are well known in the art, the focus step requires additional time, expense, and adds variability to the process. Additional images may be required to discriminate the different fluorescence emission spectra of bead-bound signaling molecules and of the reporters themselves. In addition, if the signaling molecules or reporters are randomly distributed on the beads, it may not be possible to identify signals or signatures from a fraction of the beads due to the absence of the signals or reporters from the planar FOV. The planar substrate preparation presents only one, or at most two, of six possible perspectives from which to view the bead, increasing the likelihood that reporters will be hidden from the imaging system.

The complexity associated with arraying beads hinders bead-based analytical approaches, regardless of the number of beads in the library. As the size of an analytical bead library grows beyond roughly a million beads, the substrate-based approach to bead imaging becomes highly impractical. Significant difficulties arise when tens of millions to billions of beads must be analyzed, requiring that the bead array substrates grow substantially in size. The difficulties involved in creating a uniform, tightly packed, fixed array increase greatly with the size of the array. Furthermore, accurate and rapid positioning of the array during the imaging process becomes far more difficult. The size, expense, and low throughput of such systems rule out their widespread use in research and for point-of-care applications. Therefore, an improved method for analyzing beads is desired. Preferably this method should eliminate the need for placing the beads on a substrate and enable the simultaneous imaging of multiple focal planes and multiple bead orientations. Ideally, this new method would simultaneously image the entire spectrum of bead fluorescent emissions and provide enough spectral resolution to discriminate the colors originating from each reporter. Finally, an ideal method would conveniently handle billions of beads and enable ultra-high speed imaging to analyze large bead libraries in a matter of hours.

SUMMARY OF THE INVENTION

In accord with the present invention, a method and apparatus for imaging and reading reporter labeled beads are provided. The method and apparatus of the present invention enable individual encoded beads to be imaged, and the compound attached to that bead to be identified as a function of image data, so that the identity and sequence of all sub units of the compound are determined. Generally, a single encoded bead will include redundant copies of the same compound and the associated reporters. In one preferred application of the present invention, the sub units are oligos, the resulting compound is an oligonucleotide, and each reporter is preferably discriminable by its color. However, other types of sub units forming other types of compounds and reporters that are uniquely discriminable by characteristics other than color can be imaged and decoded using the method and system of the present invention. Essentially, any characteristic that is determinable via imaging, such as size and shape, can be employed as a reporter characteristic.

It should also be understood that the method and apparatus of the present invention may be applied to image and decode reporter labeled beads independently of the process employed to produce such reporter labeled beads. It is anticipated that processes such as stochastic synthesis, directed synthesis, combinations thereof, or the attachment of a pre-synthesized compounds to previously (or subsequently) encoded reporter labeled beads will be employed to produce reporter labeled beads. Unlike a stochastic SAP process, in a directed synthesis the path of each bead is predetermined during compound synthesis and reporter addition. When reporter labeled beads are used with pre-synthesized compounds all unique reporter types may be bound to the carrier in one step to create a unique signature for the bead. In this case the unique combination of reporters bound to a bead simply create a unique identity and do not necessarily encode the subunit sequence for the compound bound to the bead. A cross reference table or other means may be created to correlate bead signature to compound identity. In this case the present invention may be used to identify the unique bead signature to determine compound identity by searching the cross reference table.

The basic method involves focussing light from an encoded bead along a collection path, and dispersing the light into a plurality of light beams as a function of a plurality of different discriminable characteristics of the light that are indicative of the plurality of different reporters associated with the encoded bead. Each light beam is focussed to produce a respective image corresponding to that light beam. A plurality of signals are generated in response to the respective images thus produced. Each signal generated indicates whether a different one of the plurality of reporters is associated with the encoded bead. The signals are analyzed to decode a sequence and to identify the sub units forming a component attached to the encoded bead, and these steps are repeated for successive encoded beads.

Preferably, the step of dispersing comprises the steps of dividing the light into the plurality of light beams as a function of the wavelength of the light beams. Also preferably, the step of analyzing the plurality of signals comprises the step of constructing a sequence library of the plurality of components based on each encoded bead that is decoded.

It may be necessary to illuminate an encoded bead with light to enable the encoded bead to be read. In one embodiment, the encoded beads are entrained in a fluid, and the encoded beads are imaged in a flow of the fluid. However, the present invention does not require that the beads be imaged in a fluid flow.

Preferably the encoded beads are analyzed by determining one or more portions of each image corresponding to a unique reporter, and then determining a signature of each reporter based on the image data. The reporters thus identified determine the identity and the sequence in which the sub units that form the compound attached to the encoded bead were added.

A predefined number of unique reporters should be detected on an encoded bead. The method can also include the step of disregarding all signals relating to an encoded bead if the plurality of signals for that encoded bead indicate that fewer reporters are associated with the encoded bead than were expected. This step can be facilitated by referring to an encoded bead legend that relates each unique reporter to a specific sub unit and a specific disposition of that sub unit in a sequence that forms a compound.

It should also be noted that encoded beads are usable to analyze DNA sequences, or for other DNA related research. In such an application, it is preferable not to collect data for encoded beads that have not experienced a binding event. Beads that have experienced a binding event are referred to herein as "positive" beads. In at least one embodiment of the present invention, only data from positive beads are analyzed.

Several different embodiments of imaging apparatus are usable to image and decode encoded beads. In general, the apparatus will include a collection lens to collect and focus light from an encoded bead in a desired direction, a dispersing component that receives the light from the collection lens and disperses the light into a plurality of light beams as a function of a plurality different discriminable characteristics of the light, such that the plurality of different discriminable characteristics are indicative of a plurality of different reporters. Also included is at least one pixelated detector; and an imaging lens that focusses each of the plurality of light beams on the at least one pixelated detector, thereby producing a respective image corresponding to each of the plurality of light beam. The pixelated detector provides an output signal for each respective image, such that each output signal may individually, or in combination with other output signals, indicate whether a different reporter is present on the encoded bead. A signal processor is coupled to the pixelated detector to receive its output signal and processes the output signal to decode the identity and sequence of the sub units that form the compound attached to an encoded bead, or alternatively, to decode the bead to identify the compound using a cross reference table.

Preferably, in one exemplary application, the signal processor is adapted to generate sequence contigs from a plurality of decoded sequences representing a plurality of encoded beads. Such sequence contigs preferably are used to identify at least one of a genomic DNA sequence, a polymorphic allele, and an expressed gene.

The signal processor can be adapted to disregard all output signals relating to a reporter if signals from an identical reporter have already been analyzed. The signal processor can similarly be adapted to disregard all output signals for an encoded bead if the signals indicate that fewer than a predetermined number of reporters are associated with the encoded bead. The signal processor is preferably adapted to employ an encoded bead legend that relates each unique reporter to a specific sub unit and a specific disposition in a sequence of sub units that comprise the compound associated with the encoded bead. By employing such an encoded bead library, the signal processor can selectively disregard all output signals if it is determined that the encoded bead does not correspond to that encoded bead legend. Alternatively, the signal processor can be adapted to employ a cross reference table (such as the reporter legend of FIG. 19) to relate bead identity to compound identity. Also, the signal processor can be controlled to only analyze signals relating to positive encoded beads.

In at least one embodiment, the encoded beads are entrained in a fluid and imaged while the fluid is flowing through the imaging system. The imaging system includes a bead reservoir containing encoded beads that have not been imaged, and fluid channels to control a flow of fluid. A light source is optionally included to illuminate the encoded bead to be imaged.

The dispersing component is preferably either a prism or a plurality of dichroic filters. If a prism is employed, the images will be convolved and the signal processor will need to deconvolve the images. One or more time delay and integration (TDI) detectors are also preferably included in the imaging system to detect the light from the beads. In one embodiment, a plurality of dichroic filters, imaging lenses, and detectors are included.

Still another aspect of the present invention relates to a method for simultaneously imaging a plurality of reporters disposed on substantially different portions of an encoded bead, to identify each unique reporter included on the encoded bead. The method includes the steps of receiving light from the encoded bead along a plurality of collection paths that are substantially spaced apart, such that light from the reporters disposed on the different portions of the encoded bead affect the light received therefrom. The light is processed to identify each unique reporter included on the encoded bead.

A final aspect of the present invention is directed to a method for employing an oligo library encoded on beads for at least one of DNA sequencing, a polymorphism analysis, and an expression analysis. An imaging system capable of decoding a sequence of encoded beads conveyed in a flow of fluid is provided. Essentially, a complete encoded bead library of N-mer oligos is generated, and the library is used to perform either the DNA sequencing, the polymorphism analysis, or the expression analysis. Positive beads are imaged and decoded using imaging data produced by an imaging system such as described above.

When DNA sequencing is the analysis function that is selected, the genomic DNA component is amplified using primers for extended sequences of interest. When a polymorphism analysis function is selected, the genomic DNA component is amplified using primers for polymorphic regions of interest. Alternatively, when an expression analysis function is selected, the ribonucleic acid (RNA) component is amplified using primers for genes of interest.

Regardless of the specific analysis function that is selected, the amplified component is hybridized to the encoded bead library; and the imaging system is employed to identify oligo sequences of encoded beads hybridized as noted above. From the imaging data, sequence contigs are constructed from the oligo sequences identified by the imaging analysis to identify either a genomic DNA sequence, a polymorphic allele, or an expressed gene. In a preferred embodiment, the N-mer oligos comprise oligos having a length equal to ten.

BRIEF DESCRIPTION OF THE DRAWING FIGURES

The foregoing aspects and many of the attendant advantages of this invention will become more readily appreciated as the same becomes better understood by reference to the following detailed description, when taken in conjunction with the accompanying drawings, wherein.

DESCRIPTION OF THE PREFERRED EMBODIMENT

It is contemplated that the present invention may be applied to combinatorially created beads and compounds as well as specifically directed synthesis of beads and compounds. Further details regarding both of these aspects of the present invention are discussed below.

New Method for Analyzing Reporter Labeled Beads

A new bead imaging system and method for analyzing reporter labeled beads addresses the problems for carrying out this task that would arise in reading beads using any conventional approach and adds new capabilities to the analysis and handling of reporter labeled beads. The imaging system enables the discrimination of the different reporters attached to each bead and therefore enables the decoding of the complete reporter signature and corresponding chemical identity (e.g., oligonucleotide sequence) bound to the bead. By preferably handling beads in suspension and using hydrodynamic focussing, billion-count bead samples can easily be moved through the field of view (FOV) of a flow imaging system at high rates. Existing non-imaging flow cytometers cannot be used with this combinatorial scheme because on a given bead, different reporters with any colors in common at the same intensity cannot be distinguished from each other without spatial information. Similarly, without image information, different reporter sizes or shapes, which can confer part of the information included in a reporter signature, cannot be discriminated. It should be noted that while a preferred embodiment of the present invention contemplates imaging encoded beads while entrained in a flow of fluid, encoded beads can be imaged in stasis, and a flow is not required. It is contemplated that imaging encoded beads in a flow of fluid will enable a large number of beads to be rapidly imaged and analyzed. It is anticipated that the resolution afforded by the present invention will enable the reporters themselves to be small beads of polystyrene, silica, resin, or any another substance that can be fabricated or treated to possess a unique optical signature, which are then associated with larger (yet still relatively small) substrate beads.

An embodiment of the present invention for analyzing beads in flow includes subsystems for implementing the tasks of: (1) optical signal collection and spectral decomposition; (2) pixelated detection; (3) illumination; (4) bead velocity detection; and (5) sample handling. One or more embodiments of each of these subsystems is described in detail below.

Figure 1:
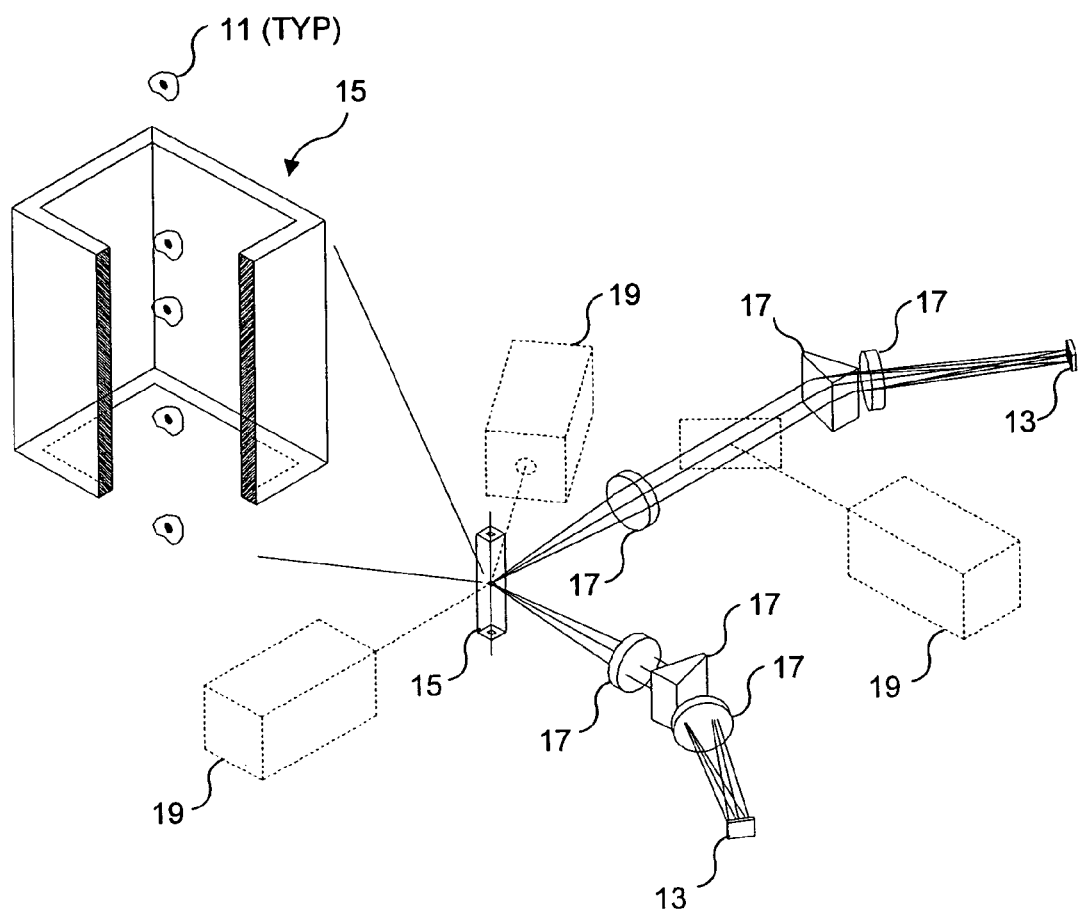
FIG. 1 is an isometric view of an embodiment of an imaging system useful for imaging reporter beads, in which multiple legs are employed for the spectral decomposition and imaging to collect light signals from multiple perspective positions.

An important aspect of the present invention lies in its ability to simultaneously discriminate the location of the various fluorescent emission spectra produced by reporters attached to the solid substrates (beads). This ability enables the rapid determination of the presence or absence of a binding event and the identity of each bead (i.e., its reporter signature) after a bead has passed through the field of view (FOV). Hydrodynamic focussing ensures that the beads are at or near the focal plane of the imaging system. When required, an optical correction can be applied to account for minor changes in the location of the hydrodynamically focussed bead column. In addition, the imaging system can be constructed to view the beads from multiple angles to produce image data of a different fraction of the bead surface, to enable the construction of a three-dimensional representation of each bead. This configuration also enables correction of focus errors. The present invention spectrally decomposes the signal from each reporter in the axis perpendicular to flow and then forms an image of the reporters on a bead onto a single detector or multiple detectors. FIG. 1 schematically illustrates this process.

As shown in FIG. 1, a plurality of marked beads 11 pass through a sampling column 15 in a single file orientation. The imaging system shown includes a plurality of detectors 13, focussing elements or lenses 17, and one or more light source(s) 19. The location of the image on the detector is then determined by the spectral content of the signal emitted from the reporter as well as the spatial position of the reporter with respect to the bead. There are five embodiments of the present invention that accomplish the spectral decomposition and imaging of the beads.

First Embodiment for Spectral Decomposition and Imaging

Figure 2A:
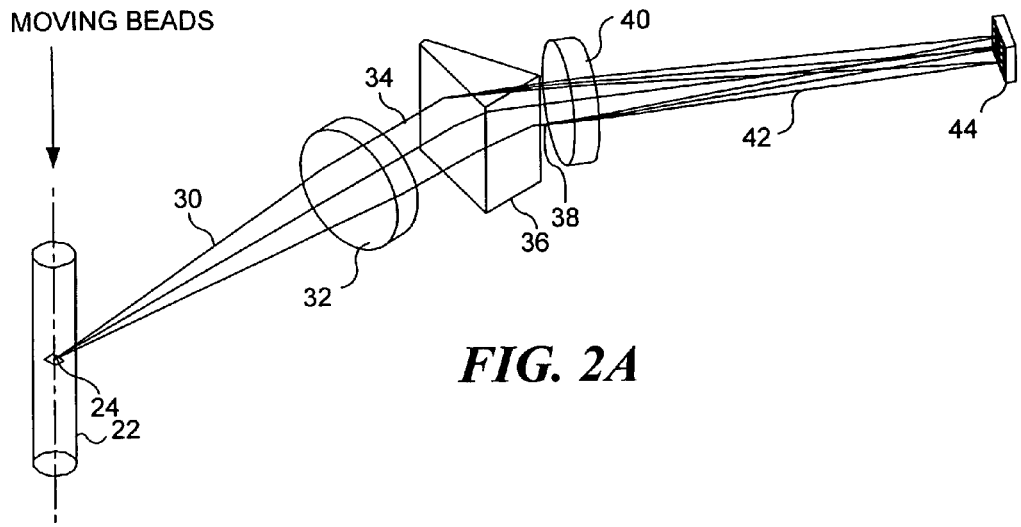
FIGS. 2A and 2C are isometric views of two related embodiments of an imaging system using a prism for spectral dispersion of light and usable for imaging reporter beads, wherein FIG. 2C also includes a slit for spatial filtering of extraneous light.

A first embodiment of the system for spectral decomposition and imaging is shown in FIG. 2A, and this embodiment is also disclosed in commonly assigned U.S. Pat. No. 6,211,955, entitled "Imaging and Analyzing Parameters of Small Moving Objects Such as Cells," filed on Mar. 29, 2000, the drawings and disclosure of which are hereby specifically incorporated herein by reference. In this previously filed application, there is no discussion of identifying reporters on beads. However, the following discussion describes how the apparatus disclosed in this previously filed application can be employed for spectral decomposition and imaging of objects such as beads and reporters included thereon. In regard to the present invention, a bead provided with reporters is simply a specific type of object. (It should be noted that where there is any variance between the description in any document incorporated herein by reference and the present disclosure, the present disclosure takes precedence.)

Although several types of pixelated detectors may be used in the present invention, in many cases a time delay integration (TDI) detector is preferable. The TDI detector preferably comprises a rectangular charge-coupled device (CCD) that employs a specialized pixel readout algorithm, as explained below. Non-TDI CCD arrays are commonly used for two-dimensional imaging in cameras. In a standard CCD array, photons that are incident on a pixel produce charges that are trapped in the pixel. The photon charges from each pixel are readout of the detector array by shifting the charges from one pixel to the next, and then onto an output capacitor, producing a voltage proportional to the charge. Between pixel readings, the capacitor is discharged and the process is repeated for every pixel on the chip. During the readout, the array must be shielded from any light exposure to prevent charge generation in the pixels that have not yet been read.

In one type of TDI detector 44, which comprises a CCD array, the CCD array remains exposed to the light as the pixels are readout. The readout occurs one row at a time from the top toward the bottom of the array. Once a first row is readout, the remaining rows are shifted by one pixel in the direction of the row that has just been read. If the object being imaged onto the array moves in synchrony with the motion of the pixels, light from the object is integrated for the duration of the TDI detector's total readout period without image blurring. The signal strength produced by a TDI detector will increase linearly with the integration period, which is proportional to the number of TDI rows, but the noise will increase only as the square root of the integration period, resulting in an overall increase in the signal-to-noise ratio by the square root of the number of rows. One TDI detector suitable for use in the present invention is a Dalsa Corp., Type IL-E2 image sensor, although other equivalent or better image sensors can alternatively be used. The Dalsa image sensor has 96 stages or rows, each comprising 512 pixels; other types of image sensors useable in the present invention may have different configurations of rows and columns or a non-rectilinear arrangement of pixels. The Dalsa sensor has approximately 96 times the sensitivity and nearly 10 times the signal-to-noise ratio of a standard CCD array. The extended integration time associated with TDI detection also serves to average out temporal and spatial illumination variations, increasing measurement consistency.

It should be emphasized that the present invention is not limited to TDI detectors or CCD types of TDI detectors. Other types of TDI detectors, such as complementary metal oxide semiconductor (CMOS) and multi-channel plate imaging devices might also be used for the TDI detector in the present invention. It is important to understand that any pixelated device (i.e., having a multitude of light sensitive regions) in which a signal produced in response to radiation directed at the device can be caused to move through the device in a controlled fashion is suitable for use as the TDI detector in the present invention. Typically, the signal will move in synchrony with a moving image projected onto the device, thereby increasing the integration time for the image, without causing blurring. However, the motion of the signal can be selectively desynchronized from the motion of the radiation image, as required to achieve a desired affect.

Figure 2B:
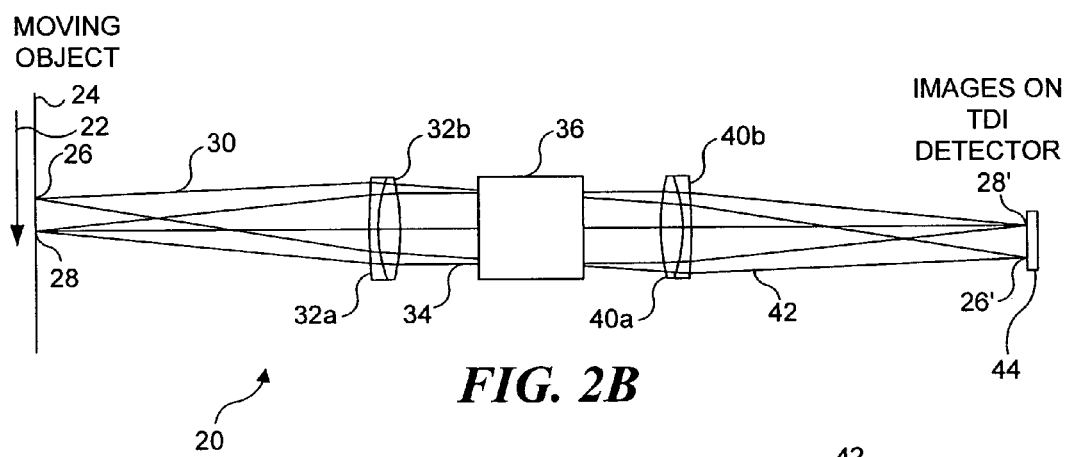
FIG. 2B is an schematic view of embodiment 2A showing bead traversal along a direction of motion in both object and image space.
Figure 2C:
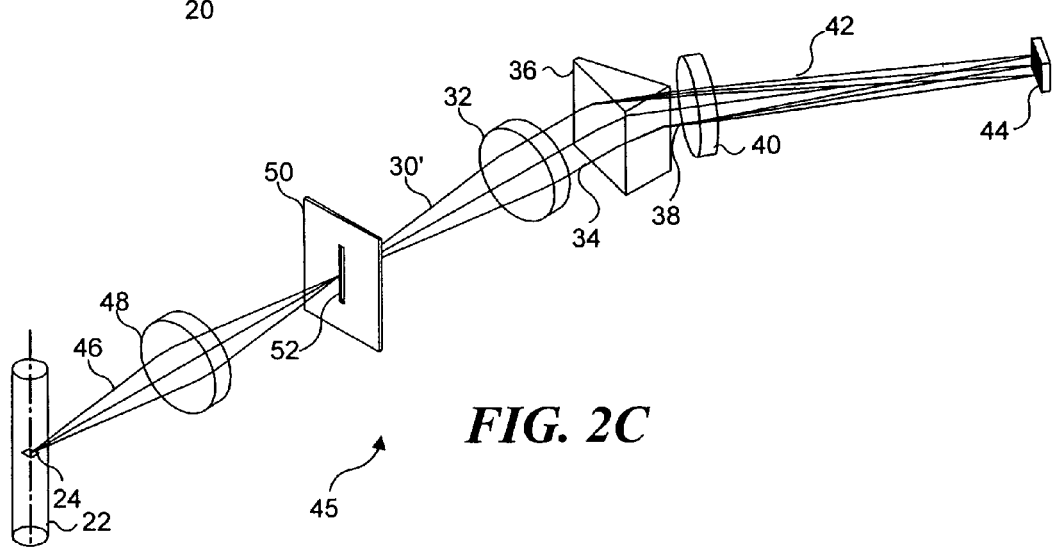
Figure 4:
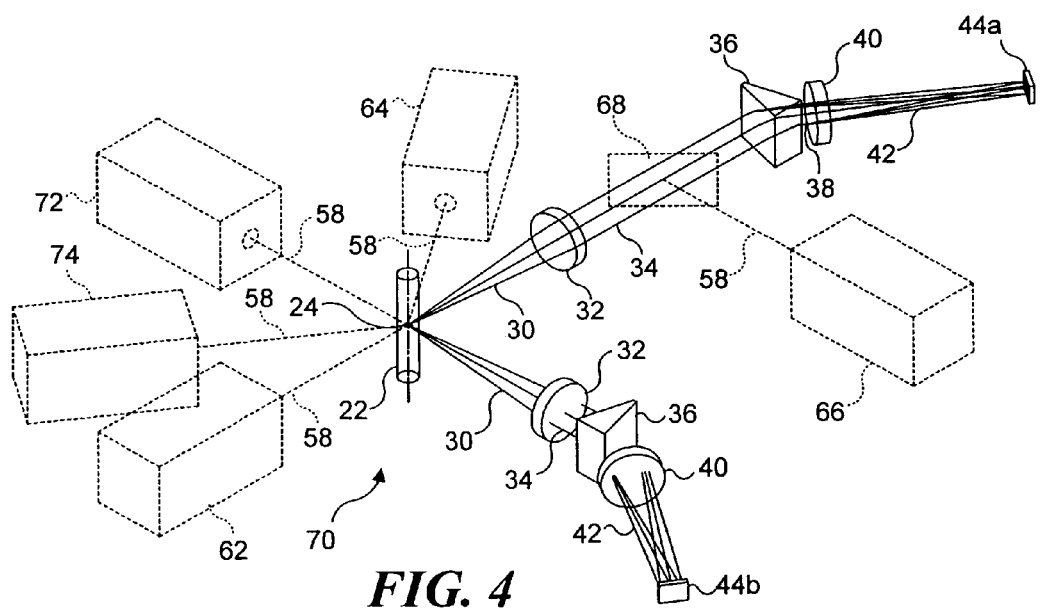
FIG. 4 is an alternative embodiment of the imaging apparatus in FIGS. 2A and 3, in which a second set of imaging components and time delay integration (TDI) detector are included for monitoring light from a bead, to avoid interference between different reporters, and showing alternative locations for one or more light source(s)
Figure 11:
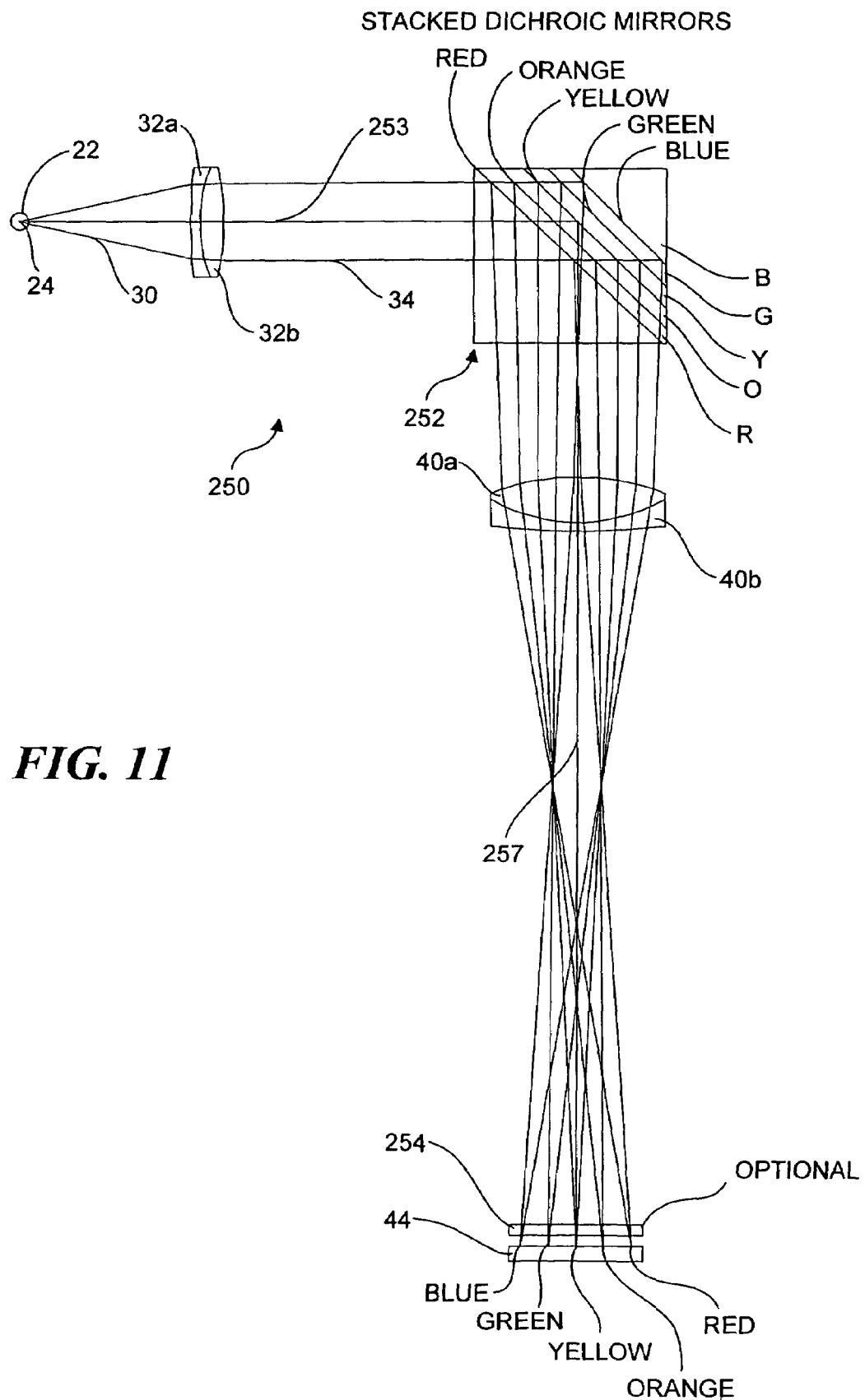
FIG. 11 is a plan view of an alternate embodiment for an imaging system usable in the present invention that employs a spectral dispersion component comprising a plurality of stacked dichroic filters that spectrally separate the light.

In imaging systems 45, 70, 250 in FIGS. 2C, 4, and 11 respectively, and in other embodiments of the present invention that employ a fluid flow to carry objects through the imaging system, a flow-through cuvette or a jet (not shown) contains the reporter labeled beads or other objects being analyzed. The velocity and cellular concentration of the fluid may be controlled using syringe pumps, gas pressure, or other pumping methods (not shown) to drive a sample solution through the system to match the pixel readout rate of the TDI detector. However, it should be understood that the readout rate of the TDI detector can be selectively controlled, as required, to match the motion of the sample solution.

As will be evident in FIG. 2B, if the Figure depicts the imaging of object 24 over time, the object is shown at both a position 26 and a, position 28 as it moves with fluid flow 22. As a consequence, images of object 24 will be produced on the detector at two discrete spatial positions 26' and 28', as indicated on the right side of FIG. 2B. In the case of TDI detection, the signal on the detector can be made to move in synchronicity with image of object 24 such that signal is collected and integrated over the entire traversal of the detector. Alternatively, if FIG. 2B is depicting a single instant in time, positions 26 and 28 can represent the location of two separate objects, which are simultaneously imaged on the detector at positions 26' and 28'.

As shown in the FIG. 2A, light from a column 22 of beads 24 that is hydrodynamically focussed to a well defined region, is collimated by passing through a collection lens 32. The light from the beads travels along a collection path 30. A spectral dispersing element 36 disposed in the collection path spectrally disperses the collimated light that has passed through the collection lens in a plane substantially orthogonal to a direction of relative movement between the beads and the imaging system, producing spectrally dispersed light. An imaging lens 40 is disposed to receive the spectrally dispersed light, producing an image from the spectrally dispersed light 38. Also included is a pixelated detector 44, disposed to receive the image produced by the imaging lens. As the movement occurs, the image of the bead produced by the imaging lens moves from row to row across the detector. As will be described earlier, the detector may be a TDI-type detector or a frame type detector, depending upon the specific embodiment.

As a result of light collimation by the collection lens in this embodiment, all light emitted from a first point in the bead travels in parallel rays. Light emitted from a second point in the bead will also travel in parallel rays, but at a different angle relative to light from the first point. In this manner, spatial information in the bead is transformed by the collection lens into angular information in the collection path. The spectral dispersing element acts on the collimated light such that different spectral components leave the spectral dispersing element at different angles, in a plane substantially orthogonal to the direction of the relative movement between the bead and the imaging system. In this manner, both spatial and spectral information in the bead are transformed into angular information. The imaging lens acts on the light from the dispersing element to transform different light angles into different positions on the detector. Spatial information is preserved by the system since light from the different positions in the bead is projected along a path 42 to different positions on the detector, in both axes. In addition, light of different spectral composition that originates from the bead is projected to different positions on the detector in an axis substantially orthogonal to the relative movement between the bead and the imaging system. In this manner, the spatial information from the bead is preserved, and spectral information covering a large bandwidth at high resolution is simultaneously collected.

When used for bead identification in accord with the present invention, this apparatus provides substantial utility in resolving reporter locations and spectra on the detector, even when the reporters are disposed in spatially close relationship within a bead. When spectral imaging occurs in the present invention, the spatial distribution of light in the bead is convolved with the spectral distribution of that light to produce the image of the bead at the detector. This convolution can result in blurring in the dispersion axis, depending on the spectral bandwidth of the light. Narrow spectral bandwidths will result in little or no blurring, depending on the spectral resolution of the system. In the present invention, it is contemplated that the spectral resolution will be approximately 3 nm per pixel, with a spatial resolution in object space of approximately 1 micron. However, the spatial and spectral resolution can be adjusted to match the requirements of a particular application and the values noted herein should not be considered as limiting on the scope of the present invention.

Alternate embodiments of the imaging system illustrated in FIG. 2A and useful for imaging beads are shown in FIGS. 2C-4. These alternate embodiments differ in the number and orientation of various optical components, as described below, but generally function in the same manner as the imaging system of FIG. 2A.

FIG. 2C illustrates an imaging system 45 that includes a slit 52 used to prevent extraneous light from reaching pixelated detector 44. In imaging system 45, light 46 from bead 24 (or other object) is focussed by an objective lens 48 onto slit 52. Slit 52, as shown in FIG. 2C, is sufficiently narrow to block light that is not focussed onto the slit by objective lens 48, thereby preventing extraneous light from passing through the slit. Light 30', which has passed through the slit, is collected by collection lens 32, as discussed above, producing collected light 34. Collected light 34 is spectrally dispersed by prism 36 and is imaged by imaging lens 40 onto pixelated detector 44, also as discussed above. By excluding light other than that from object 24 from reaching pixelated detector 44, the detector produces an output signal that corresponds only to the actual images of an encoded bead, and the signal is not affected by the extraneous light that has been excluded. If not excluded in this manner, ambient light reaching pixelated detector 44 might otherwise produce "noise" in the output signal from the pixelated detector.

It should be noted that in the illustration of each of the imaging systems in FIGS. 2A and 2C, a light source has not been shown. These first two embodiments have been illustrated in their most general form to make clear that a separate light source is not required to produce an image of an encoded bead if the object is luminescent, i.e., if the object produces light. However, in most uses of the imaging apparatus for imaging beads, one or more light source(s) will be used to provide light that is incident on the bead being imaged. The location of the light sources substantially affects the interaction of the incident light with the bead (or other object) and the kind of information that can be obtained from the images on the pixelated detector.

Figure 3:
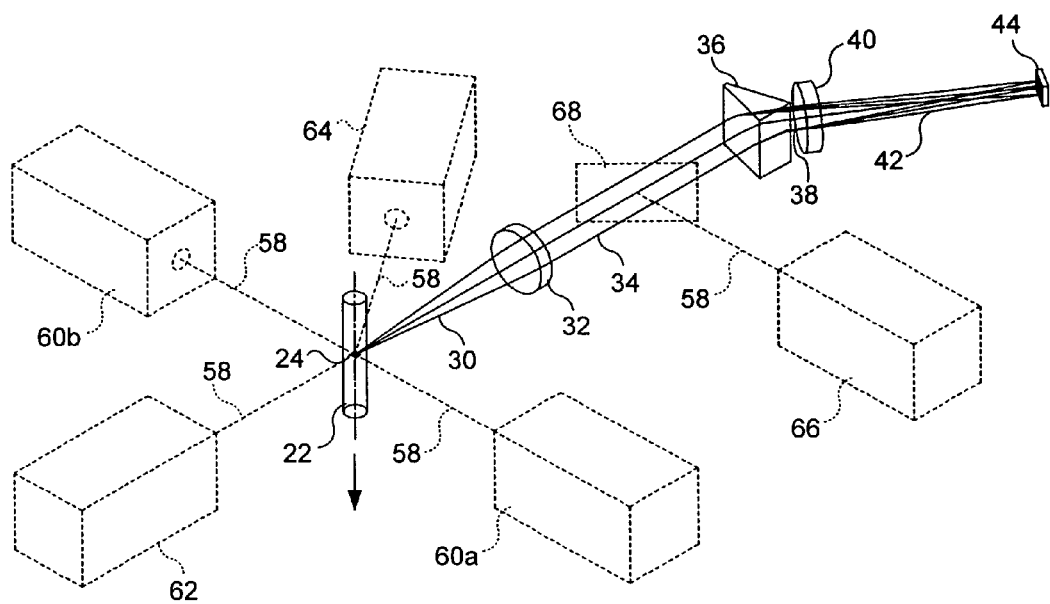
FIG. 3 is an isometric view of the imaging apparatus in FIG. 2A, showing different locations for one or more light source(s)

In FIG. 3, several different locations of light sources usable to provide light incident on bead 24 are illustrated. It should be understood, however, that light sources can be located at many other positions besides those shown in FIG. 3. The location of each light source that is employed will be dependent upon the kind of imaging of the bead, and the kind of data for the bead, to be derived from the signal produced by the pixelated detector. For example, employing a light source 60a or a light source 60b, as shown in the figure, will provide light 58 that is incident on bead 24 and which is scattered from the bead into the optical axis of collection lens 32. The optical axis of collection lens 32 is at about a 90° angle relative to the directions of the light incident upon bead 24 from either light source 60a or 60b. In contrast, a light source 62 is disposed so that light 58 emitted from that source travels toward the bead in a direction that is generally aligned with the optical axis of collection lens 32, so that the image formed on detector 44 will not include light absorbed by bead 24. Light absorption characteristics of the bead can thus be determined by illuminating the bead using light source 62.

A light source 64 is disposed to illuminate bead 24 with light directed toward the bead along a path that is approximately 30-45° off the optical axis of collection lens 32. This light 58, when incident on bead 24, will be reflected (scattered) from bead 24, and the reflected or scattered light will be imaged on detector 44. A more directly reflected light is provided by an epi light source 66, disposed so as to direct its light 58 toward a partially reflective surface 68 that is disposed so that a portion of the light is reflected through collection lens 32 and onto bead 24. The light reaching the bead will be reflected from it back along the axis of collection lens 32 and will at least in part pass through partially reflective surface 68 to form an image of the bead on pixelated detector 44. Alternatively, a dichroic mirror may be employed instead of, and in the position of, partially reflective surface 68 to direct light from epi light source 66 to excite fluorescence or other stimulated emission from bead 24. Light emitted from bead 24 at a different wavelength than the light source is then at least partially collected by collection lens 32 and passes through the dichroic mirror for spectral dispersion and detection by the detector.

Each of the light sources illustrated in FIG. 3 produce light 58, which can either be coherent, noncoherent, broadband, or narrowband light, depending upon the application of the imaging system for imaging beads. Thus, a tungsten filament light source can be used for applications in which a narrowband light source is not required. For applications such as stimulating the emission of fluorescence from reporters, narrowband light is preferred, since it also enables a spectrally-decomposed, nondistorted image of the bead to be produced from light scattered by the bead. This scattered light image will be separately resolved from the reporters produced on pixelated detector 44, so long as the emission spectra of any reporters are at different wavelengths than the wavelength of the light. The light source can be either of the continuous wave (CW) or pulsed type. If a pulsed type illumination source is employed, the extended integration period associated with pixelated detection can allow the integration of signal from multiple pulses. Furthermore, it is not necessary for the light to be pulsed in synchronization with the pixelated detector.

FIG. 4 illustrates an arrangement that enables the imaging of a bead from two different directions, in order to distinguish features that would otherwise overlap when viewed from a single direction. A stereoscopic imaging system 70 in FIG. 4 includes two pixelated detectors 44a and 44b, and their associated optical components, as discussed above in connection with the imaging system of FIG. 2A.

By positioning the optical axes of collection lenses 32 for the two pixelated detectors so that they are spaced apart, for example, by 90°, it is possible to separately resolve the signature of reporter tags imaged from two or more reporters on at least one of pixelated detectors 44a or 44b. If two or more reporters overlap in regard to the image produced on one of the detectors, they will be separately resolved in spectrally dispersed image produced on the other pixelated detector. Further, the use of two pixelated detectors in imaging system 70 in what might be referred to as a "stereo or three-dimensional configuration" allows flexibility in the configuration of each leg of the system, including parameters such as the relative pixelated readout rates, axial orientations, inclinations, focal plane positions, and magnification. Multiple beads or other objects may be imaged onto each detector simultaneously in the vertical direction. Since the beads may move in synchronicity with the signal on the pixelated detector, no gate or shutter is required to prevent blurring of the image. As previously noted, the present invention can use a pulsed or CW light source without need for a trigger mechanism to time a pulse coincident with particle arrival in the FOV.

Also illustrated in FIG. 4 are several exemplary positions for light sources, which are useful for different purposes in connection with the imaging system illustrated therein. In connection with pixelated detector 44a, light source 62 provides illumination of bead 24 from a direction so that absorption characteristics of the bead can be determined from the image produced on the pixelated detector. At the same time, light provided by light source 62 that is scattered from bead 24 can be used to produce a scatter image and spectrally dispersed images on pixelated detector 44b. A light source 74 can be employed to produce spectrally dispersed and scattered images on both pixelated detectors 44a and 44b. If light sources 62 and 72 are of different wavelengths and an appropriate filter is provided to block the wavelength from the light source aligned with the optical axis of the respective collections lenses 32, these two light sources can be used for producing scattered light from the bead. For example, suppose light source 72 produces light of a wavelength A that scatters from bead 24 and is directed toward pixelated detector 44a. By including a filter (not shown) that blocks wavelength B produced by light source 62, the light at wavelength B will not directly affect the images produced on pixelated detector 44a. Similarly, the light from light source 72 would be blocked with an appropriate filter (not shown), so that it does not interfere with the imaging of light produced by light source 62 that is scattered from bead 24 onto pixelated detector 44b.

Epi light source 66 is also illustrated for use in producing images on pixelated detector 44a in conjunction with partial reflector 68. Light source 64 can be used to generate reflected light to produce images on pixelated detector 44a, while scattered light from this source is directed toward pixelated detector 44b. These and other possible locations of light sources will be apparent to those of ordinary skill in the art, as appropriate, for providing the incident light on the bead needed to achieve imaging, depending upon the particular application and information about the bead that is desired.

Figure 5:
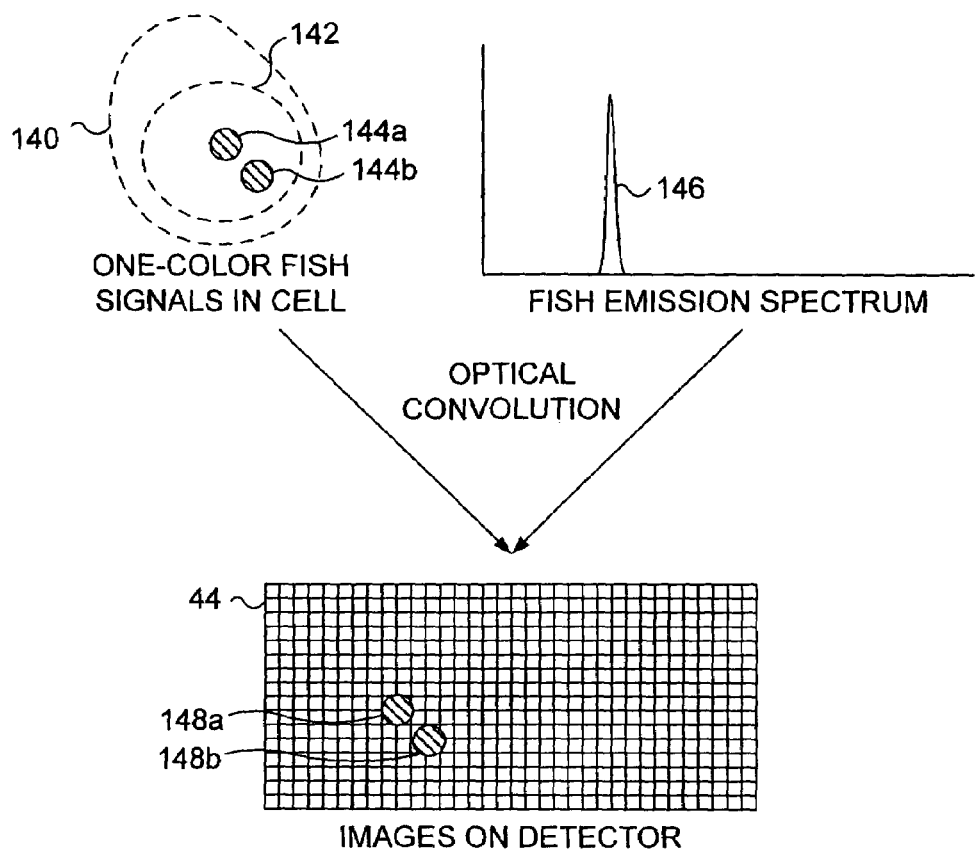
FIG. 5 is a schematic diagram illustrating the optical convolution of a narrow fluorescence in situ hybridization (FISH) emission spectrum by the present invention, to resolve two FISH probes in a cell.

FIG. 5 illustrates a detector used in the present invention, with a spectral resolution of approximately 10 nm per pixel and a spatial resolution of approximately 0.5 microns. In the following discussion of FIGS. 5-8, the operation of the imaging system is directed toward the identification of fluorescence in situ hybridization (FISH) probes bound to specific DNA with cells. However, those skilled in the art will appreciate that the same method and apparatus applies to the spectral and spatial information resulting from the imaging of reporters associated with beads. With respect to the following discussion, a cell and nucleus can be considered to be equivalent to a bead, and FISH probes can be considered to be equivalent to reporters associated with or bound to a bead.

FIG. 5 illustrates how the imaging system that is usable to image reporter beads is used to image a cell 140 having a nucleus 142 in which are disposed two FISH probes 144a and 144b having the same emission spectrum. As noted above, in a bead analysis, the FISH spots may be considered analogous to reporters. In FIG. 5, the emission spectrum 146 of FISH probes 144a and 144b is approximately 10 nm in width, such as would be produced by "quantum dots" or a narrowband fluorescent dye. The optical convolution of the narrow bandwidth spectrum results in minimal blurring of FISH spots 148a and 148b, enabling them to be readily resolved on detector 44.

Figure 6:
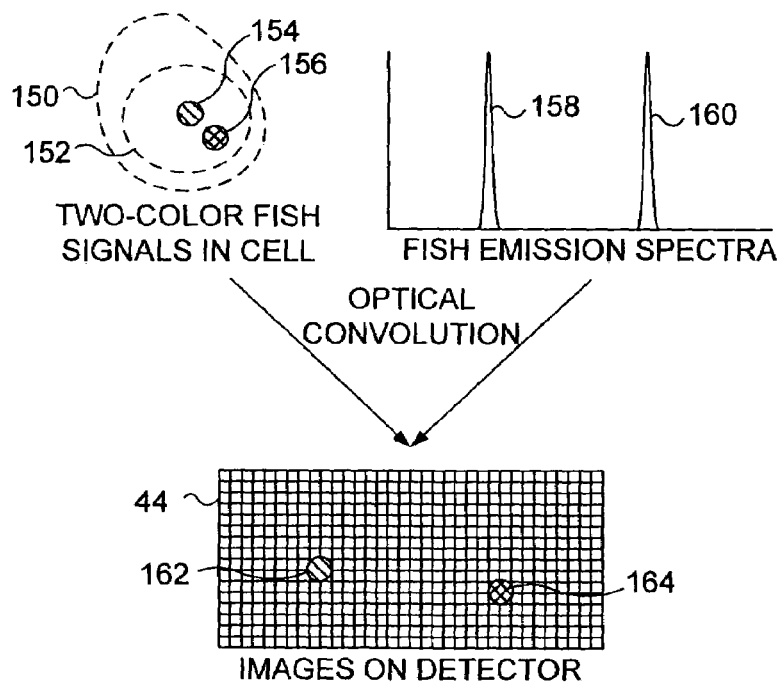
FIG. 6 is a schematic diagram showing the optical convolution of two different colors of narrow FISH emission spectra, to resolve the image of the FISH probes on the TDI detector.
Figure 10:
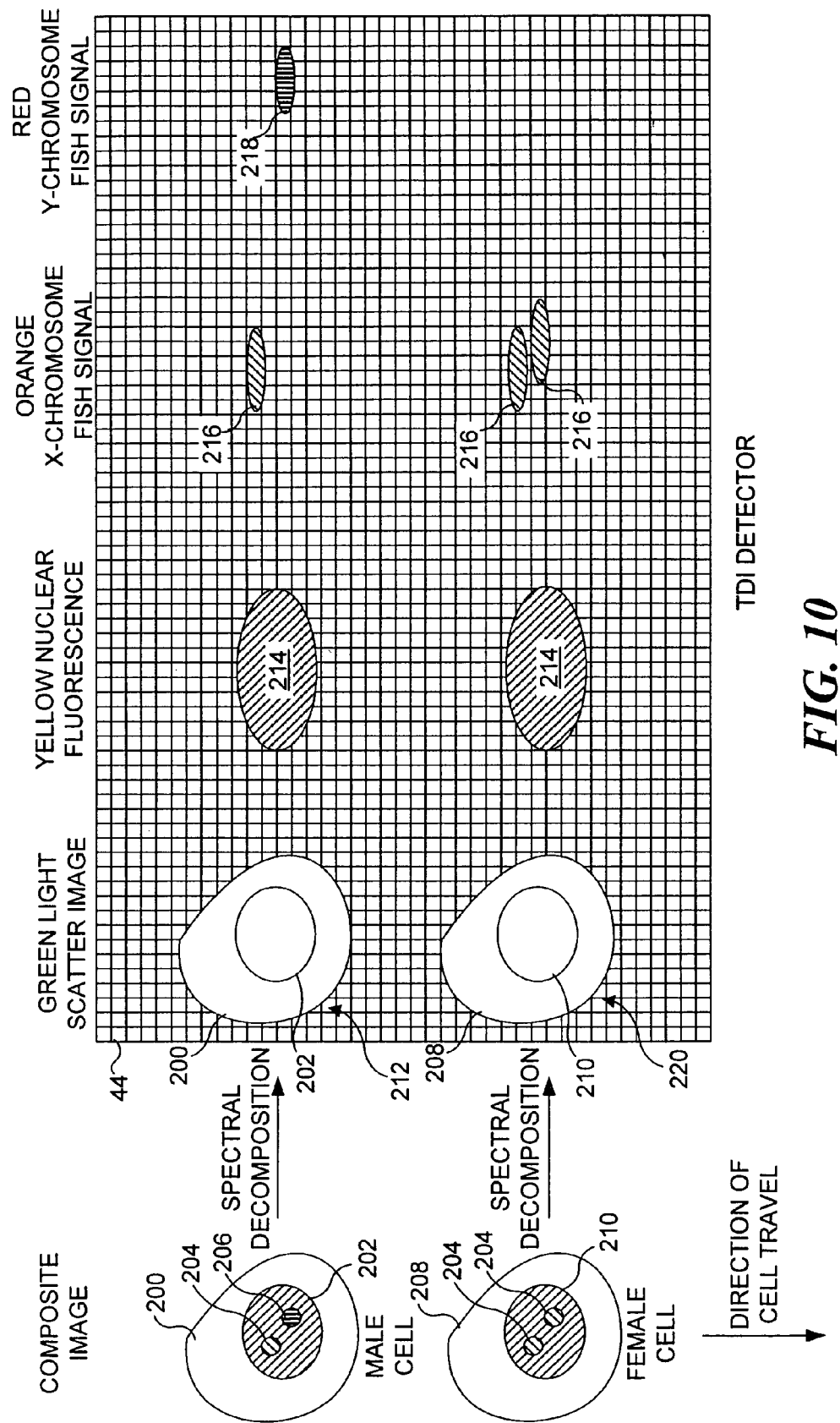
FIG. 10 is a schematic diagram illustrating how an imaging system in accord with the present invention is used to determine whether a cell is from a male or female.

In FIG. 6, a cell 150 is illustrated having a nucleus 152 in which are disposed FISH probes 154 and 156 having different emission spectra. Each of the emission spectra of FISH probes 154 and 156 are relatively narrow, such as the emission spectra from quantum dots, as indicated by wavebands 158 and 160, and therefore, as in FIG. 5, minimal blurring occurs in FISH spots 162 and 164. Furthermore, the spectral dispersion of the present invention, which maps wavelength into lateral position on TDI detector 44, produces a relatively wide physical displacement of FISH spots 162 and 164, despite the close proximity of FISH probes 154 and 156 in the cell. Taken together, FIGS. 5 and 6 illustrate how the present invention discriminates FISH probes of the same or different color, thereby enabling the simultaneous enumeration of numerous genetic traits. FIG. 10 illustrates how a cell and FISH spots contained therein will be imaged by the present invention upon a pixelated detector.

Figure 7:
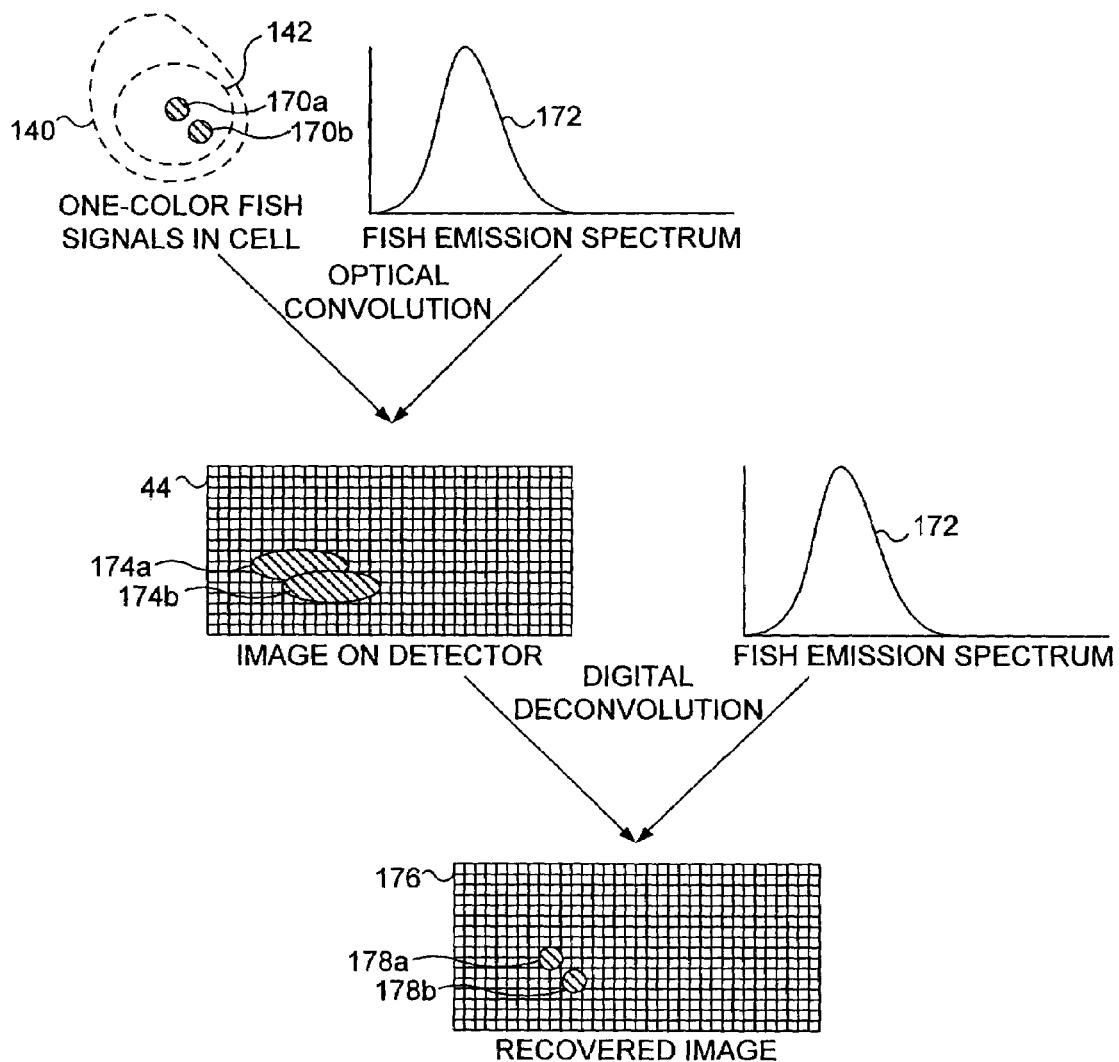
FIG. 7 is a schematic diagram illustrating how for a wider FISH emission spectrum, a deconvolution is provided to resolve the image of two FISH probes of a single color.
Figure 8:
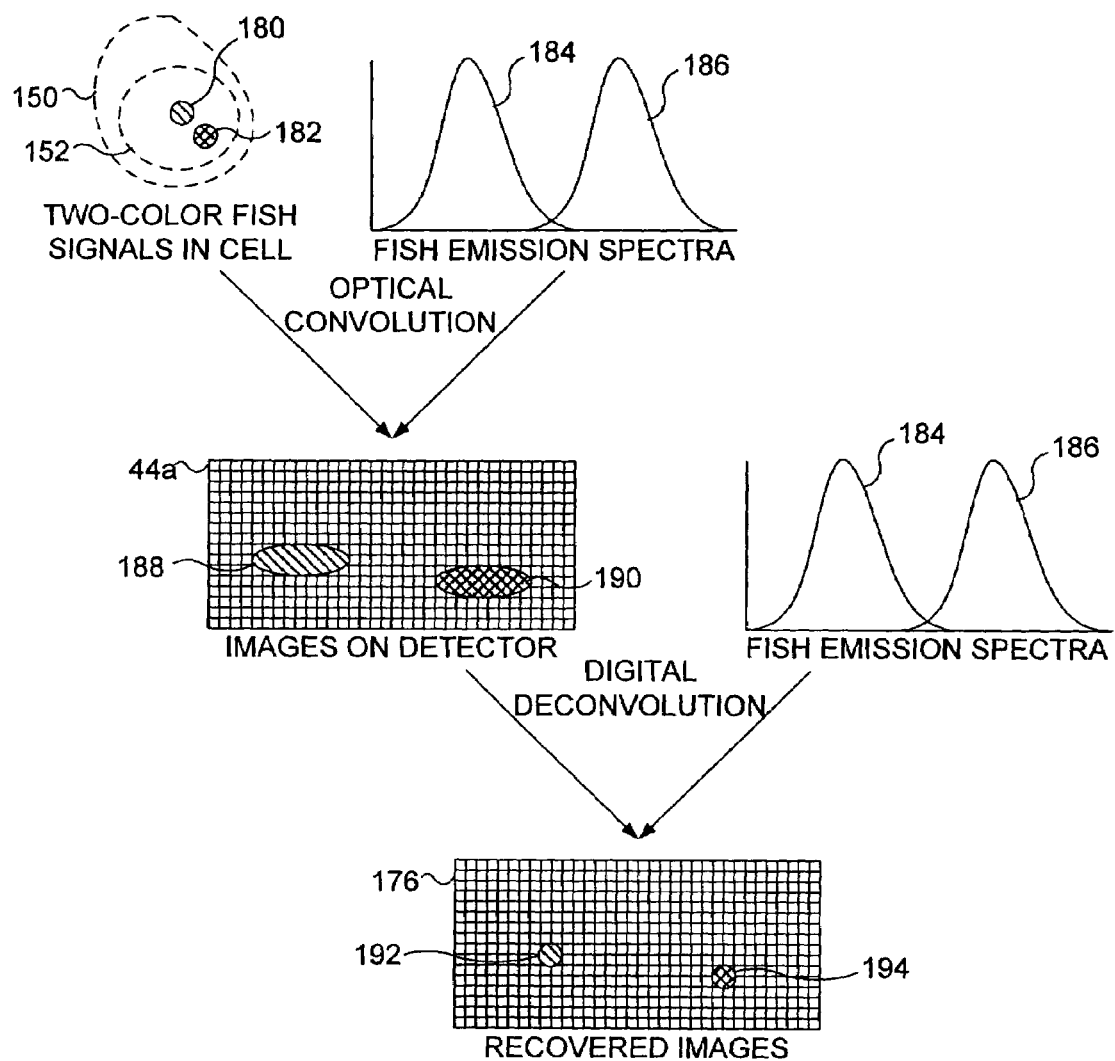
FIG. 8 is a schematic diagram showing the deconvolution of two color FISH spectra that are relatively wide, to resolve the image of the FISH probes.

FIGS. 7 and 8 illustrate that the present invention can also be used with light of wider spectral bandwidth. In this case, an additional signal processing step is performed to correct for lateral blurring due to the wide emission spectra. Note that this involves a deconvolution step which requires the use of a pixelated detector that is a TDI detector. In FIG. 7, a cell 140 having a nucleus 142 is shown, and FISH probes 170a and 170b having a common emission spectrum are disposed in the nucleus. FISH probes 170a and 170b are characterized by producing a relatively wide emission spectrum 172. When optically convolved by the spectral dispersion provided by the present invention, FISH spots 174a and 174b are produced on a TDI detector 44a, but their images are laterally blurred across pixelated detector 44, as a result of their relatively wide emission spectrum. To more clearly, resolve the separation of FISH spots probes 174a and 174b, a deconvolution is carried out on the signal produced by TDI detector 44a, with the known FISH emission spectrum, thereby producing accurate FISH spot representations 178a and 178b on a display 176. The deconvolution step enhances the ability to enumerate the number of FISH spots. Note that the deconvolution step requires the use of a pixelated detector that is a TDI detector.

FIG. 8 illustrates a corresponding relationship between FISH probes 180 and 182, which are disposed within a nucleus 152 of a cell 150. FISH probes 180 and 182 are characterized by each producing relatively wide band emission spectra 184 and 186, as shown in the Figure. Optical convolution of the fluorescence emitted by the FISH probes, which are spectrally dispersed, produces FISH spots 188 and 190 on TDI detector 44. Again, by deconvolving the known FISH emission spectra with the signal produced by TDI detector 44, the corresponding images shown on display 176 of FISH spots 192 and 194 are recovered. Again, the spectral dispersion of the present invention, which maps wavelength into lateral position on TDI detector 44, produces a relatively wide physical displacement of FISH spots 192 and 194, despite the close proximity of FISH probes 180 and 182 in the cell. In this manner, it is possible to resolve these images of FISH spots produced by FISH probes having different and relatively wide emission spectra.

Figure 9:
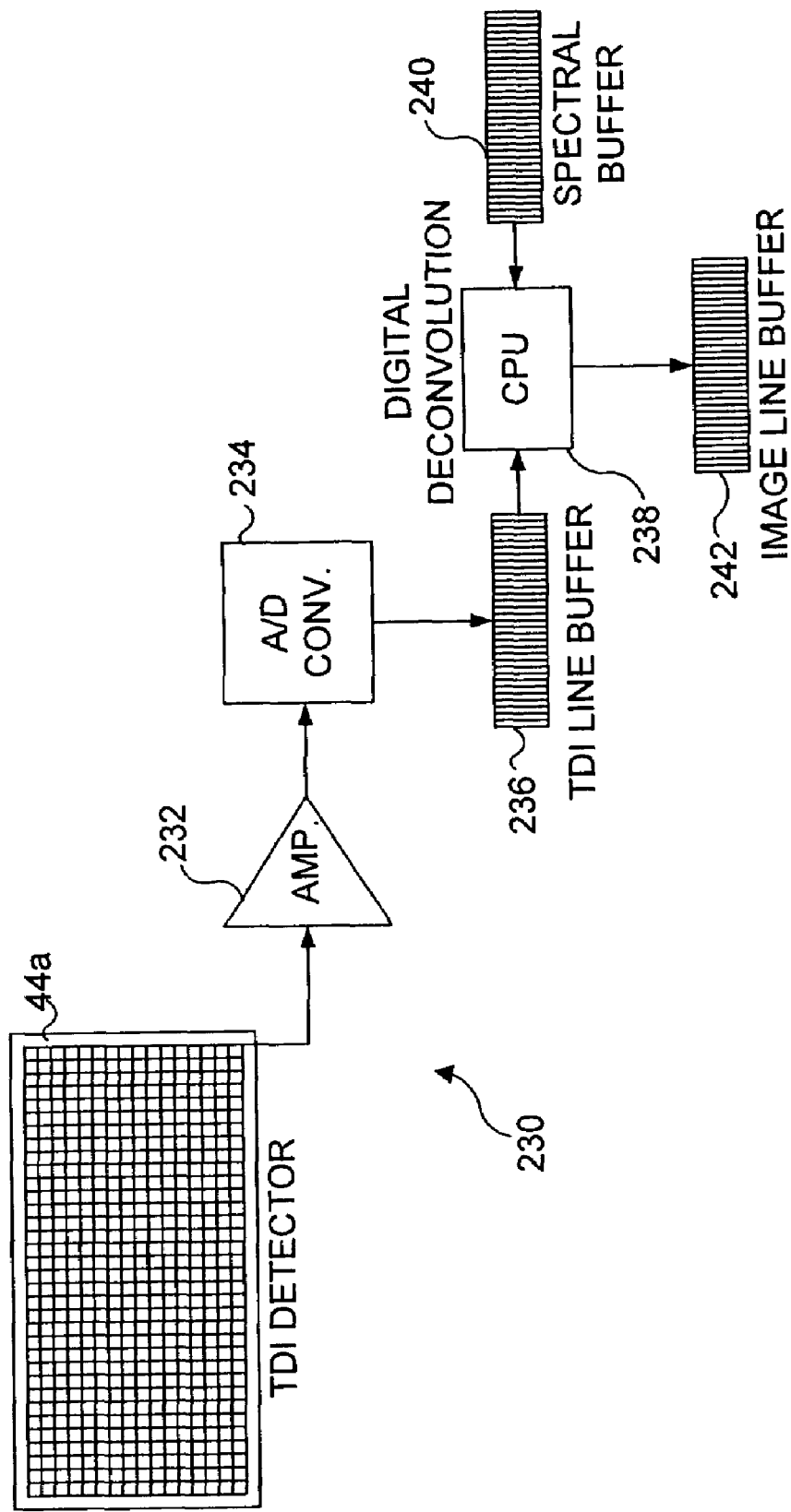
FIG. 9 is a schematic block diagram of the system used to process the signal produced by a TDI detector in the present invention.

A system 230 for analyzing the signal produced by TDI detector 44a and performing the deconvolution steps described above is illustrated in FIG. 9. In this figure, the signal from TDI detector 44a is applied to an amplifier 232, which buffers the signal and amplifies it to achieve a level required by an analog-to-digital (A/D) converter 234. This A/D converter converts the analog signal from amplifier 232 into a digital signal that is input into a line buffer 236. Line buffer 236 temporarily stores the digital signal until it can be processed by a CPU 238. To carry out the deconvolution noted above, a spectral buffer 240 is loaded with the known emission spectrum for each of the FISH probes being used so that their emission spectra can be deconvolved with the signal stored in line buffer 236. CPU 238 is a high speed processor programmed to carry out the deconvolution and other analysis procedures, enabling the identification of desired characteristics or parameters of the object being imaged. The output from CPU 238 is temporarily stored in an image line buffer 242 that enables the image to be displayed or otherwise recorded for later analysis.

FIG. 10 illustrates a practical application of the above described systems for identifying a male cell 200 and a female cell 208 and for producing their corresponding scatter images 212 and 220. Male cell 200 includes a nucleus 202 that has been stained with a yellow fluorescent dye. In addition, a FISH probe 204 produces a fluorescent orange emission, indicating the presence of an X-chromosome in the nucleus, while a FISH probe 206 produces red fluorescence emission, indicating the presence of a Y-chromosome. Spectral decomposition of the fluorescence emissions from male cell 200, when the cell is illuminated with light from a green light source, results in a series of images on TDI detector 44, separated as a function of the wavelength of the light that is imaged. Green light that is incident on the cells has a narrow waveband, and image 212 of male cell 200 produced by green light scatter is only slightly convoluted by the spectral decomposition process. Green light scatter image 212 of cell 200 and its nucleus 202 appear on the left side of the TDI detector, while a fluorescent spot 214 corresponding to the yellow fluorescence emitted by nucleus 202 appears in the next few columns on the TDI detector. Furthermore, as a function of the different wavelengths of the fluorescence emitted by FISH probes 204 and 206, FISH spots 216 and 218 appear at locations spaced apart on the detector, but slightly blurred across the columns of TDI detector 44 due to the widths of their respective emission spectra. By analyzing the signals produced by the TDI detector, the FISH probes responsive to X and Y chromosomes are detected, enabling the user to determine that cell 200 is a male cell, since it includes both the X and Y chromosome. Similarly, female cell 208, when spectrally decomposed, also includes the characteristic yellow fluorescence of nucleus 210, but unlike the male cell, includes two FISH spots 216 corresponding to FISH probes 204, which indicates the presence of two X-chromosomes. Because TDI detector 44 also distinguishes the spatial position of male cell 200 and female cell 208, the corresponding spectral decompositions for these cells are readily separately resolved as both cells pass through the imaging system in the direction indicated by the arrow to the lower left of FIG. 10. Again, it should be noted that a deconvolution can be applied to the signal produced by TDI detector 44 to provide better resolution of the corresponding FISH spots that are illustrated.

Again, to avoid any confusion, those skilled in the art will appreciate that in the present invention, which is employed for the analysis of reporter labeled beads, a bead in analogous to the cell and a reporter is analogous to a FISH spot, in regard to the discussion of FISH spots contained herein. One difference is that a FISH spot is typically constructed with a single fluorochrome and therefore emits over a single spectral range, as will be evident in the Figures. In the case of reporters, each reporter may be constructed of more than one fluorochrome and therefore, can emit several spectra simultaneously. The same signal processing techniques disclosed in the above-referenced U.S. Pat. No. 6,211,955 and discussed relative to objects and FISH spots can be applied to enumerate unique reporters of more than one fluorochrome associated with, or bound to a bead. Therefore, it will be understood that the imaging system and techniques used for analysis may be used to enumerate unique reporters associated with or bound to a bead in order identify the unique spectral signature of the bead.

Figure 17:
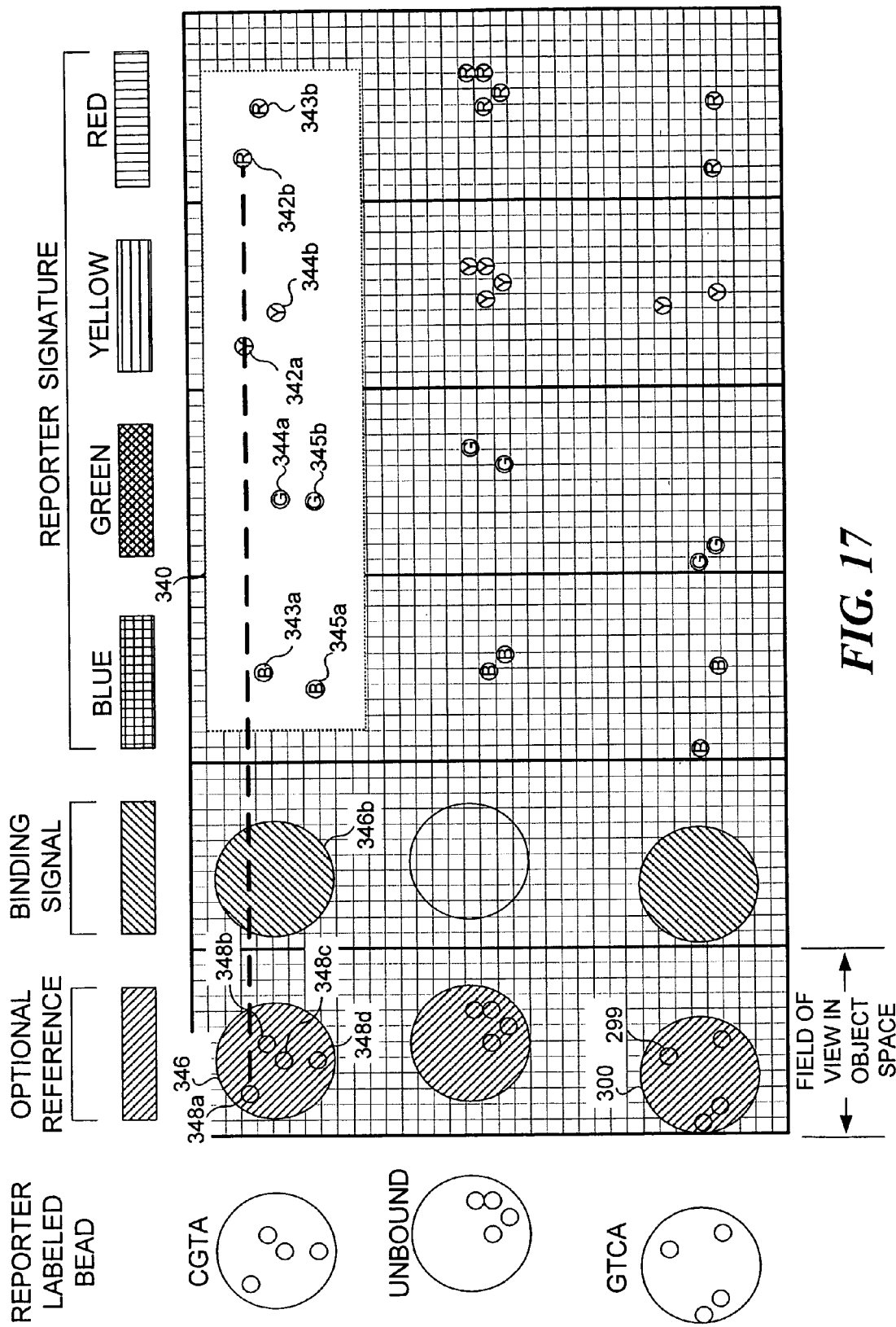
FIG. 17 illustrates images that are projected onto a detector for the spectral decomposition embodiment when three beads are in view.

FIG. 17 illustrates the results of processing the images on the detector in a reporter labeled bead scenario, wherein the emission spectra from each reporter has been deconvolved. FIG. 17, which is discussed in greater detail below, is also used to illustrate the use of the non-convolving spectral decomposition and imaging system discussed in the next section.

Second and Third Embodiments of Apparatus for Spectral Decomposition and Imaging In the second embodiment of apparatus usable in practicing the present invention, a spectral dispersing component having characteristics that ensure no distortion or convolution of the image occurs due to the emission bandwidth is employed, and as a result, a deconvolution step is not needed to process the image data. FIG. 11 illustrates this second preferred embodiment. Unlike a prism, where every wavelength leaves the prism at a different angle, all light within a predefined bandwidth incident on the dichroic beam splitter at a common angle leaves the dichroic beam splitter at the same angle. Consequently, there is no convolution between the emission spectrum of the light leaving the bead and the image of that bead. When using such a spectral dispersing component, light of a first spectral bandwidth is reflected from the first dichroic beam splitter at a predefined nominal angle. Light of a second spectral bandwidth is passed through the first dichroic beam splitter to the next dichroic beam splitter and is reflected therefrom at a different predefined nominal angle. Light of a third spectral bandwidth is passed through the first and second dichroic beam splitters to a third dichroic beam splitter and reflected therefrom at a third predefined nominal angle. The dichroic beam splitters are selected to cover the desired light spectrum with the appropriate spectral passbands. In FIG. 11 illustrates a five-color stacked wedge spectral dispersing filter assembly 252. This second embodiment is substantially similar to the embodiment shown in FIGS. 2 and 3, except that spectral dispersing prism element 36 (of FIGS. 2 and 3) is replaced by spectral dispersing filter assembly 252. The spectral dispersing filter assembly splits the light into a plurality of light beams having different bandwidths. Each light beam thus produced is directed at a different nominal angle so as to fall upon a different region of detector 44. The nominal angular separation between each bandwidth produced by the spectral dispersing filter assembly 252 exceeds the field angle of the imaging system in object space thereby preventing overlap of the field images of various bandwidths on the detector.

Figure 12:
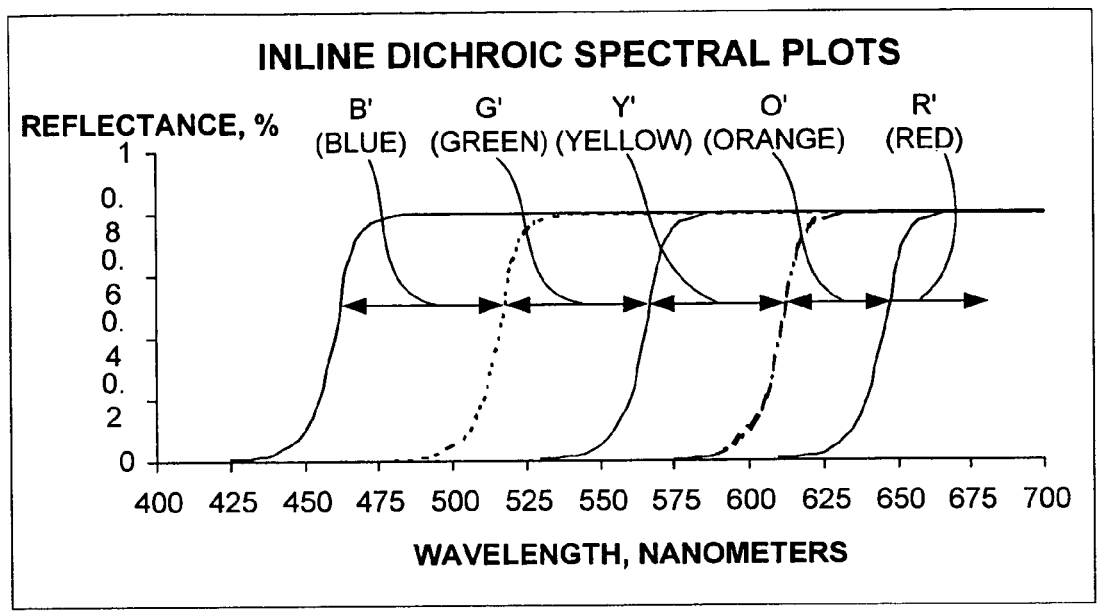
FIG. 12 is an X-Y plot of several typical passbands for the dichroic filters employed in the embodiment shown in FIG. 11.

Spectral dispersing filter assembly 252 comprises a plurality of stacked dichroic wedge filters, including a red dichroic filter R, an orange dichroic filter O, a yellow dichroic filter Y, a green dichroic filter G, and a blue dichroic filter B. Red dichroic filter R is placed in the path of collected light 34, oriented at an angle of approximately 44.0° relative to an optic axis 253 of collection lenses 32 and 32. Light of red wavelengths and above, i.e., >640 nm, is reflected from the surface of red dichroic filter R at a nominal angle of 1°, measured counter-clockwise from a vertical optic axis 257. Example spectral reflectance characteristics R' of red dichroic filter R are plotted in FIG. 12, along with example spectral reflectance characteristics corresponding to the other dichroic filters used in spectral dispersing filter assembly 252. In FIG. 12, O' indicates the spectral reflectance characteristics of orange dichroic filter O, Y' indicates the spectral reflectance characteristics of yellow dichroic filter Y, etc. The light reflected by red dichroic filter R leaves spectral dispersing filter assembly 252 and passes through imaging lenses 40a and 40*b*, which cause the light to be imaged onto a red light receiving region of TDI detector 44, which is disposed toward the right end of the TDI detector, as shown in FIG. 11.

Orange dichroic filter O is disposed a short distance behind red dichroic filter R and is oriented at an angle of 44.5 degrees with respect to optic axis 253. Light of orange wavelengths and greater, i.e., >610 nm, is reflected by orange dichroic filter O at a nominal angle of 0.5° with respect to vertical optic axis 257. Because the portion of collected light 34 comprising wavelengths longer than 640 nm was already reflected by red dichroic filter R, the light reflected from the surface of orange dichroic filter O is effectively bandpassed in the orange colored region between 610 nm and 640 nm. This light travels at a nominal angle of 0.5° from vertical optic axis 257, and is imaged by imaging lenses 40*a* and 40*b* so as to fall onto an orange light receiving region disposed toward the right-hand side of TDI detector 44 between a center region of the TDI detector and the red light receiving region.

Yellow dichroic filter Y is disposed a short distance behind orange dichroic filter O and is oriented at an angle of 45° with respect to optic axis 253. Light of yellow wavelengths, i.e., 560 nm and longer, is reflected from yellow dichroic filter Y at a nominal angle of 0.0° with respect to vertical optic axis 257. Wavelengths of light reflected by yellow dichroic filter Y are effectively bandpassed in the yellow region between 560 nm and 610 nm and are imaged by imaging lenses 40*a* and 40*b* near vertical optic axis 257 so as to fall on a yellow light receiving region toward the center of TDI detector 44.

In a manner similar to dichroic filters R, O, and Y, dichroic filters G and B are configured and oriented so as to image green and blue light wavebands onto respective green and blue light receiving regions of TDI detector 44, which are disposed toward the left-hand side of the TDI detector. By stacking the dichroic filters at different predefined angles, spectral dispersing filter assembly 252 collectively works to focus light within predefined wavebands of the light spectrum onto predefined regions of TDI detector 44. Those of ordinary skill in the art will appreciate that the filters used in the spectral dispersing filter assembly 252 may have spectral characteristics that differ from those described above and in FIG. 12. Further, the spectral characteristics may be arbitrary and not limited to dichroic in order to achieve the desired dispersion characteristics.

The wedge shape of the dichroic filters in the preceding discussion allows the filters to be placed in near contact, in contact, or possibly cemented together to form the spectral dispersing filter assembly 252. The angle of the wedge shape fabricated into the substrate for the dichroic filter allows easy assembly of the spectral dispersing filter assembly 252, forming a monolithic structure in which the wedge-shaped substrate is sandwiched between adjacent dichroic filters. If the filters are in contact with each other or cemented together, the composition of the materials that determine the spectral performance of the filter may be different from those which are not in contact. Those of ordinary skill in the art will appreciate that flat, non wedge-shaped substrates could be used to fabricate the spectral dispersing filter assembly 252. In this case another means such as mechanically mounting the filters could be used to maintain the angular relationships between the filters.

Figure 13:
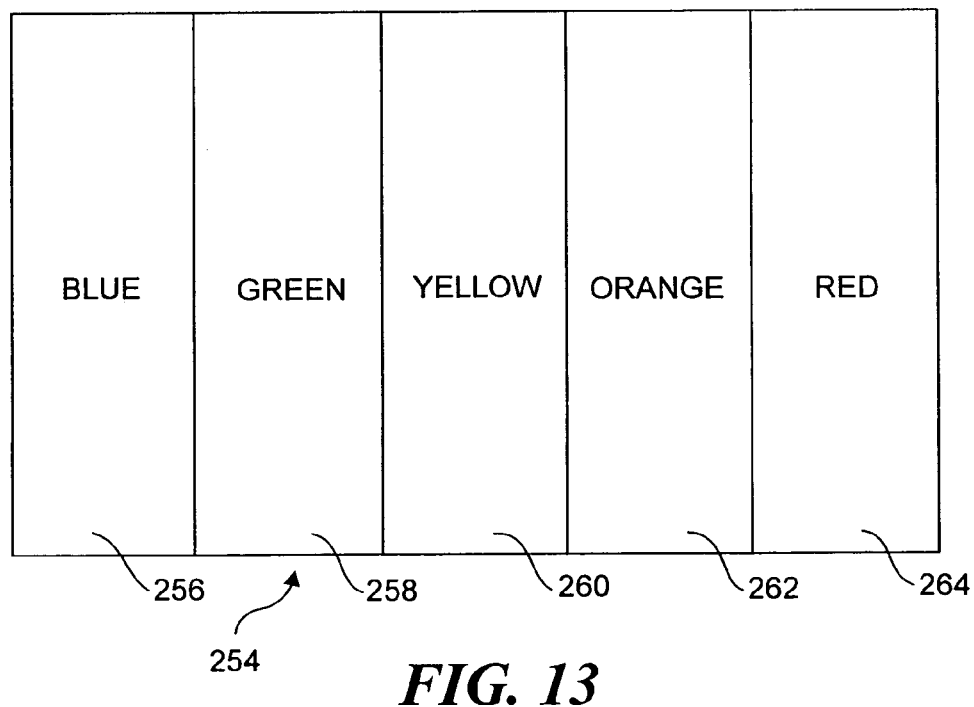
FIG. 13 is a schematic illustration of a detection filter assembly that may optionally be placed in front of the TDI detector in the embodiment of FIG. 11 to further suppress out-of-band light.
Figure 14A:
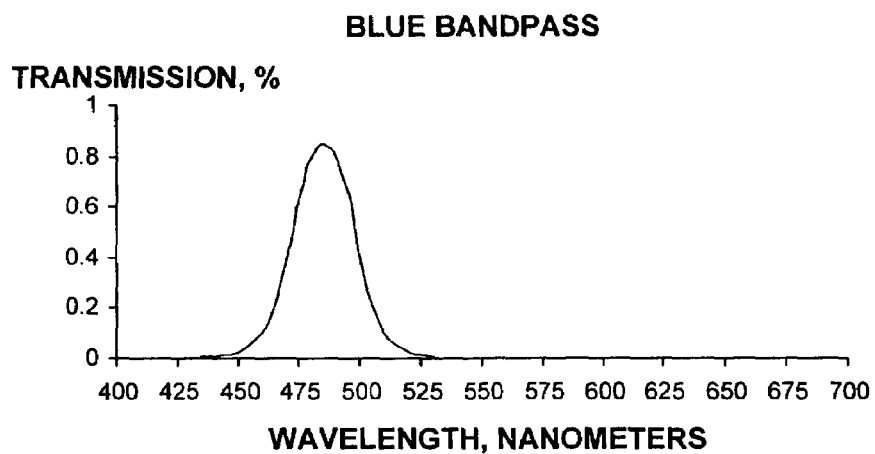
FIGS. 14A-14E are X-Y plots of transmission vs. wavelength corresponding to corresponding passbands of the filter segments of the detection filter assembly that may optionally be placed in front of the TDI detector.
Figure 14B:
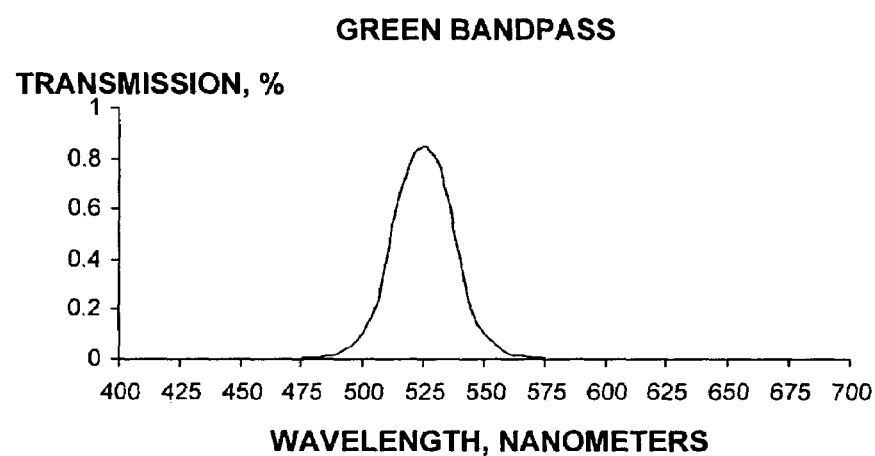
Figure 14C:
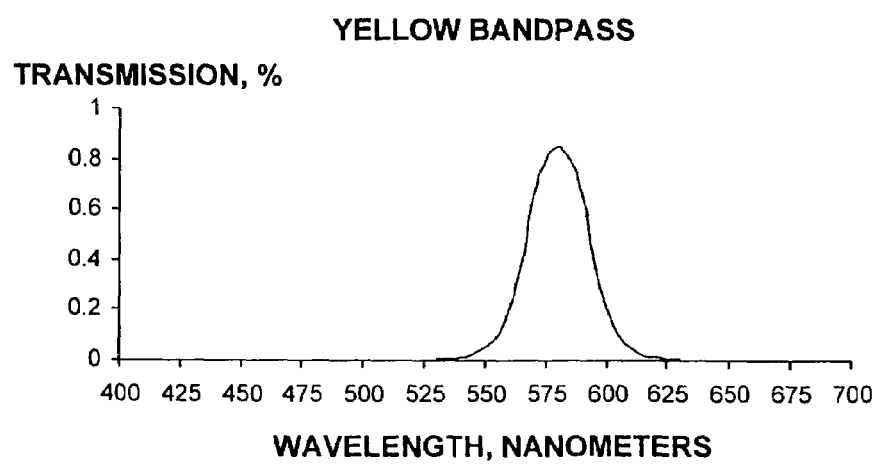
Figure 14D:
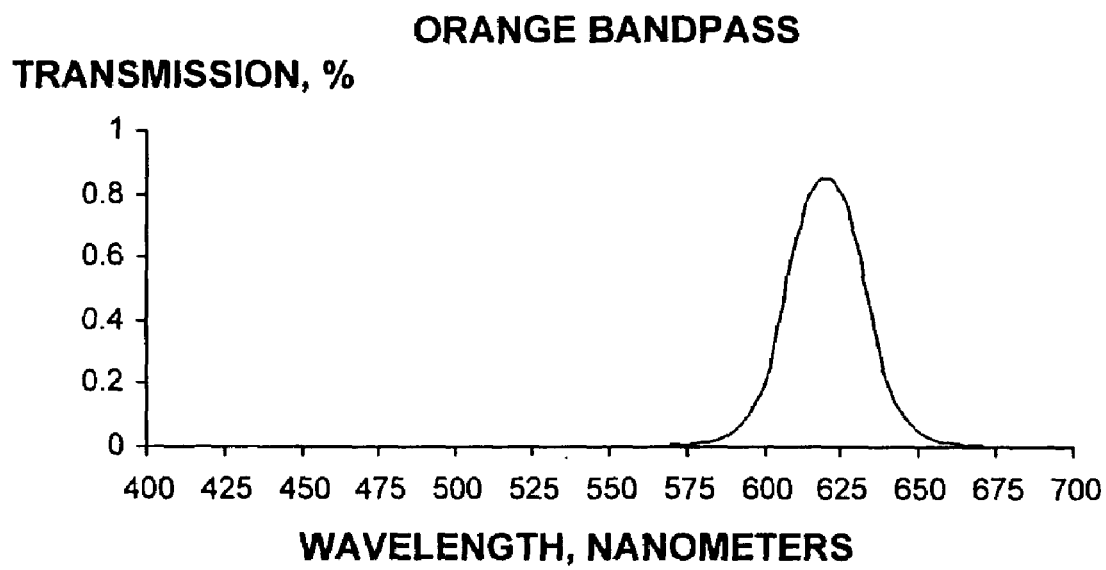
Figure 14E:
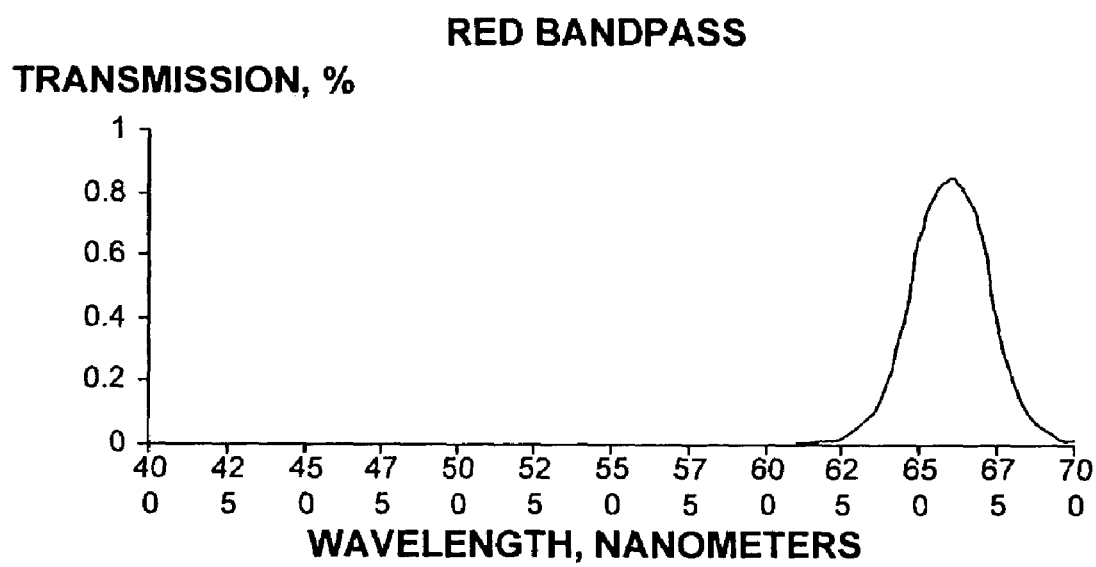

In addition to the foregoing configuration, non-distorting spectral dispersion system 250 may optionally include a detector filter assembly 254 to further attenuate undesired signals in each of the light beams, depending upon the amount of rejection required for out-of-band signals. FIG. 13 illustrates the construction of an exemplary detector filter 254 corresponding to the five color bands discussed above and includes a blue spectral region 256, a green spectral region 258, a yellow spectral region 260, an orange spectral region 262, and a red spectral region 264, all of which are disposed side-by-side, as shown in the Figure. The corresponding spectral characteristics of the blue, green, yellow, orange, and red spectral regions or wavebands are respectively shown in FIGS. 14A-14E. The detection filter assembly shown in FIG. 13 may be constructed by cementing separate filters in side-by-side arrangement on a common substrate or by other means well known to those or ordinary skill in the art. Additionally, the ordinary practitioner in the art will understand that the filter may alternatively be placed at an intermediate image plane, instead of directly in front of TDI detector 44.

Figure 15:
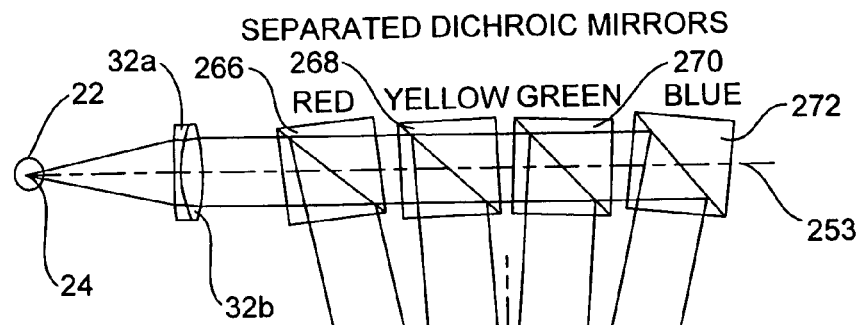
FIG. 15 is a plan view of another embodiment of the configuration of FIG. 11, wherein the spectral dispersion filter system comprises a plurality of dichroic cube filters orientated at various angles to create the spectral dispersing effect.
Figure 15:
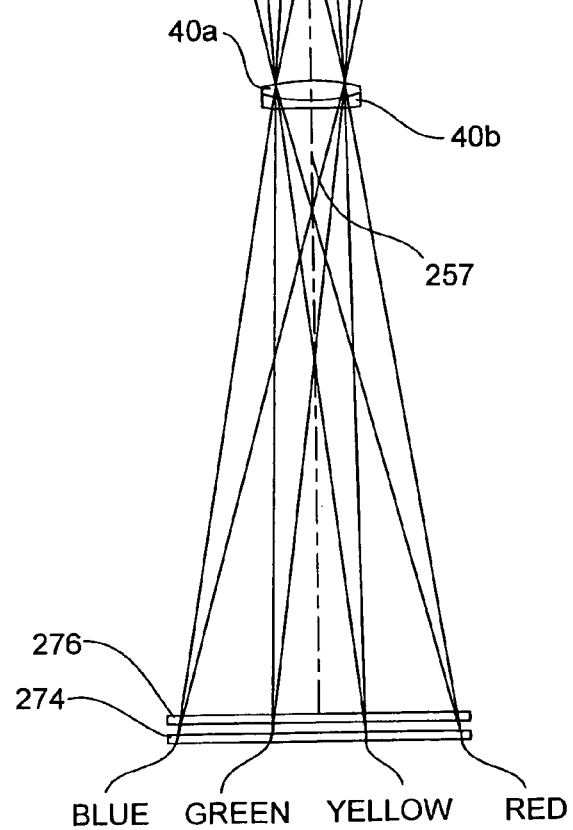

In the embodiment shown in FIG. 11, light may pass through each dichroic filter in the spectral dispersing filter assembly 252 twice before exiting the spectral dispersing filter assembly 252. This condition will further attenuate out-of-band signals, but will also attenuate in-band signals. FIG. 15 illustrates a third embodiment useful in the present invention in which the light does not pass through another dichroic filter after reflection. In this embodiment, a plurality of cube dichroic filters, including a red cube filter 266, a yellow cube filter 268, a green cube filter 270, and a blue cube filter 272 are spaced apart sufficiently to ensure that light does not pass through any of the cube filters more than once. As with the second embodiment of FIG. 11, the cube dichroic filters are oriented at appropriate angles to image light within a predefined bandwidth to distinct regions on a TDI detector 274. As the light is reflected from each of cube dichroic filters 266, 268, 270 and 272, it is directed toward imaging lenses 40*a* and 40*b*, and different bandpass portions of the light are focussed upon corresponding red, yellow, green, and blue light receiving segments or regions defined on a light receiving surface of TDI detector 274. If desired, an optional detector filter assembly 276 of similar construction to detector filter assembly 254 (but without the orange spectral region) may be used to increase the rejection of out-of-band signals. It should be apparent to those skilled in the art that separate spaced apart plates, or pellicle beam splitters could also be used in this application instead of the cube filters.

In the third embodiment illustrated in FIG. 15, the image lenses 40*a* and 40*b* must be placed a sufficient distance away from the plurality of cube filters to minimize the clear aperture requirement for lenses 40*a* and 40*b*. Those skilled in the art will appreciate the clear aperture in the plane orthogonal to the page can increase as the distance between the lenses and plurality cube filters increases. Therefore, the placement of lenses 40*a* and 40*b* must be chosen to appropriately accommodate the clear aperture in both planes.

The foregoing descriptions of the preceding non-convolving embodiments illustrate the use of four and five color systems. Those skilled in the art will appreciate that a spectral dispersing component with more or fewer filters may be used in these configurations in order to construct a system covering a wider or a narrower spectral region, or different passbands within a given spectral region. Likewise, those skilled in the art will appreciate that the spectral resolution of the present invention may be increased or decreased by appropriately choosing the number and spectral characteristics of the dichroic and or bandpass filters that are used. Furthermore, those skilled in the art will appreciate that the angles or orientation of the filters may be adjusted to direct light of a given bandwidth onto any desired point on the TDI detector. In addition, there is no need to focus the light in increasing or decreasing order by wavelength. For example, in fluorescence imaging applications, one may wish to create more spatial separation on the TDI detector between the excitation and emission wavelengths by changing the angles at which the filters corresponding to those wavelengths are oriented with respect to the optic axes of the system. Finally, it will be clear to those skilled in the art that dispersion of the collected light may be performed on the basis of nonspectral characteristics, including angle, position, polarization, phase, or other optical properties.

FIG. 17 illustrates the images projected onto a detector for the present spectral decomposition embodiment in the case where three beads are in view. In this illustration, each bead has a series of four unique reporters visible in which the reporters are constructed of up to four distinct fluorochromes. There is no spreading of the reporter images, as occurs in the prism based spectral decomposition embodiment. The field angle orthogonal to flow in object space is also indicated on FIG. 17. In this particular configuration, the field angle in object space is less than +/−0.25°. Those skilled in the art will appreciate that the field angle can be made larger or smaller. To the extent that the field angle is made larger, for example, to image cells over a wider region on a slide or in a broad flat flow, the field angle at the detector will increase in proportion to the number of colors used. Those skilled in the art will appreciate that broad flat flow can easily be created using commercially available flow cells as shown in FIG. 16B containing flow cell 290, with a cross section that is elongated in an axis perpendicular to both the flow and optical axes. The generation of broad flat flow is discussed in many references including U.S. Pat. No. 5,422,712.

Fourth Embodiment of Apparatus for Spectral Decomposition and Imaging

Figure 16A:
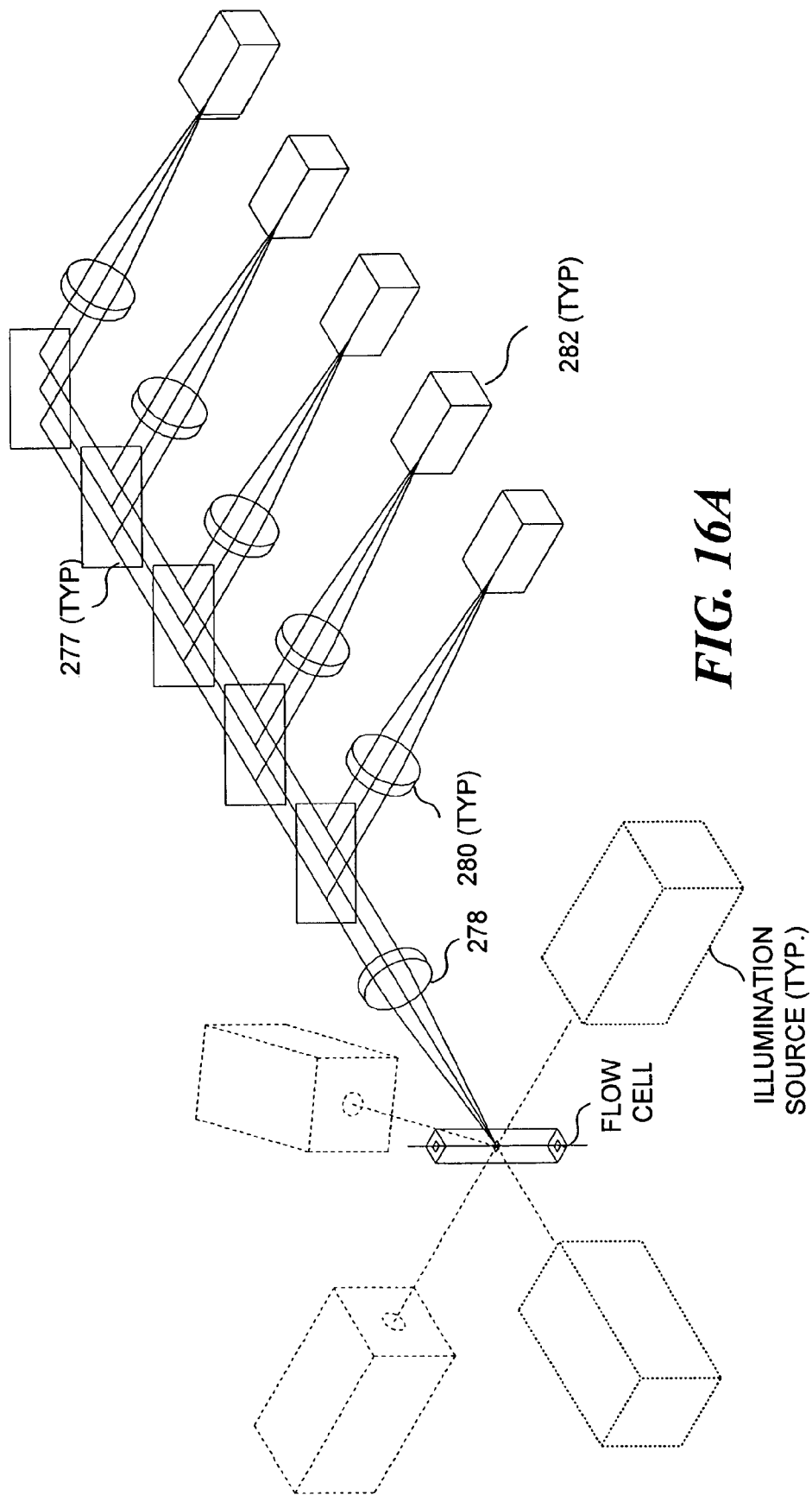
FIG. 16A illustrates another embodiment of the imaging system in accord with the present invention, in which the spectral emission is not convolved with the image and in which the spectral decomposition occurs in an axis perpendicular to flow through the use of separate dichroic filters, imaging lenses, and detectors for each spectral region.
Figure 16B:
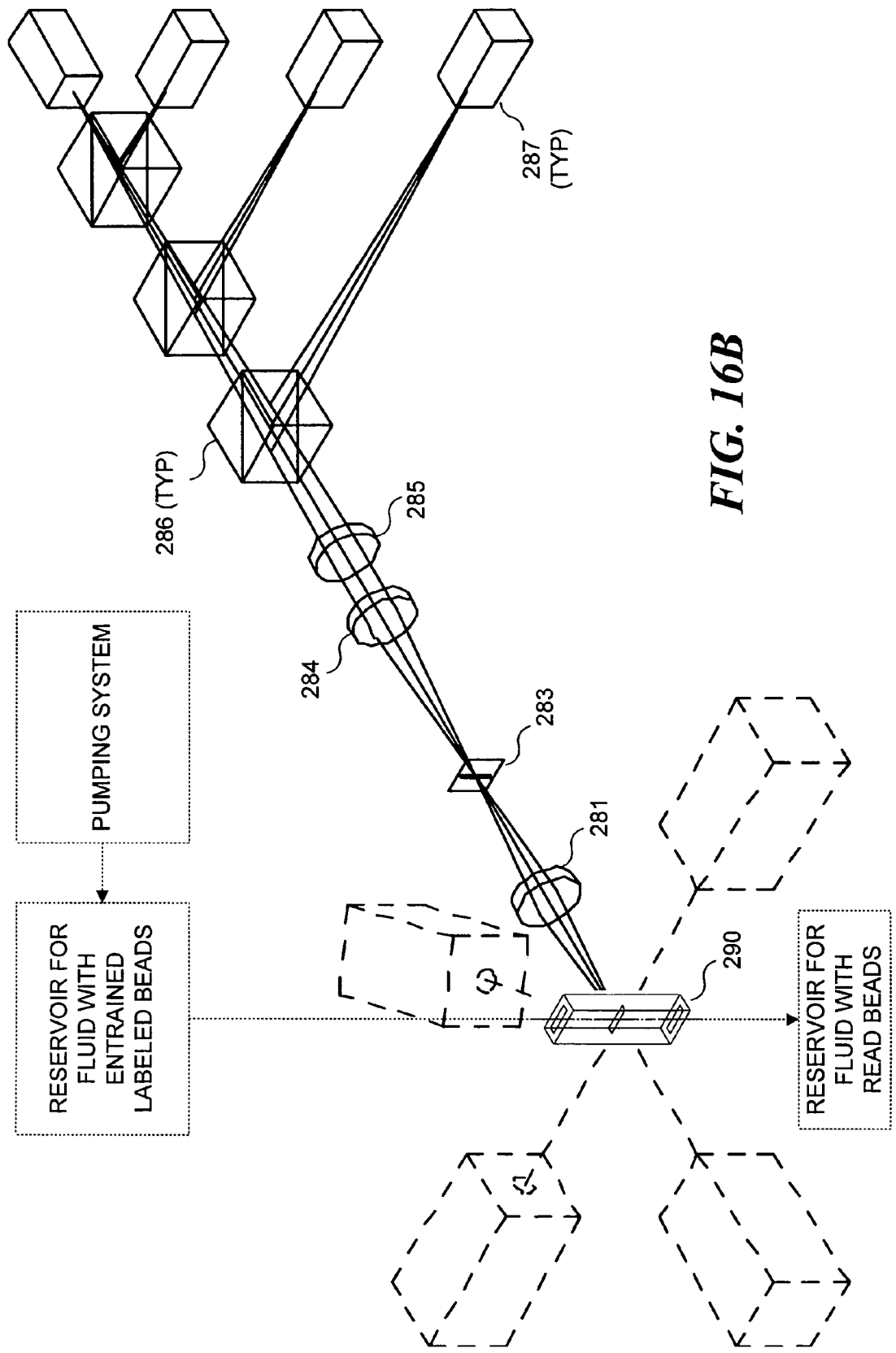
FIG. 16B illustrates yet another embodiment of the imaging system in accord with the present invention, in which the spectral emission is not convolved with the image and in which the spectral decomposition occurs in an axis perpendicular to flow through the use of one imaging lens and separate dichroic filters, and detectors for each spectral region.

The fourth embodiment of apparatus usable for spectral decomposition and imaging in connection with the present invention, which is illustrated in FIG. 16A, is similar to the second and third embodiments in that no convolution of the emission spectra with the image occurs as a result of the spectral decomposition process. Spectral decomposition occurs in an axis generally perpendicular to flow through the use of dichroic filters as previously described. However, in this embodiment, separate imaging lenses and detectors are used for each spectral region. Dichroic filters 277 are placed at infinity (with respect to the object) after a collection lens 278 to minimize optical aberrations. After each dichroic filter 276a separate imaging lens 280 is used to form an image of the objects onto the corresponding detectors 282. In this configuration, each detector 282 has fewer pixels than other embodiments because each detector covers only one spectral band. In the case where a six-color version of this embodiment is employed, the images on a single detector would appear like the images seen on one zone of the detector illustrated in FIG. 17. For example, the images seen on the detector configured to receive light in the red part of the spectrum would appear like the right-most zone of FIG. 17. Since the total number of pixels in each detector is low, these detectors may operate at very high speeds. The embodiment shown in FIG. 16A has the advantage of being more efficient than other embodiments, because the light from the object only passes through each dichroic filter 277 once. A still further advantage of this embodiment is that each detector 282 can be focused independently for each color thereby simplifying the optical design by removing the constraint of longitudinal color correction. An additional objective lens 48 and slit 52, such as that shown in FIG. 2C can be incorporated into the embodiment shown in FIG. 16A to prevent unwanted light from striking one or all of the pixelated detectors.

Fifth Embodiment of Apparatus for Spectral Decomposition and Imaging

FIG. 16B illustrates another embodiment for spectral decomposition imaging. It is similar to the previous embodiment, however, it has the advantage of reducing the number of imaging lenses required to project an image upon the detectors. In the imaging system of FIG. 16B, light from beads (or other objects) is focused by an objective lens 281 onto a slit 283. Slit 283 is sufficiently narrow to block light that is not focussed onto the slit by objective lens 281, thereby preventing extraneous light from passing through the slit. Light which has passed through the slit, is collected by a collection lens 284 and then directed to imaging lens 285, both of which are placed before the dichroic filters 286. Each detector 287 is placed at the appropriate position along the optical path to image the object onto the surface of each detector 287. Detectors 287 are placed at the appropriate positions along the optical path to image beads or other objects onto detectors 287. The filters are placed in convergent space with respect to the image of the object and therefore each filter, depending upon its design, may impart astigmatism, coma, spherical and chromatic aberration into the imagery at each downstream detector. Progressively more of each of these aberrations are added by each subsequent filter. In a typical implementation of the present invention, the numerical aperture in the filter space is approximately 0.03. Therefore, if cube substrates are employed for the dichroic filters, coma and astigmatism are negligible while spherical aberration is less than 0.15 waves peak. Longitudinal chromatic aberration is effectively canceled by moving the detectors to the plane of best focus for their respective color band. Pellicles can also be used in place of the cubes with excellent theoretical optical performance.

Figure 16C:
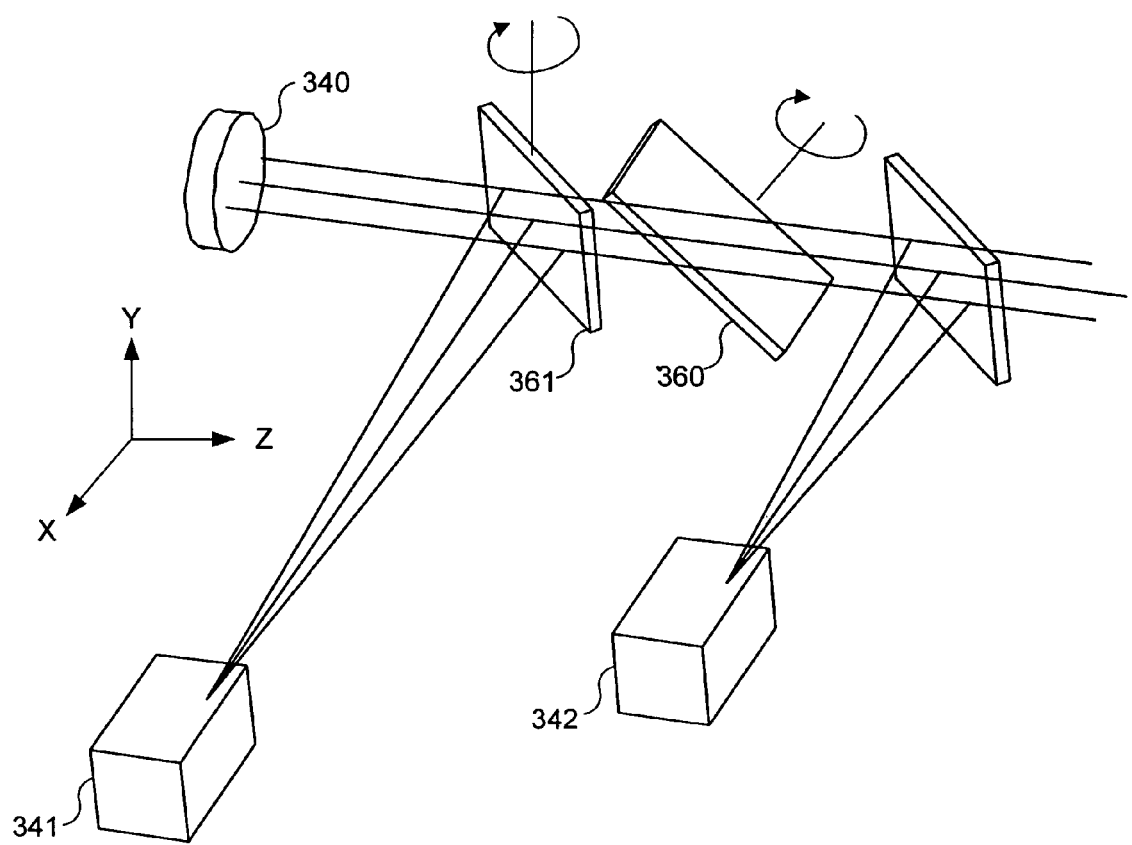
FIG. 16C is an isometric illustration of correction plates added to correct for astigmatism induced by a plate beam splitter placed in convergent space.

If plate substrates are employed for dichroic filters 286, then astigmatism dominates the aberrations. Astigmatism is imparted in the transmitted wavefront through a plate dichroic filter, but can effectively be cancelled by inserting a clear correction plate 360, as shown in FIG. 16C, of approximately the same thickness, incident angle, and glass type. However, correction plate 360 must be rotated 90 degrees about axis Z with respect to dichroic filter 361. Correction plate 360, and dichroic filter 361 impart an equal but opposite amount of astigmatism in the transmitted wavefront, thereby canceling each other. Therefore, light striking detector 342 is free of astigmatism. This configuration leaves a small amount of residual coma. Yet, the optical performance is very close to the diffraction limit. Note that because light striking a detector 341 is reflected light, as opposed to transmitted light, there is less concern about astigmatism.

Those of ordinary skill in the art will appreciate that the correction plate can be placed in many alternative positions, with adjustments in its thickness, material, and/or angle, relative to the propagation of the light. Note that FIG. 16C shows only part of an optical system, including only some of the elements employed after a collection lens 340. Of course, the flow cells, optional light sources and additional detectors (see FIG. 16A) are included in a complete system.

Any of the non-distorting spectral dispersing embodiments can be constructed using an additional objective lens 48 and slit 52, to form a confocal stop arrangement as shown in FIG. 16B. FIG. 16B also illustrates that detectors may be placed in either the transmission or reflection paths of dichroic filters. Either of the multiple detector embodiments may constructed such that the detectors receive light transmitted through the dichroic filters, reflected by the dichroic filters or in a combination of transmission and reflection as illustrated in FIG. 16B.

Note that FIG. 16B also indicates optional ancillary components that might be beneficially incorporated into imaging systems in accord with the present invention, such as a pumping system, a reservoir for fluid into which encoded beads are entrained, and a reservoir for beads that have already been imaged and read. It should be understood that such components could be similarly incorporated in the other imaging systems of the present invention.

In all spectral decomposition and imaging embodiments, it is anticipated that the magnification is set such that one detector pixel in object space is roughly the size of a single reporter. Given a detector pixel size of 10 microns and a reporter size of one micron, the magnification would be configured to approximately 10×. Likewise, if the reporter were 0.5 microns, the magnification would be set to approximately 20×.

As disclosed in the above-referenced U.S. Pat. No. 6,211, 955 and as shown in FIGS. 1 and 4, multiple legs of the spectral decomposition and imaging system may be used to collect images and corresponding signals from multiple perspectives. Two legs are shown in FIG. 1; however, if epi illumination is applied as shown in FIGS. 3 and 4, four legs may be used to view the beads from each side of the cuvette. Light emitted from the beads may also be collected with objective lenses that can be optically coupled directly to the cuvette to improve the numeric aperture. In addition, each optical leg can image beads at multiple focal planes to improve focus on reporter beads which may be out of focus at a different focal plane.

Pixelated Detection

Pixelated detection employs frame-based CCD image collection, in which a CCD detector views beads in flow, in a freeze frame fashion. This method requires the integration time to be very short to prevent blurring. A short integration time is achieved either with a strobed light source, or a continuous light source combined with a shuttered or gated detector. In either case, the short integration time reduces the signal-to-noise ratio and the ultimate sensitivity of the approach with fluorescence signals. Further, frame-based cameras require time to transfer data out of the pixelated detector, during which no images are acquired, and beads of interest can escape detection. However, these types of detectors are readily available, inexpensive and do not require an accurate knowledge of the velocity of the beads in flow.

Alternative Approach for Pixelated Detection

Another approach useful in bead imaging for pixelated detection also employs frame-based CCD image collection, but does not rely on strobed illumination or shuttered detection to freeze image motion. Instead, a rotating or oscillating mirror (not shown) is used to compensate for bead motion to produce a still image on the detector. This technique may employ continuous illumination, thereby achieving higher levels of sensitivity than strobed systems when analyzing fluorescence. However, this approach requires both an accurate measurement of bead velocity and a very stable fluid pumping system, since the inertia of the mirror prevents compensation for rapid changes in bead velocity.

A Further Technique for Pixelated Detection

Yet another method for pixelated detection uses TDI CCD image collection. In TDI detection, the electronic signal produced within the detector by an incident image is moved down the detector in synchrony with the motion of the image. In this manner, signal integration times can be increased over conventional frame imaging modes by a factor exceeding 1000 fold.

Bead Illumination

As previously discussed in conjunction with several embodiments of the present invention and as shown in FIGS. 3 and 4, several different illumination systems may be employed to illuminate the beads in flow. A standard approach involves illuminating the beads in flow with a light source providing light along a path oriented orthogonal to the spectral decomposition and imaging system. Alternative modes of illumination, such as those shown and FIGS. 3 and 4 and disclosed in above-referenced U.S. Pat. No. 6,211,955, allow for the generation of bright field, dark field, phase contrast, fluorescence and EPI fluorescence imagery. U.S. patent application Ser. No. 09/689,172, entitled "Multipass Cavity for Illumination and Excitation of Moving Objects," filed on Oct. 11, 2000, discloses a method for illumination in which the number of photons incident on the beads may be increased by a factor of 10 or more.

The design of the illumination system also allows the use of pulsed light source or other strobed sources for high sensitivity fluorescence measurement without any need to strobe in synchrony with bead flow. A high aspect ratio also allows for highly efficient coupling of linear array diode illumination into the cuvette.

Bead Velocity Measurement

For the second and third pixelated detection techniques, wherein an accurate knowledge of the bead velocity is required, either a frequency domain velocity measurement (FDVM) technique or a time domain velocity measurement (TDVM) technique, both as disclosed in U.S. patent application Ser. No. 09/939,292, filed on Aug. 24, 2001 and entitled "Measuring the Velocity of Small Moving Objects Such as Cells" can be employed. In FDVM, a large FOV is imaged onto a ruling of opaque and transparent bars. Motion of the objects within the FOV causes modulation of their intensity as they pass across the ruling. The modulation frequency is proportional to the velocity of the objects and can be determined using Fast Fourier Transform analysis.

Velocity can also be determined using two detectors in a conventional time-of-flight measurement scheme, though with very restricted throughput. However, time-of-flight measurements become more complex when throughput increases and the times of flight of multiple objects are measured simultaneously. Such systems can fail when correlation is lost between the entry and exit times of the objects in view. The time-of-flight system preferably used relies on an improved scheme wherein the waveforms produced by the entry and exit detectors are cross-correlated to detect phase changes that are indicative of changes in velocity.

Sample Handling

A standard pumping technique of the type used in prior art flow cytometers can be used to hydrodynamically focus the beads with micron-scale positional accuracy within the cuvette. Hydrodynamic focussing of the beads ensures they are located in or near the plane of focus of the optical system. Handling reporter labeled beads in suspension in the present invention eliminates the need to array beads in a monolayer on a substrate. When analyzing large samples containing a billion beads, the substrate methodology becomes impractical due to the number of substrates or the size of a single substrate required to carry a billion or more beads. A sample of four billion, 10 micron beads occupies a volume of as little as $4.0\ cm^3$ or 4.0 milliliters. By comparison, when arrayed in a perfect tightly packed monolayer, that same four billion bead sample would occupy a square area of over 24 inches on a side. Or, when produced in more manageable format such as a standard microscope slide, the four billion bead sample will occupy more than 1728 slides. Other advantages of handling beads in suspension include the ability to sort individual beads at high speed, the ability to collect bead images from multiple perspectives, and the ability to hydrodynamically focus beads into a tight focussable core near the focal plane of the collection system. To increase throughput in flow, the sample stream may have a high aspect ratio in the plane perpendicular to flow. This technique is discussed in U.S. Pat. No. 5,422,712 "Apparatus for Measuring Fluorescent Spectra of Particles in a Flow" the specification and figures of which are specifically incorporated herein by reference for purposes of providing background information regarding the technique commonly referred to as broad flat flow. Broad flat flow allows objects to flow in a plane as opposed to single file through the flow cell. This increases throughput by allowing beads to flow more or less parallel to each other while maintaining a tight plane of focus. Those skilled in the art will appreciate that broad flat flow can easily be created using commercially available flow cells as shown in FIG. 16B containing flow cell 290, with a cross section that is elongated in an axis perpendicular to both the flow and optical axes.

Spatial and Spectral Corrections to Pixelated Imagery

In the second through fifth embodiments, a spatial and spectral correction may optionally be applied to the signals coming off the pixelated detector(s) to improve the integrity of the decoding process. A method and apparatus for such a system is disclosed in U.S. provisional patent application Ser. No. 60/286,713 entitled "Method and Apparatus for Cross-Talk and Spatial Registration Correction for Multi-channel Imaging." In this scheme, spatial registration errors between channels on the detector, or spatial registration errors between detectors, is corrected to more accurately determine the origin of light projected upon the detector. Likewise, once a spatial correction has been applied, a spectral correction is applied to remove any spectral cross-talk between channels or detectors to more accurately determine the spectral content of light projected onto each pixel on the detector(s).

All figures illustrating imaging systems in the present invention employ pixelated detectors. In some embodiments multiple images of reporter labeled carrier beads are projected upon a single detector as illustrated in FIG. 11. In other embodiments such as that illustrated FIG. 16A multiple detectors are employed, each containing a different imagery of the same reporter labeled carrier beads.

Figure 23:
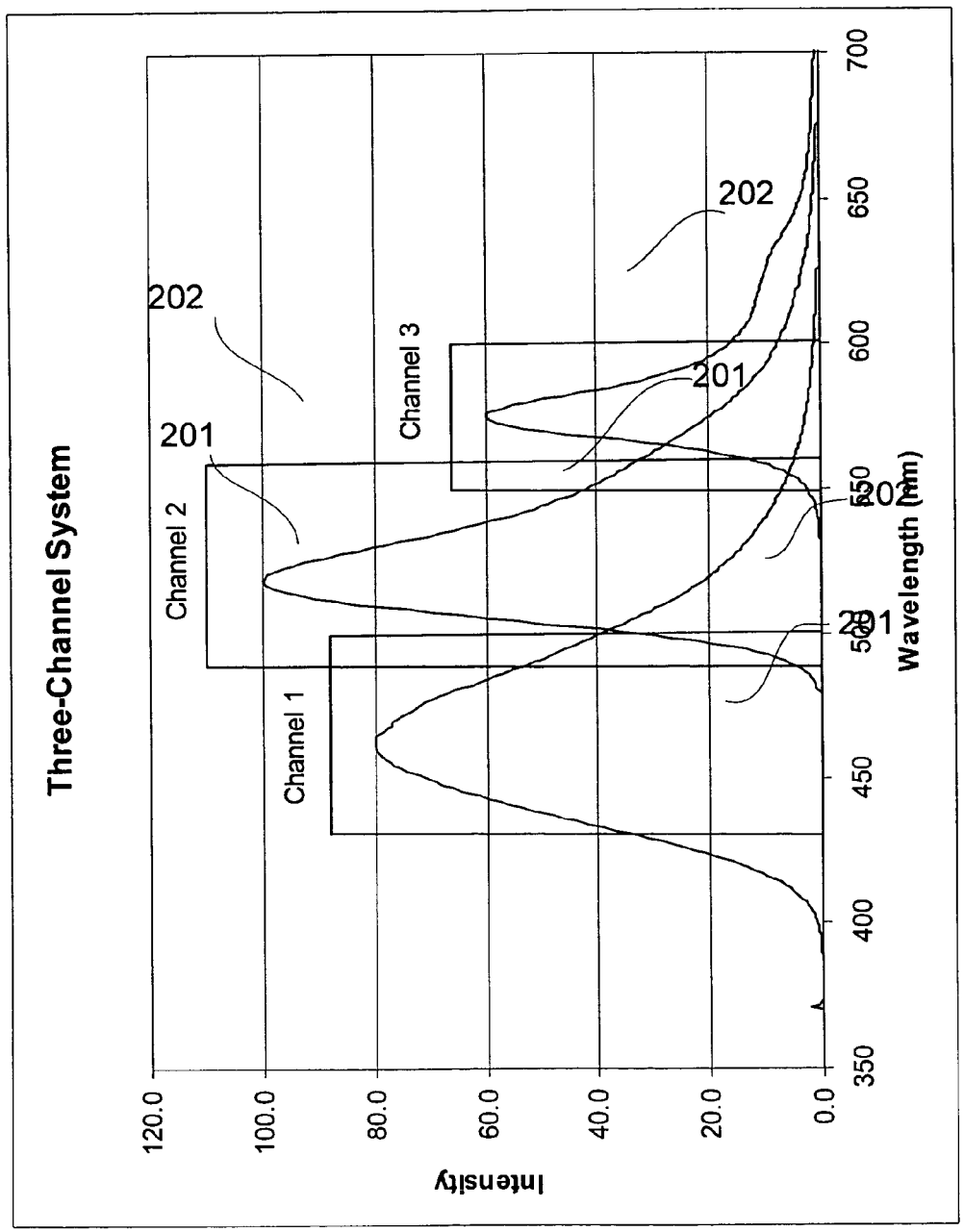
FIG. 23 is a plot of channel spectral passbands superimposed over emission spectra for common fluorochromes used in reporter beads, carriers, or binding signals.

Ideally, each of the reporters or carriers being imaged by the present invention would deliver light comprised of wavelengths entirely bounded by the edges of the passband of a particular channel. In that case, each source type (bead fluorochrome) would appear in only one channel of a detector or on only one detector in the case of a multiple detector embodiment. However, in many cases the fluorochromes used in the reporters, carriers or binding signals span a range of wavelengths broader than the passband of the associated imaging filter. This is clearly illustrated in FIG. 23, where emission spectra of several fluorochromes are superimposed over the passbands of several channels on a wavelength versus intensity plot. In this case, light from each source 201 will be received by two or three channels 202. The signal conveyed by each channel, then, is a composite of information from multiple sources. This can make reporter identification difficult, especially when reporters are intensity coded as well as spectrally coded. Therefore, the signals from the various detectors or channels must be operated on in a way to remove the crosstalk to accurately determine the spectral content and intensity for each reporter, carrier or binding signal Fundamentally, to remove crosstalk a set of linear equations as shown below must be solved.

$$s_1 = \alpha_{11} m_1 + \alpha_{12} m_2 + \alpha_{13} m_3$$

$$s_2 = \alpha_{21} m_1 + \alpha_{22} m_2 + \alpha_{23} m_3$$

and $$s_3 = \alpha_{31} m_1 + \alpha_{32} m_2 + \alpha_{33} m_3$$

where:
$m_j$=measurement from channel j,
$s_i$=a characteristic parameter of source i, and
$\alpha_{ij}$=weighting coefficient, source i into channel j.

The weighting coefficients carry information about the sources and about the channels used to collect the measurements. The equations are solved using the methods of linear algebra, wherein the variables $s_i$, and $m_j$ are treated as vectors and variable $\alpha_{ij}$ is treated as a matrix. The general term for this process is "crosstalk correction", since it removes the information from a source that has fallen into a channel adjacent of the correct channel. This information spillover is analogous to crosstalk in bundled telephone lines, which results in a listener hearing the conversation from another line.

This set of equations must be solved for each pixel location. It is essential, then, that the images from all of the channels be precisely aligned with one another so that the correct measurements are entered into the equations for each pixel location. Therefore, a computational process is applied to the images belonging to a field of view before the crosstalk correction is applied. The "field of view" is the scene captured in an image. The images belonging to a field of view may be referred to as the "image ensemble" for that field of view.

Figure 24:
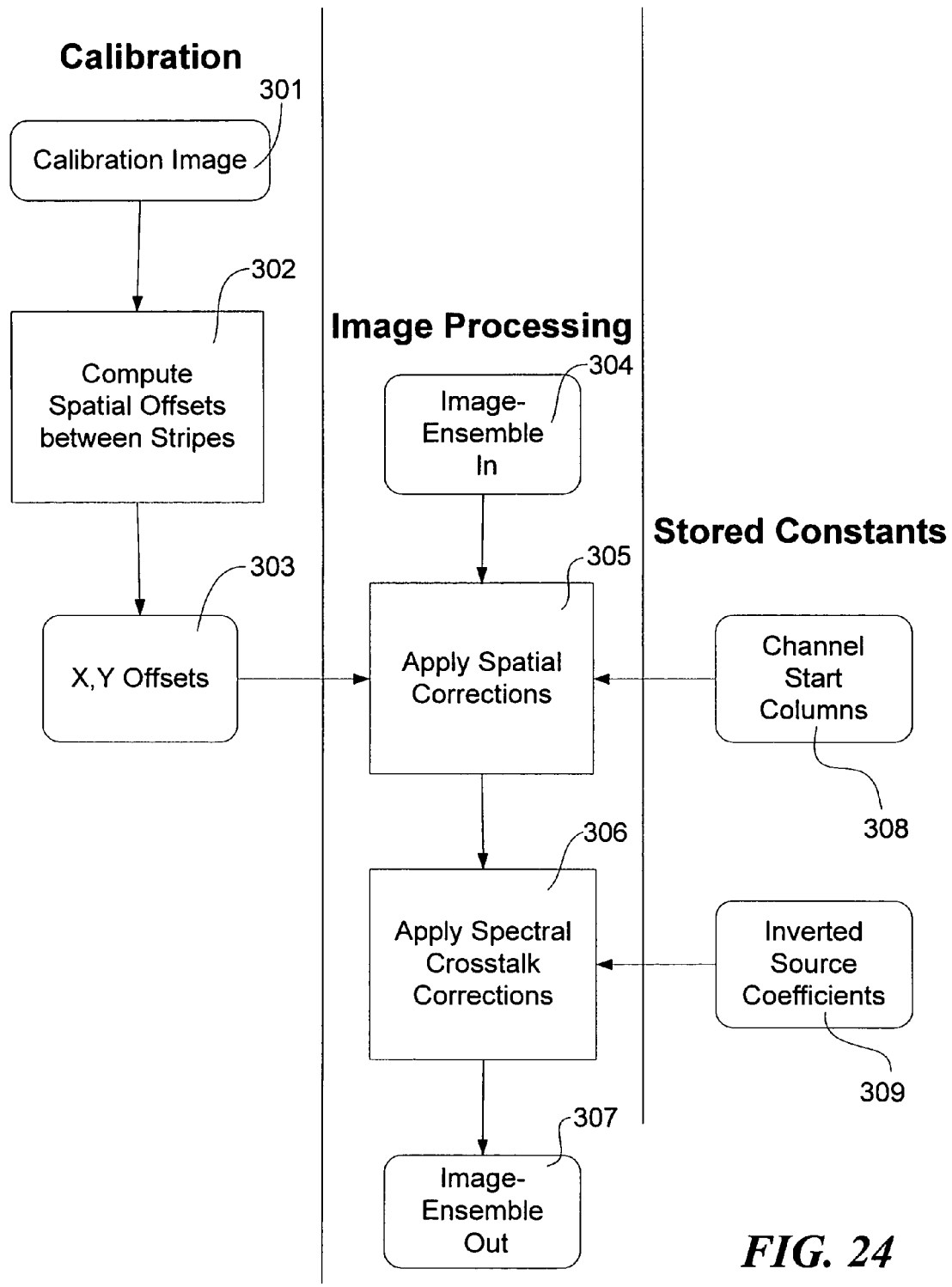
FIG. 24 is a block diagram illustrating the general steps employed in the method of the present invention for applying crosstalk corrections to reporter labeled bead imagery prior to decoding the reporter labeled bead assemblies.

FIG. 24 is a block diagram of the operations required to carry out the spatial and spectral corrections. It includes two significant image processing operations, applying spatial corrections executed in a block 305 and applying spectral cross talk corrections, executed in a block 306. In block 305, the images from a plurality of channels are spatially aligning, and in block 306, corrections are applied to remove the channel-to-channel crosstalk. There are two classes of information that support the operations executed in blocks 305 and 306. The first is the class of calibration constants, derived from on-line calibration of the instrument during its operation. The second class of supporting information is that for which stored tables of constants are accessed during operation, but not modified.

In a block 301, a calibration image that is generated from a plurality of offset stripes (the spatial offset for the calibration image being known) is introduced to the instrument. The instrument then computes the spatial offsets between the stripes in a block 302. The X,Y (horizontal and vertical) spatial offsets are determined in a block 303. Note that the image misalignment responsible for such spatial offsets may be subject to thermal drift and other factors that may vary during operation. The X,Y spatial offsets are used in block 305, along with other information, to apply spatial corrections.

The stored constants will have been derived from measurements and from the known characteristics of the objects to be imaged. Different stored constraints will be applied to the spatial corrections executed in block 305 than are applied to the crosstalk corrections executed in block 306. For example, the general positions of the channels relative to each other known, and these positions are required for the spatial corrections executed in block 305. The stored data relating to the general positions of the channels relative to each other are provided to a processor executing the spatial corrections of block 305 in a block 308. With respect to the crosstalk corrections executed in block 306, stored data relating to the inverted source coefficients are provided in a block 309. It should be noted that additional stored measurements and known characteristics can also be incorporated into the second class, and provided to the spatial correction operation or the crosstalk correction operation, as appropriate.

The image processing stages can be applied in real-time as images are collected during system operation, or by offline access to stored image files. The images to be spatially and spectrally corrected in blocks 305 and 306 are provided by a block 304. The resulting corrected images are output in a block 307, and are suitable for further processing and analysis, free of the information degradation caused by crosstalk and misalignment.

Figure 25:
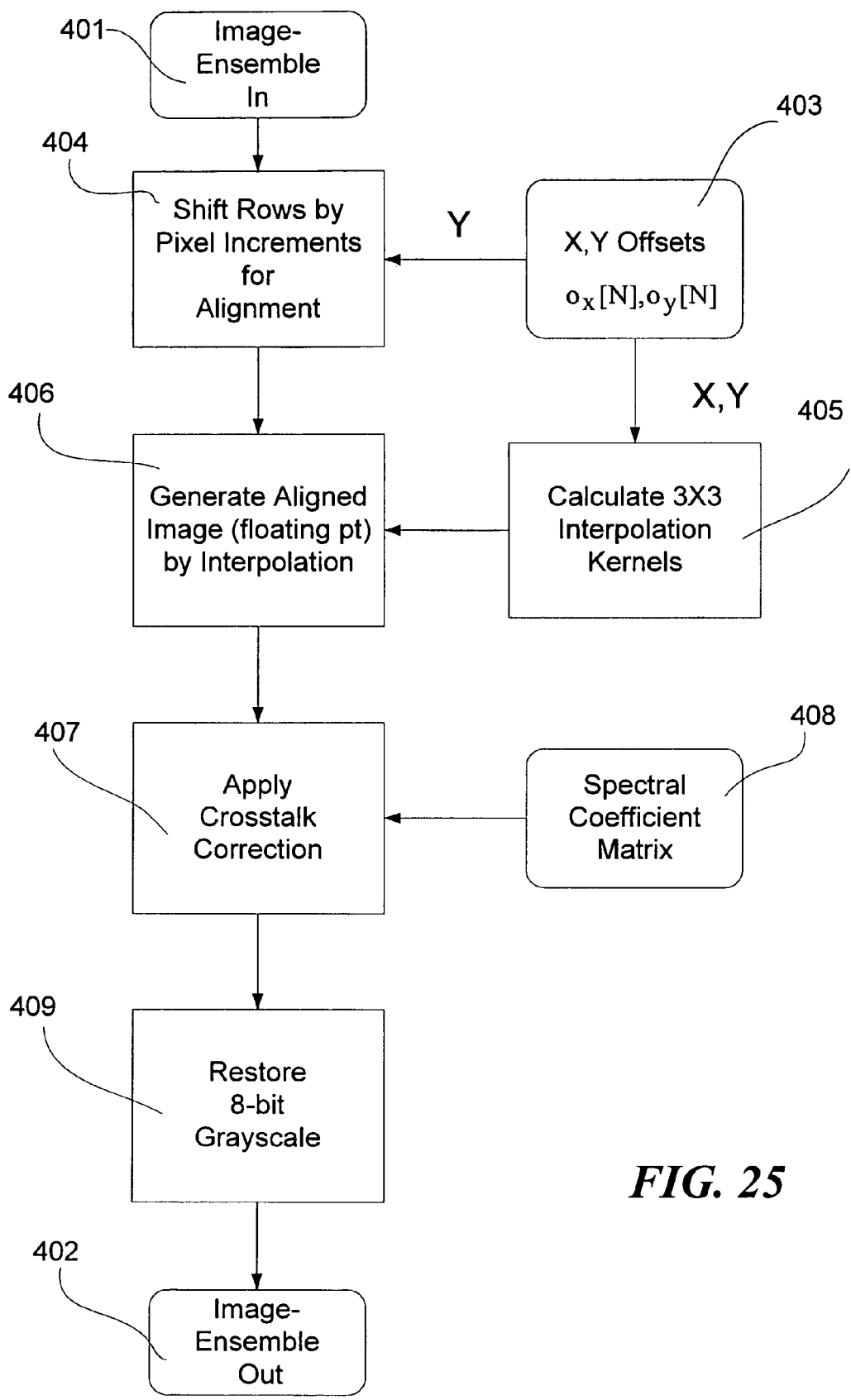
FIG. 25 is a block diagram for the steps of applying spectral and spatial corrections to reporter labeled bead imagery.

A block diagram of the general operations of the preferred embodiment of the present invention is shown in FIG. 25. An "Image Ensemble" refers to a set of images, all of which depict the same field of view, but each of which has been constructed of signals from a particular channel. The number of images in an ensemble is equal to the number of channels in the instrument. The image ensemble is generated in a block 401.

The X (horizontal) and Y (vertical) offsets are required in order for the alignment process to operate on the image ensembles. These offsets are provided in a block 403. As discussed above with respect to FIG. 24, calibration images are processed to determine these offset values. The calibration process may be run as a preliminary step in the operation of the instrument. The calibration may be repeated periodically to track drift in the image registration caused, for example, by changes in temperature. The process of generating the offsets is illustrated by a block diagram in FIG. 26.

In a block 404, images are aligned by shifting rows by pixel increments. In a block 406, an aligned image is generated by a floating point interpolation in a, using interpolation kernels generated in a block 405, based on the X,Y offsets determined in block 403. In a block 407, the crosstalk correction process described above is applied, using a spectral coefficient matrix provided by a block 408. Then in a block 409 the 8-bit grayscale is restored, resulting in a final image ready to output in a block 402.

Figure 26:
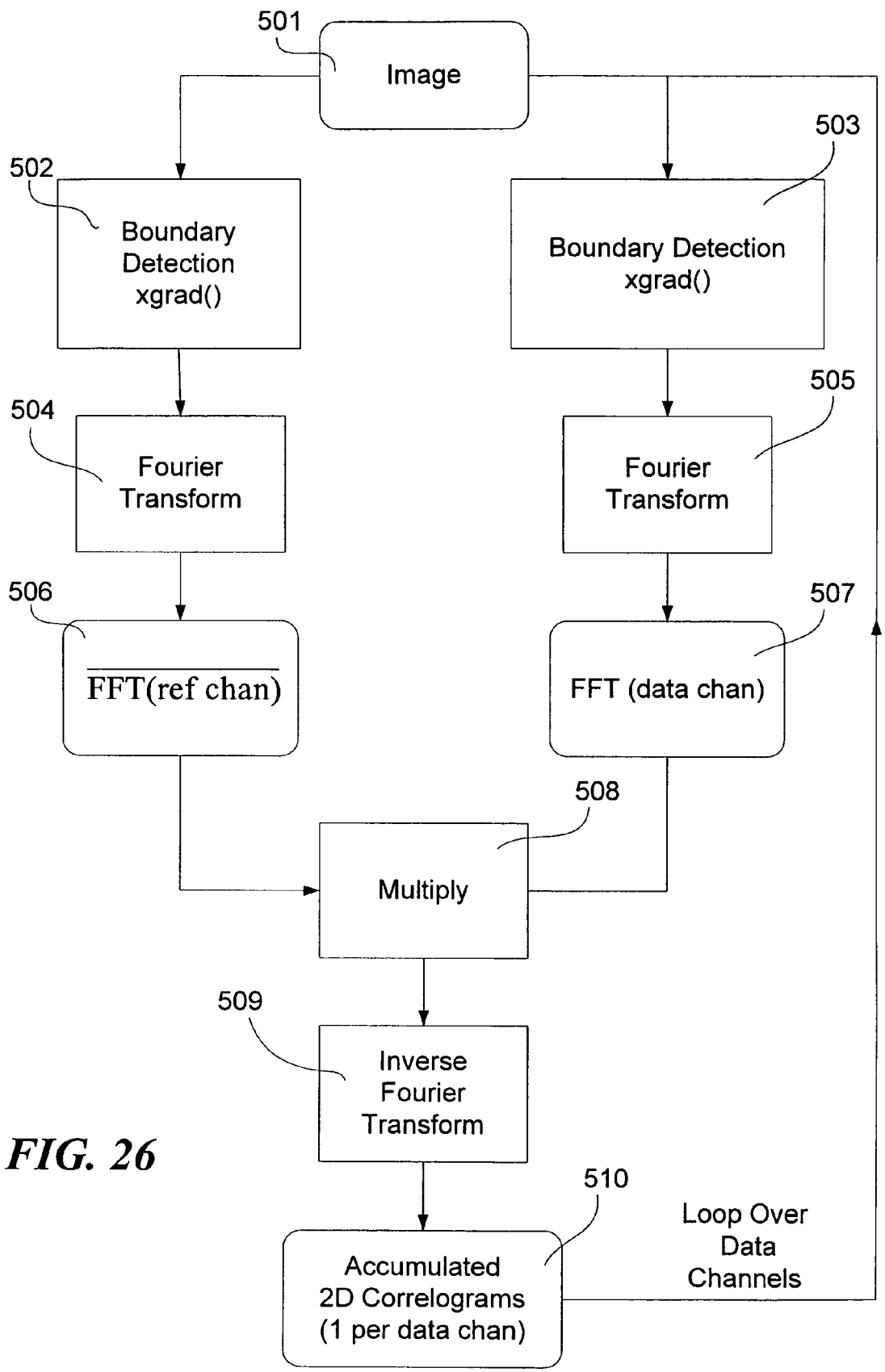
FIG. 26 is a block diagram of the steps of generating the accumulated average correlograms between the data images and the reference.
Figure 27:
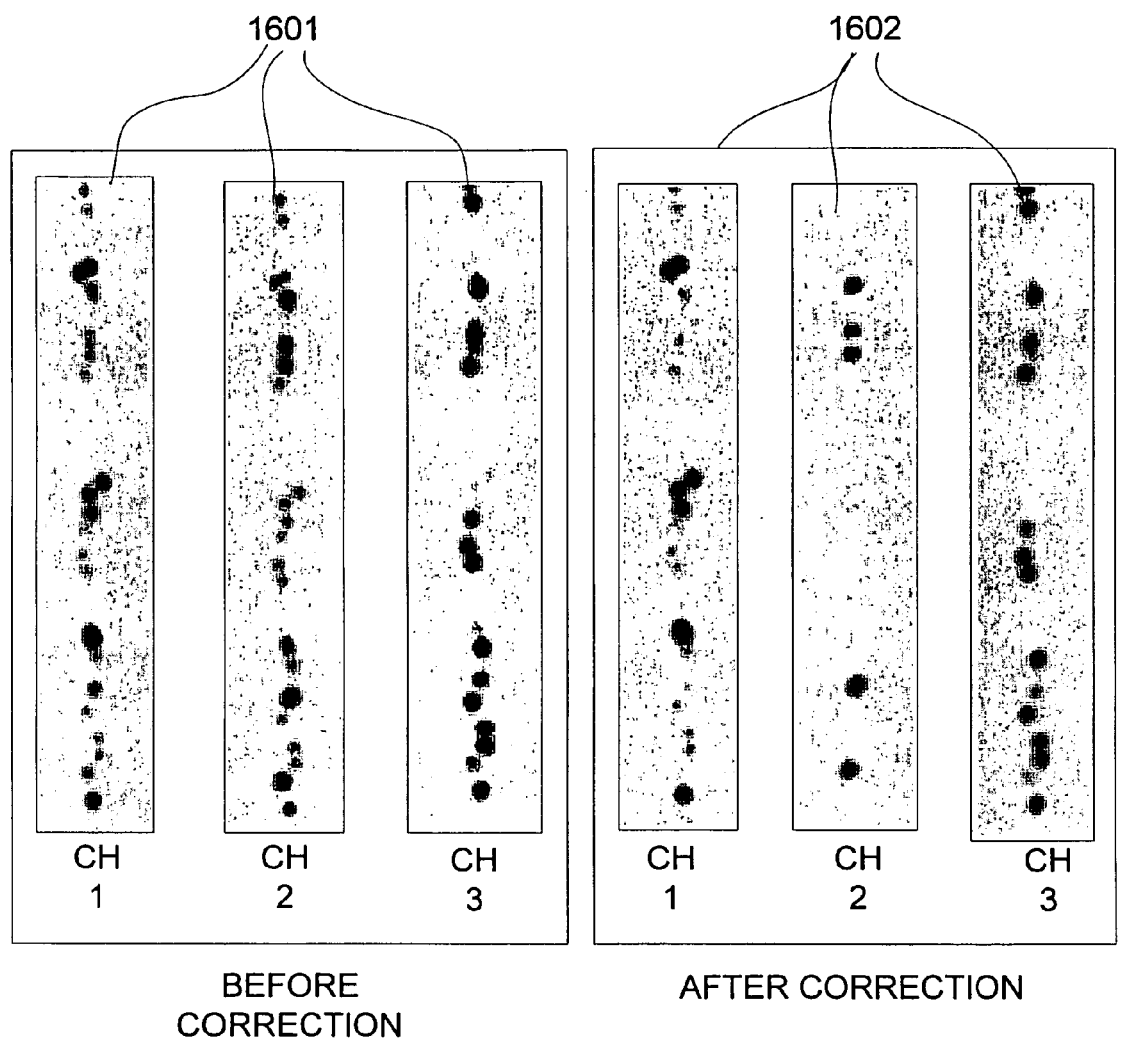
FIG. 27 is an example of imagery before and after spectral and spatial correction.

Referring now to the block diagram of FIG. 26, for each image, represent by a block 501, a first operation in the generation of the spatial offsets is that of boundary detection, executed in blocks 502 and 503. From the boundary information determined in block 502, a Fourier Transform is applied in a block 504, and then a Fast Fourier Transform is applied in the reference channel. From the boundary information determined in block 503, a Fourier Transform is applied in a block 505, and then a Fast Fourier Transform is applied in the data channel. The results of both Fast Fourier Transforms are multiplies in a block 508, and an Inverse Fourier Transform is applied to the result in a block 509. Then accumulated 2D correlograms (1 per data channel) are generated in a block 510. The process is repeated for additional images. A detailed description of the process illustrated in the block diagram of FIG. 26 is provided below. Note that FIG. 27 illustrates exemplary images before and after correction.

A two-dimensional gradient operator is used to suppress flat surfaces and to enhance object boundaries. The operator builds signal in regions where the slope of the intensity is large in both the vertical and the horizontal directions. The linear expression for this operator is as follows:

$$G = \frac{\partial}{\partial y} \frac{\partial I}{\partial x}.$$

Object boundaries carry all of the energy in the images transformed by the gradient operator. What is needed next is a way to overlay each data image onto the reference image and measure how much vertical shift and horizontal shift is required to line up the object boundaries. Cross-correlation is a preferred method for measuring these shifts, or offsets, between images.

The cross-correlation of two signals is comprised of convolving the two signals and extracting information from the output of the convolution operation, which is called the correlogram. The operation of convolution in the time domain is defined by the following equation:

$$f_1(t) \otimes f_2(t) = \int_{-\infty}^{\infty} f_1(\lambda) f_2(t-\lambda) d\lambda.$$

The value of the convolution for every time sample, t, is the sum over infinity of the product of the two functions, but with the second function offset by time t. The time delay between the two signals can be determined by finding the peak in the correlogram.

For image realignment, the convolution is applied in two dimensions to functions in x,y space, as follows:

$$f_1(x,y) \otimes f_2(x,y) = \int\int_{-\infty}^{\infty} f_1(\varepsilon, \eta) f_2(x-\varepsilon, y-\eta) d\varepsilon d\eta.$$

The alignment method is based on the premise that there will be similar structures in the images to be aligned. In the ideal case, the second image is identical to the first except for a shift in x and y. Furthermore, the shift can be represented as the convolution of the function with the two-dimensional Dirac delta function, thus:

$$f_2(x,y) = f_1(x-x_0, y-y_0),$$

and $$f_2(x,y) = f_1(x,y) \otimes \delta(x-x_0, y-y_0).$$

The image offsets, $x_0$ and $y_0$, can be measured from the shift in the two-dimensional correlogram, since:

$$C_{1,2} = f_1(x,y) \otimes f_2(x,y) = f_1(x,y) \otimes f_1(x,y) \otimes \delta(x-x_0, y-y_0).$$

The Fourier Transform provides a convenient method for accomplishing the convolution of two images, as seen in the theorem:

$$f_1(x,y) \otimes f_2(x,y) = F^{-1}[F_1(\omega_x, \omega_y) \cdot F_2(\omega_x, \omega_y)]$$

where:

$F(\omega_x, \omega_y)$=Fourier Transform of f(x,y), $F^{-1}[X(\omega_x, \omega_y)]$=Inverse Fourier Transform of $X(\omega_x, \omega_y)$.

In the frequency domain, then, the two-dimensional convolution becomes a matrix multiplication of the spectra of the two images. The two-dimensional correlogram is obtained by performing the inverse Fourier Transform of the product.

Because objects may occupy only a few pixels, and because the resolution of the imaging system may be on the order of a pixel width, alignment of one image to the next to a resolution of a fraction of a pixel width is necessary for accurate crosstalk correction. The true peak of the correlogram will rarely be centered on a pixel. The true peak can be located, however, by analyzing the shape of the region around the pixel of maximum amplitude. If an accurate equation can be defined for the correlogram amplitude in that region, the true location of the peak can be found to a resolution better than a single pixel width.

For cross talk correction an image is reconstructed for alignment by application of two-dimensional interpolation. In this process, once the image has been aligned with the reference image to the nearest pixel, the new amplitude value for each pixel is computed as the weighted sum of a group of surrounding pixels. The values of the weighting coefficients for the interpolation depend on the amount of shifting to be accomplished in the vertical direction and the horizontal direction. These shift distances will be less than one pixel width.

With aligned data images in place, the crosstalk correction can be accomplished. FIG. 27 illustrates imagery before and after cross talk correction. Imagery 1601 clearly shows objects imaged upon a detector in the presence of uncorrected cross talk. Imagery 1602 illustrates the same imagery after cross talk has been removed. Depending upon the means for used for tagging reporters, fluorochromes, quantum dots etc., it may or may not be necessary to remove cross talk from imagery projected upon the detector(s) before decoding.

Analyzing Reporter Labeled Beads Using the Flow Imaging System of the Present Invention Decoding of reporter labeled beads by the second embodiment of the flow imaging system is depicted in FIG. 17. Each bead and its associated reporters are simultaneously imaged multiple times across several rows covering a horizontal region on the detector, each image corresponding to a different emission, reflectance or absorbance band. In FIG. 17, the solid substrate, or carrier bead 346, is indicated by the large circle, while reporters 348a, 348b, 348c and 348d are depicted as a smaller circle bound to the larger bead.

Each of these reporters can be seen in the (Optional) reference channel of the detector. The imagery in this section can be generated by light source scatter signals from the beads and reporters or by absorbance signals generated from band limited brightfield illumination. For reporters using fluorescence to uniquely identify their optical signature, the reference channel is optional if each reporter contains at least one type of fluorochrome. A binding signal is indicated by a filled circle 346b in the binding signal section of the detector. A signal in this channel indicates that an analyte has bound to the bead as a result of the assay. Further, the intensity of the signal in the binding signal channel can be used to further characterize the binding event to determine the quantity of the analyte present in the assay.

Reporter signals are imaged in the remaining blue, green, yellow and red channels of the detector. The present invention maintains the relative positions of all reporter imagery in each channel. Thus reporter 348a is associated with imagery 342a in the yellow channel and imagery 342b in the red channel of the detector. Reporter 348a contains both yellow and red fluorochromes, and since no other imagery appears in the blue or green channels, no other fluorochromes are present in reporter 348a. Similarly, reporter 348b is associated with imagery 343a in the blue channel and imagery 343b in the red channel, reporter 348c is associated with imagery 344a in the green channel and imagery 344b in the yellow channel, and reporter 348d is associated with imagery 345a in the blue channel and imagery 345b in the green channel.

Figure 19:
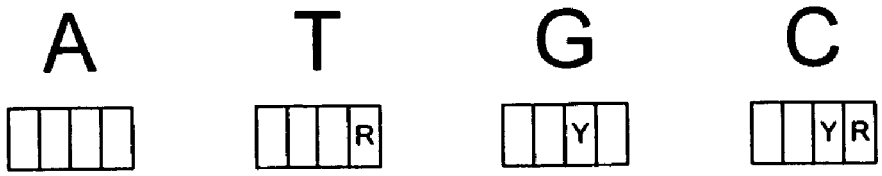
FIG. 19 is a reporter legend that aids in the identification of reporter labeled beads.
Figure 19:
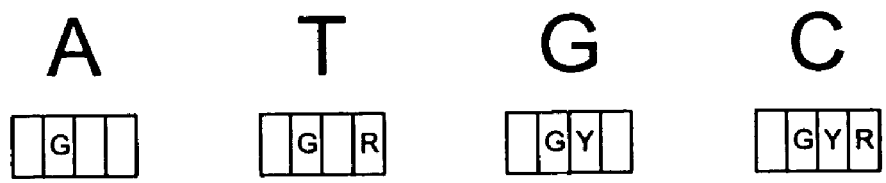
Figure 19:
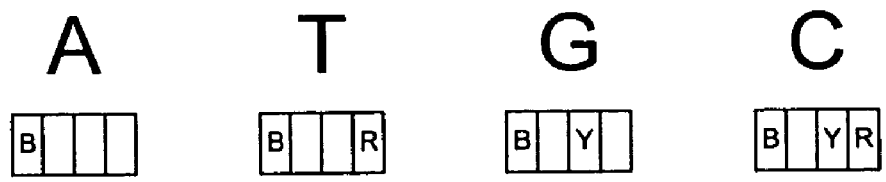
Figure 19:
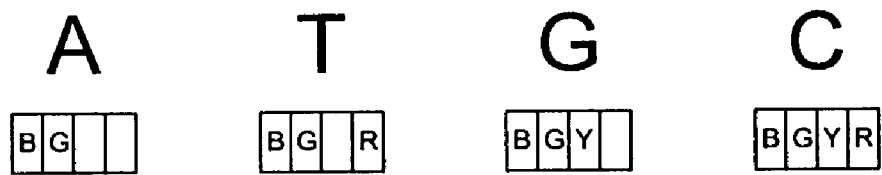

Such reporter imagery must be matched to a known reporter legend, to identify an object that is associated with a specific reporter. It should be noted that reporter labeled beads can be associated with many different types of objects, such as cells, chemical or biological compounds. As discussed in the Background of the Invention, certain types of DNA related research involves the preparation of libraries of synthesized compounds, such as an oligo library generated using the SAP technique described above. Such compounds are produced by combining a plurality of subunits (for example, nucleotide bases) together to form a larger compound (such as an oligomer). While several different methods can be employed to produce such compounds, if each subunit is individually tagged with an identifying characteristic, such as a fluorchrome, then the presence of a reporter encodes the identity of the subunit in the compound, and its location relative to other subunits, based on a known reporter legend. FIG. 19 illustrates a reporter legend, that was generated when a oligo library comprised of nucleotide bases was generated. According to the reporter legend of FIG. 19, the presence of the yellow-red reporter 348a indicates cytosine (C) in a first position in the oligo bound to bead 346. The presence of the blue-green reporter 348d indicates an adenine (A) in the last position of the oligo bound to bead 346. In this manner, all positions of an oligo can be determined by identifying the color combinations present in each reporter. Using the present invention it is very straight forward to decode the "CGTA" oligo sequence synthesized on bead 346. Furthermore, the presence of the binding signal (see FIG. 17) indicates whether or not the complimentary "GCAT" sequence has bound to the bead during the assay. It should be noted that while reporter labeled beads will be useful in identifying all the subunits of a compound that include individually labeled subunits, it is anticipated that it will also be useful to label (and read) compounds not at the subunit level, but just at the compound level. Thus the present apparatus and method is not limited to imaging and reading only compounds that include individually labeled subunits.

The decoding process described above is identical for the fourth and fifth embodiment of the flow imaging system described above, but each spectral band is imaged onto a separate detector. Although this embodiment requires more detectors, each detector can have relatively few pixel columns since there is only one spectral band per detector. This embodiment is also more optically efficient because the light reaching the detector passes the filter set once, unlike the previous embodiment where light must pass through each filter twice before exiting the dispersing component and reaching the detector.

The decoding process used for the first embodiment is similar in concept to the process employed for the second through fourth embodiments, except that the reporter images must be generated by first deconvolving emission spectra of the fluorochromes used from the imagery on the detector. Deconvolution of the emission spectra from the bead image requires significant image processing, which is a disadvantage for real-time analysis. However, the advantage of this first embodiment is that it potentially provides the highest spectral discrimination power, but uses only one detector and one optical dispersing element, reducing system cost.

Figure 18A:
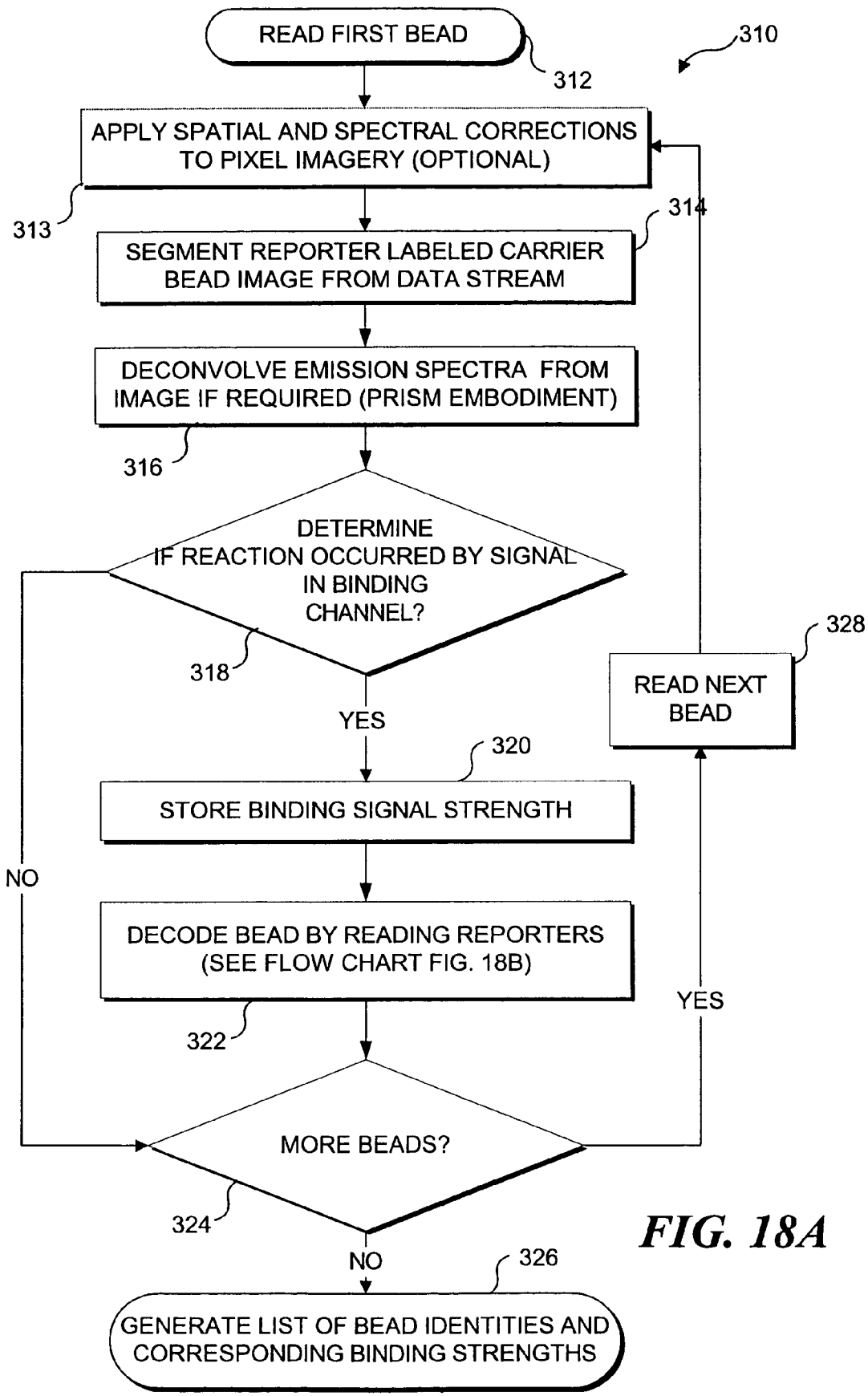
FIG. 18A is a flow chart illustrating the steps employed in the method of the present invention for reading reporter labeled beads in a flow.
Figure 18B:
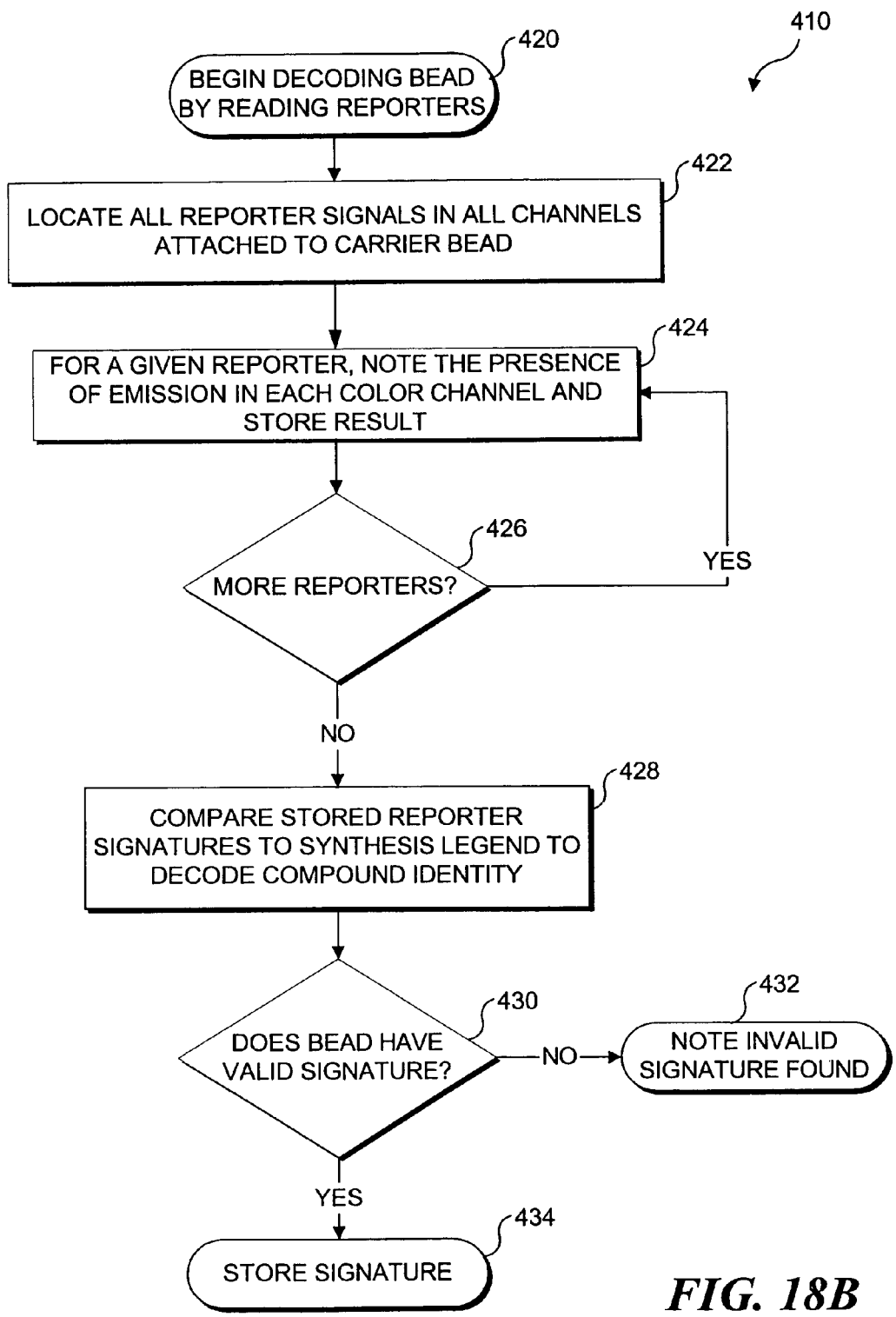
FIG. 18B is a flow chart illustrating the steps employed in the method of the present invention for decoding the reporters on a reporter labeled bead.

FIGS. 18A and 18B include flowcharts 310 and 410 that provide the series of logical steps employed to read reporter labeled beads in accord, with the present invention. Referring to FIG. 18A, in a start block 312, a first bead is read. In a block 313, spectral and/or spatial corrections are optionally applied to the pixelated signals from the detector to more accurately determine the spectral content in each pixel of the imagery. Next, the data from the bead imaging are segmented into a plurality of different reporter signature channels in a block 314. The number of signature channels in the present invention is chosen to be equal or greater than the number of different colors present in any reporter. In FIG. 19, the reporter legend is based on reporters that comprise no more than 4 colors. Thus, FIG. 17 includes four separate reporter signature channels, including "BLUE," "GREEN," "YELLOW," and "RED."

In a block 316, the deconvolution step discussed above is performed, but only if required, as would be the case for the first embodiment of the imaging and spectral decomposition. In a block 318 the binding signal channel is checked to determine if an analyte has bound to the bead indicating the presence of the analyte in the sample being tested. If no binding signal is present the logic determines if more beads are to be read in a decision block 324. If in decision block 324 it is determined that no more beads are to be read, a list of bead identities and binding strengths are generated in a block 326, as will be described in more detail below, with respect to FIG. 18B. If in decision block 324 it is determined that more beads are to be read, the next bead is read in a block 328, and the logic loops back to block 313 as described above If in decision block 318, it is determined that a binding signal is present, the presence and or strength of the binding signal is stored in a memory in a block 320. In a block 322, the bead is decoded as described in detail below in conjunction with FIG. 18B. In the decoding process, when a valid bead signature is found, the signature or compound identity is stored along with the binding indicator. At this point the logic determines if more beads are to be read, in decision block 324, as described above.

The method for determining compound identity is illustrated by flowchart 410 in FIG. 18B, which as noted above is executed in block 322 of FIG. 18A, as noted in a block 420 in FIG. 18A. After bead imagery has been segmented in each channel, individual reporters are evaluated to determine their identity. In a block 422 the imagery corresponding to each reporter is located in each signature channel. This may be accomplished by any means, including but no limited to, evaluating imagery in each signature channel to find the top left most reporter image and its corresponding imagery in other channels. Moving from left to right and top to bottom across the segmented region in each channel, every reporter is located in each channel. In a block 424 a reporter is evaluated for its spectral content and the results are stored. In a decision block 428, the logic determines if more reporters are to be analyzed. If so, the logic loops back to block 424 to repeat the process for each reporter found in the image. Once it is determined in decision block 426 that no more reporters are to be analyzed, then in a block 428 the reporter signatures are compared against the reporter legend of FIG. 19 to determine the compound identity.

In a decision block 430, the logic determines if the bead has a valid signature. If the signature is not valid, that occurrence is noted in a block 432. If the signature is valid, the signature is stored in a block 434. A signature is invalid if it is not supported by the reporter legend. The process illustrated in FIG. 18B is repeated for each bead. It should be understood that when such a process is automated and executed by a computing device, the process of analyzing a single bead occurs very rapidly.

Flow Analysis of Libraries for DNA Sequencing, Polymorphism Analysis, and Expression Analysis Given a bead library that comprises a complete set of DNA oligomers of length N, a subset of the library will hybridize to any piece of single stranded target DNA of approximately length N or greater. If the complementarity of the target DNA to a bead is less than N bases, hybridization strength (measured by the melting temperature, $T_m$) will drop. Six reporter colors employed in a binary encoding scheme are sufficient to encode a bead library of oligos up to length sixteen. As discussed above, the choice of oligo length affects the number of beads necessary for a complete library, the number of reporters necessary to encode the library, and the strength of hybridization. Shorter oligos require the smallest bead sets, the fewest reporters, and have the lowest tolerance for hybridization mismatch.

The shortest practical oligo length is approximately a 10-mer. A complete 10-mer library requires approximately one million beads, which can be analyzed in under an hour at a rate of a few hundred beads per second. The $T_m$ of a perfect 10-mer complement is near room temperature, particularly for A/T rich sequences, so just a few base mismatches will likely cause the target DNA to dissociate from a bead at room temperature. Oligos of length 11 through 16 have melting temperatures significantly higher than room temperature and can therefore tolerate more mismatches than oligos of length 10, given the same reaction stringency. For the purposes of the following description, it will be assumed that a bead library of all possible 10-mers is used.

Figure 20:
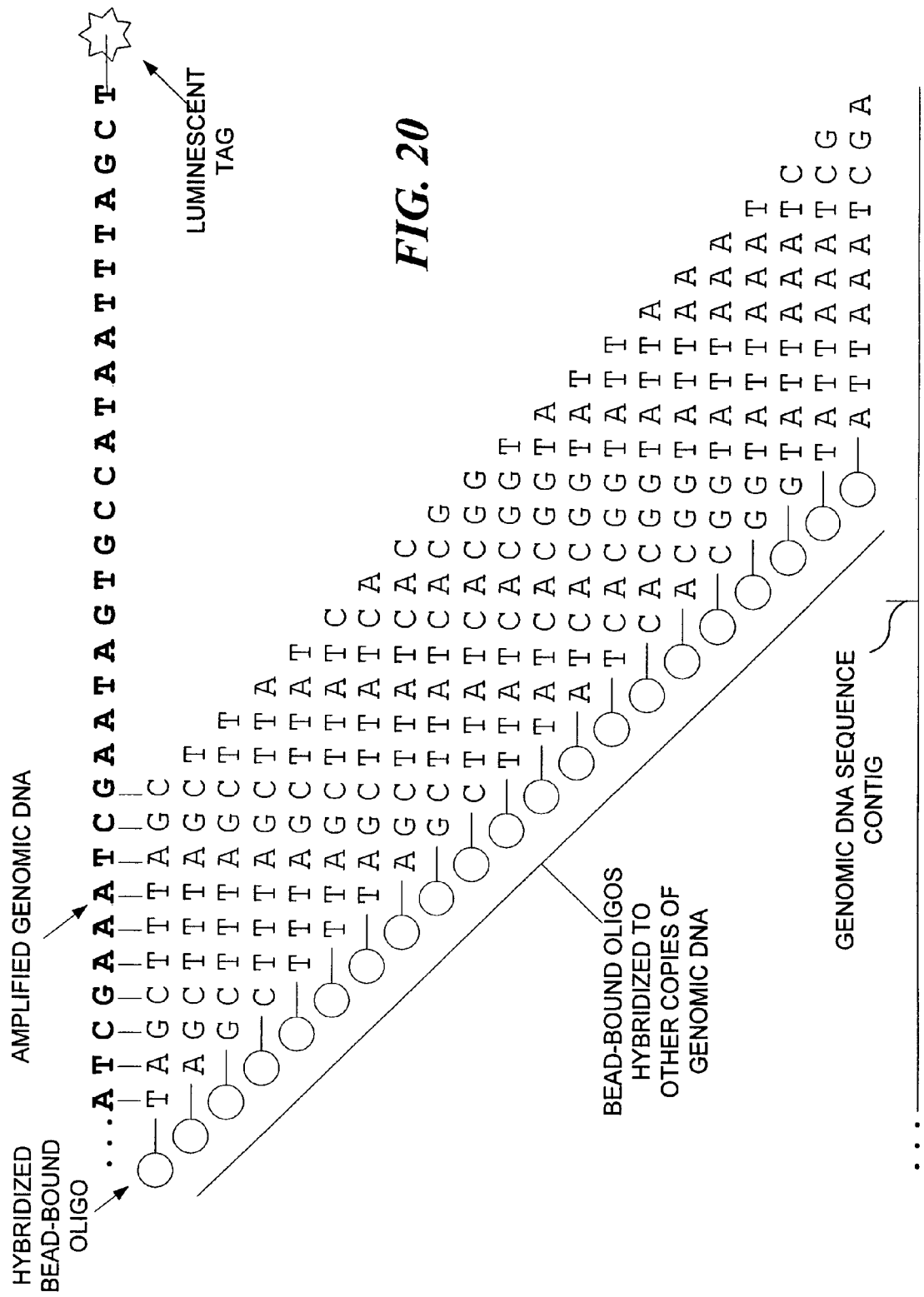
FIG. 20 illustrates hybridizing oligos having sequences that are offset by one nucleotide, forming a contiguous overlapping string of sequences.
Figure 21:
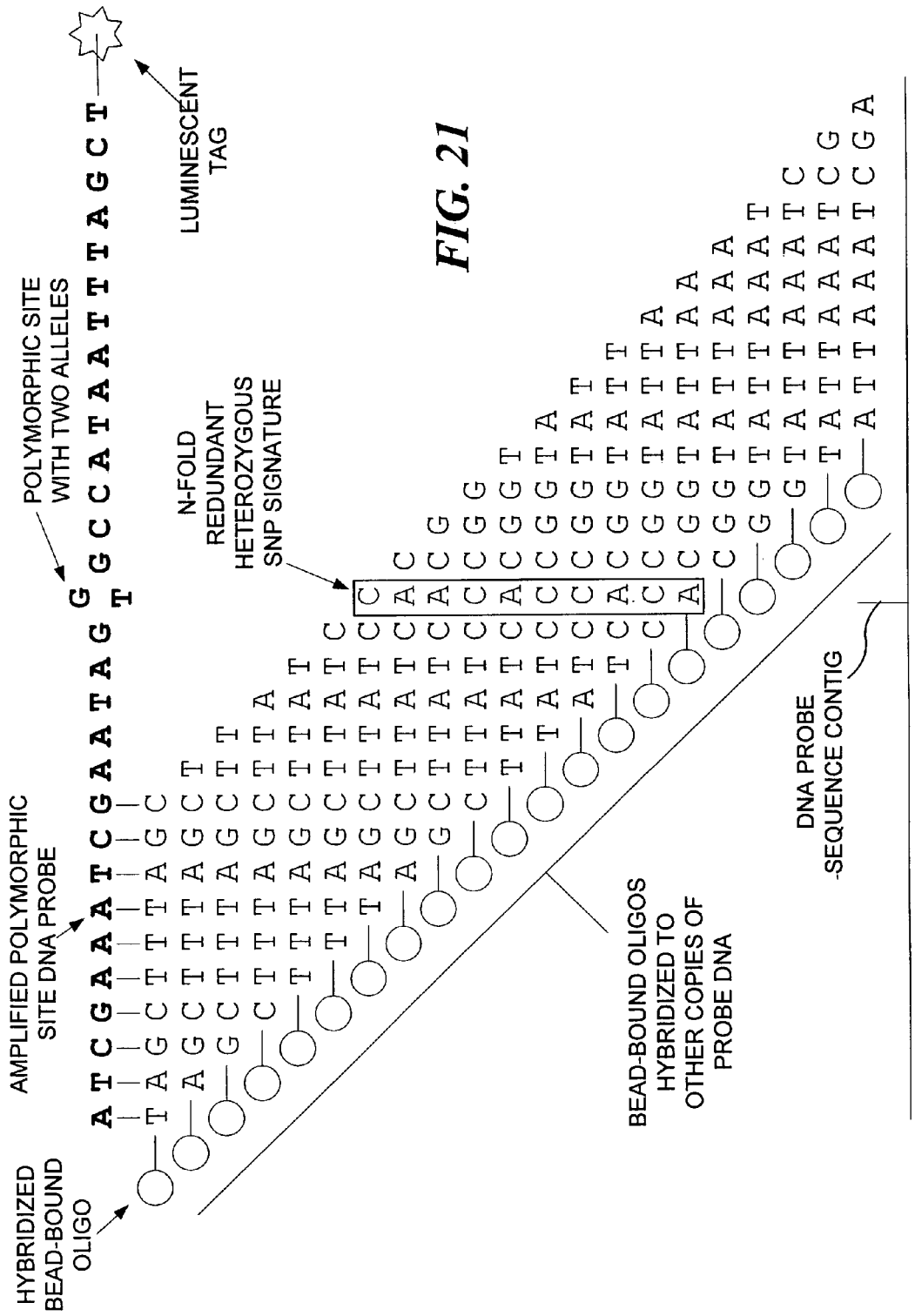
FIG. 21 illustrates the application of the flow imaging sequencing method to determine the identity of SNPs.

If a sample of target DNA consisting of multiple identical copies of length M is hybridized to a complete library, a subset of the beads numbering approximately M-10 will hybridize at random to the different strands of target DNA based on the sequences of their attached oligos. Each of the hybridizing oligos will have sequences that are offset by one nucleotide, forming a contiguous overlapping string of sequences, as shown in FIG. 20. Labeling the target DNA directly or indirectly with at least one luminescent probe will cause the bead to which the DNA is bound to emit light with the characteristic emission spectrum of the probe. If the probe spectrum is distinct from the spectra used for the reporters, the hybridization can be detected as shown in FIG. 21.

After hybridization, the bead library is analyzed by flow imaging and the beads that emit a binding signal are decoded to reveal their associated oligonucleotide sequences. These sequences are then assembled into a "contig" of overlapping sequence by starting with a single oligo sequence and searching the remainder of the set of oligo sequences that bound to the target to find the closest match. The search can be highly constrained by the knowledge that all but a few of the bases near the end of the next oligo to be added to the contig must overlap the end sequence of the contig. The sequencing capacity of a bead library is constrained by the probability that the contig will branch and loop during the sequencing of a single stretch of DNA or that it will cross multiple fragments that are being sequenced simultaneously. The maximum length of a DNA sequence is approximately the square root of the size of the bead library. Hence, a complete 16-mer library of over four billion beads can sequence a stretch of DNA approximately 65,000 bases long.

As illustrated in FIG. 20, the single-base offset of each oligo in the contig assures that there is N-fold sequence redundancy everywhere but at the ends of the contig. Further, the bead library can embody redundancy by including multiple copies of each unique bead (and corresponding oligo).

Having multiple beads of each type enables the system to tolerate some fraction of unanalyzed beads due to system latency, defocus, out-of-view reporters, etc.

The sequencing protocol described herein can be implemented with a single target DNA sample or a pool of multiple targets, which will result in multiple contigs. The target DNA can be from any source, including genomic DNA, viral DNA, DNA produced by an amplification reaction such as a Polymerase Chain Reaction (PCR), or any other source known to those of ordinary skill in the art. In addition, DNA produced by an RNA template, RNA itself, or any other molecule known to hybridize to DNA, such as a peptide nucleic acid, can be used.

Figure 22:
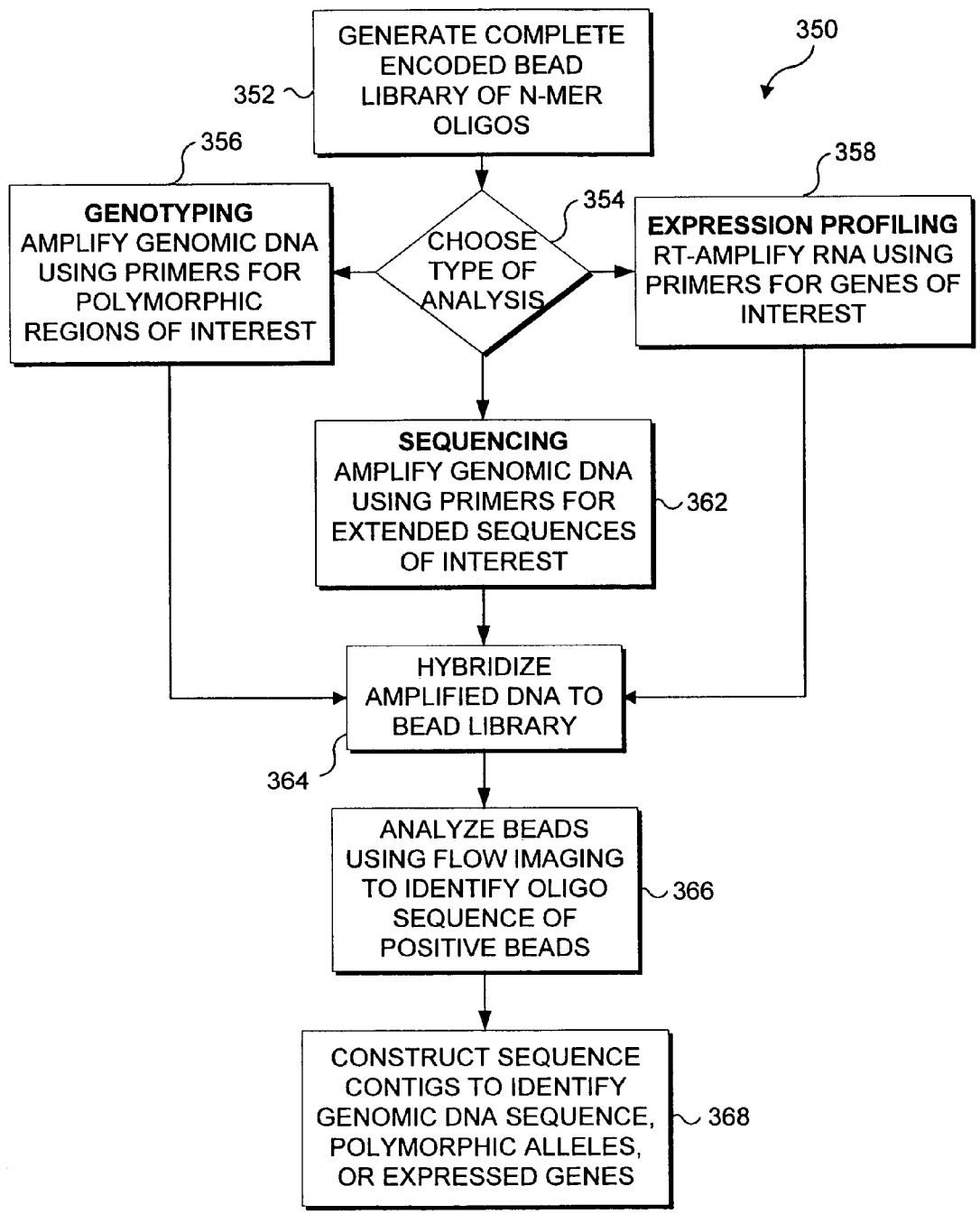
FIG. 22 is a flow chart illustrating the steps employed in the method of the present invention for constructing sequence contigs for identifying a DNA sequence, polymorphic alleles, or expressed genes.

FIG. 21 illustrates the application of the flow imaging sequencing method to determine the identity of SNPs, generally as indicated in the steps of FIG. 22. A target DNA molecule is shown with a polymorphic site that can contain either a G or a T component. In sequencing the target, the ten beads that hybridize across the SNP site will either have a C or an A component at the SNP position if the source DNA is homozygous. If the target DNA is heterozygous, the beads binding across the SNP site will consist of two populations with either a C or an A component at the SNP position. If the DNA used as a template for the amplification of the SNP regions is pooled from numerous sources, the relative frequency in the population of the different polymorphisms at a given SNP position will be reflected in the relative abundance of the amplification products. The relative polymorphism frequency will therefore also be reflected in the binding signal intensity ratios of the different bead sequences that span the SNP site. Numerous polymorphic sites in a large genome can be analyzed simultaneously by amplifying and sequencing short regions from the genome that incorporate the polymorphisms. For example, the 50 nucleotides flanking an SNP require approximately 40-50 distinct beads for analysis. Since this approach is equivalent to DNA sequencing, the library capacity constraints are similar. A million bead library of 10-mers can therefore analyze the relative frequency of a few tens of 50 base SNP fragments. If 12-mers are employed, the library size grows to 16 million, enabling the detailed analysis of roughly 100 SNPs.

An alternative means for analyzing SNPs is to employ polymorphically selective amplification during the production of the target DNA. That is, if a specific polymorphism is present, it will be amplified from the SNP region. Absence of the polymorphism results in no amplification. Because the polymorphic selectivity is inherent in the amplification process, the bead analysis serves only to identify the presence or absence of a reaction product. The presence of a reaction product can be determined by a binding signal on as few as one unique bead associated with the product, which is a far more relaxed constraint on the bead library's analytical capacity than the case of DNA sequencing and greatly increases the analytical capacity. For example, if 50 base stretches of DNA are amplified from multiple SNP sites and pooled for analysis, each SNP fragment must differ from all the others by at least one bead. Hence, there can be extensive cross-branching of the SNP fragment hybridization patterns. The analytical capacity of a library therefore approaches the size of the library divided by the number of beads needed to hybridize to a given SNP fragment. In the case of a million bead 10-mer library with 50 base fragments, on the order of 10,000 SNPs can be analyzed simultaneously.

A variation on the above method of SNP genotyping is to employ a different probe color for each base that may be present at an SNP site. In this manner, relative polymorphism abundance can be obtained without the need to sequence the SNP regions.

In addition to DNA sequencing and polymorphism analysis, flow imaging of bead/oligo libraries can be used to analyze gene expression. In the case of gene expression analysis, specific sequences from each of the genes of interest are extracted from RNA. Extraction can take the form of splicing out and labeling sections of RNA itself or converting the RNA to labeled DNA, for example by reverse transcriptase PCR. The same basic principle of the second method of polymorphism analysis applies to expression analysis, namely that there is no need to sequence the entire expressed gene. Instead, the presence of a specific fragment, as indicated by the binding of at least one unique bead to the amplified expression sequence, indicates the expression of a particular gene. As in sequencing polymorphic sites, the intensity of the binding signal can indicate the level of expression.

The hybridization of DNA to bead-bound oligos is reversible, raising the possibility that a bead library could be used a number of times. There are several ways to restrict the reuse of a bead library based on the fact that the correspondence between each bead signature and its associated oligonucleotide sequence is determined and controlled during the production of a bead lot and can be varied from lot to lot. The information necessary to decode oligo sequences from the bead signatures detected during analysis can be restricted to prevent the unauthorized use of a bead library. The analysis platform could identify the unique lot number of the bead library via a barcode or other identifier and employ a corresponding decoding file distributed by the authorizing body to perform the analysis once, or a given number of times. Another method of restricting authorization might require the user's analytical platform to contact the authorizing entity with the bead lot number at the time of analysis, via the Internet for example, whereupon the identity and validity of the user is determined. Alternately, the beads could be physically altered during analysis, for example by illumination with 260 nm light, to destroy the bound oligonucleotides and prevent reuse.

The use of reporter labeled libraries in flow imaging is not limited to DNA and RNA analysis. Any molecule that can be synthesized on a bead, such as amino acids or drug candidates, can be encoded and read in flow. The concept can even be extended to living cells. Cells of different types can be encoded by attaching labels to their membranes or locating those labels within the cell itself. For example, a reporter with a unique signature identifying a corresponding specific receptor-specific antibody could target any cells expressing that receptor on the cell surface. In some cases, subsequent endocytosis of the receptor-antibody complex would then internalize the reporter bead as well. This binding would identify those cells expressing a specific receptor. Reporters could be internalized by the cell via a variety of mechanisms, including, but not limited to, phagocytosis, endocytosis, lipophilic conjugation, protein transduction, or alternatively through pores created in the cell membrane via exposure to toxins, such as streptolysin O, tetanolysin, *E. coli* hemolysin, via electroporation, or using other means known to one skilled in the art. Specific reporters can be used to indicate cell type, added over time to indicate cell age, and or incorporated upon the cell's exposure to certain drugs or environmental conditions. For encoding even greater diversity of cell types or cell processes, the concept can be extended to tagging cells with reporter labeled carrier assemblies. In this case, the cell acts as a carrier bead which carries other reporter labeled carrier beads. Note also reporter labeled compounds are not limited to multi-component compounds being labeled as there are synthesized. Single component and already synthesized multi component compounds can be bound to beads. Reporters can then be used to label any such compound associated with a bead.

Referring once again to FIG. 22, a flowchart 350 provides the series of logical steps employed to generate and use an encoded bead library for either genotyping, sequencing, or expression profiling. In a block 352, a library of N-mer oligos is generated. The combinatory SAP scheme described above can be beneficially employed, as well as a directed synthesis. While most of the current discussion has been directed to optical reporters that use color as a distinguishing characteristic, it should be noted that other reporters, with other distinguishing characteristics, as noted above, can also be beneficially employed to generate an encoded bead library of the desired size. In a decision block 354, a user must select the type of analysis to be performed (genotyping, sequencing, or expression profiling).

If genotyping is selected, the logic proceeds to a block 356, and the genomic DNA is amplified using primers for polymorphic regions of interest, as discussed above. If in decision block 354, expression profiling was selected as the analysis of choice, then in a block 358, RNA is amplified using primers for genes of interest, also as generally discussed above. Alternatively, if sequencing is selected in decision block 354, then in a block 360, a user would amplify genomic DNA using primer for extended sequences of interest.

Regardless of the analysis selected, the next step is to hybridize the amplified DNA/RNA to the bead library in a block 362. In a block 364, the beads are analyzed, preferably by employing one of the flow imaging systems discussed above, to identify oligo sequences of positive beads. Once the positive beads are imaged, the final step is to construct sequence contigs to identify genomic DNA sequences, polymorphic alleles, or expressed genes, in a block 366.

Although the present invention has been described in connection with the preferred form of practicing it and modifications thereto, those of ordinary skill in the art will understand that many additional modifications can be made to the present invention within the scope of the claims that follow. Accordingly, it is not intended that the scope of the invention in any way be limited by the above description, but instead be determined entirely by reference to the claims that follow.

Flow Analysis of Libraries for Pharmaceutical Chemical Compound Library Analysis Contemporary pharmaceutical research often involves the discovery of novel ligands which bind to specific cell receptors, thereby producing a pharmacologically beneficial response. The ligands might consist of small peptides or other oligomers of a size and molecular weight that are potentially useful as pharmaceutical products. In the present invention, a large library of compounds may be created and attached to reporter labeled beads. This may be accomplished simultaneously as the compounds are synthesized through an SAP process, directed synthesis or binding pre-synthesized compounds to pre-encoded reporter labeled bead assemblies. In the present invention the entire library can then be exposed to numerous sets of receptor targets in an assay in which the targets are fluorescently labeled, undergo a competitive binding assay, or other assay techniques known to those of skill in the art. The exposure can occur in a controlled fashion in a micro-titer plate well or in a micro-fluidic device. Preferably, numerous copies of the compound library can be pipeted into a micro-titer plate well, along with the multiple copies of a target. After sufficient exposure time, the contents of the well can be withdrawn and analyzed (or analyzed in situ), in accordance with the present invention, to determine which compounds demonstrate binding affinity to the target. The process can be repeated for multiple wells containing different targets. Alternatively, if the targets are labeled with distinct fluorochromes, several targets can be interrogated simultaneously in a single well with the compound library. In this case, one of the channels shown in FIG. 17 may serve a dual purpose, containing both small reporter imagery superimposed over a larger image of the carrier bead, thereby indicating the presence of a binding signal.

Flow Analysis of Reporter Encoded Cells

In a fashion similar to that disclosed above, the present invention can be used with cells that are exposed to different compounds, viruses, bacteria or environmental conditions. During or preceding exposure, the cells can be labeled with reporters to encode the exposure history, and or the cell type used in an assay. In accordance with the present invention, this process can be conducted in wells of a micro-titer plate, within a micro-fluidic chip, or on a solid support such as a microscope slide. Once the exposure cycle has been complete the cells can be analyzed to characterize relevant biological affects. FIG. 17 illustrates how these cells would appear when projected onto a detector. In this case elements 346 and 300 represent imagery of the cytoplasm and or nuclei.

Although the present invention has been described in connection with the preferred form of practicing it and modifications thereto, those of ordinary skill in the art will understand that many other modifications can be made thereto. Accordingly, it is not intended that the scope of the present invention in any way be limited by the above description.

The invention in which an exclusive right is claimed is defined by the following:

1. A method for imaging and decoding a plurality of encoded beads comprising the steps of:
   (a) collecting light from an encoded bead along a collection path;
   (b) dispersing the light that is traveling along the collection path into a plurality of light beams, as a function of a plurality of different discriminable characteristics of the light;
   (c) focussing each of the plurality of light beams to produce a respective image corresponding to that light beam, thereby generating a plurality of images, each image being indicative of an identity of said encoded bead;
   (d) detecting the plurality of images using at least one detector;
   (e) analyzing the plurality of images to determine the identity of said encoded bead using a signal processor configured to process output signals from the at least one detector to decode the encoded bead; and
   (f) repeating steps (a)-(e) for successive encoded beads from the plurality of encoded beads.

2. The method of claim 1, wherein the step of dispersing comprises the steps of dividing the light into the plurality of light beams as a function of a wavelength.

3. The method of claim 1, wherein the step of analyzing the plurality of images comprises the steps of generating a plurality of signals, each signal thus generated indicating the presence of a different discriminable characteristic of the light.

4. The method of claim 1, wherein the step of analyzing the plurality of images comprises the step of constructing a sequence library based on each encoded bead that is decoded.

5. The method of claim 1, further comprising the step of illuminating the plurality of encoded beads with light while the encoded beads are moving.

6. The method of claim 1, wherein the step of analyzing the plurality of images comprises the steps of:
   (a) determining dispositions of reporters associated with the bead;
   (b) determining a signature of each reporter associated with the bead based upon the dispositions of the reporters in the plurality of images collected from each encoded bead; and
   (c) decoding each bead as a function of each signature associated with the bead.

7. The method of claim 1, further comprising the step of providing redundant reporters for each encoded bead.

8. The method of claim 1, further comprising the step of disregarding the identity of an encoded bead if the plurality of images for that encoded bead indicate that fewer than a predetermined number of reporters are associated with the encoded bead.

9. The method of claim 1, wherein the step of analyzing comprises the step of referring to an encoded bead legend that identifies each encoded bead as a function of optically discriminable reporters associated with each encoded bead.

10. The method of claim 1, further comprising the step of disregarding the identity of each encoded bead if the analysis of the plurality of images determined that an encoded bead has not experienced a binding event.

11. The method of claim 1, wherein the step of analyzing comprises the step of de-convolving the images if the step of dispersing convolves the plurality of light beams.

12. The method of claim 1, wherein the step of dispersing comprises the step of providing an image corresponding to a binding signal produced by the encoded bead.

13. A method for simultaneously imaging a plurality of reporters disposed on substantially different portions of an encoded bead to identify each unique reporter included on the encoded bead, said method comprising the steps of:
   (a) receiving light from the encoded bead along a plurality of collection paths that are substantially spaced apart using at least one detector, such that light from the reporters disposed on the different portions of the encoded bead affect the light received therefrom; and
   (b) processing the light received from the encoded bead along the plurality of collections paths to identify each unique reporter included on the encoded bead, using a signal processor configured to process output signals from the at least one detector to decode the encoded bead.

14. The method of claim 13, further comprising the step of providing redundant copies of each unique reporter on the encoded bead.

15. The method of claim 13, further comprising the steps of reducing the number of unique reporters necessary to encode a bead; and selecting a library to encode a bead characterized by a length between 9-mer and 16-mer.

16. An imaging system for imaging and decoding a plurality of encoded beads to which is attached one or more compounds, each compound being associated with a unique reporter set, each reporter set including at least one reporter, comprising:
   (a) a collection lens disposed so that light traveling from each encoded bead passes through the collection lens and is focussed along a collection path;
   (b) a dispersing component that receives the light from the collection lens and disperses the light into a plurality of light beams, as a function of a plurality of different discriminable characteristics of the light, said plurality of different discriminable characteristics being indicative of the reporter sets associated with the encoded beads;
   (c) at least one pixilated detector;
   (d) an imaging lens that focuses each of the plurality of light beams on said at least one pixilated detector, producing a respective image corresponding to each of the plurality of light beams, said at least one pixilated detector providing an output signal for each respective image, each output signal indicating the reporter set associated with the encoded bead; and
   (e) a signal processor coupled to receive the output signals from said at least one pixilated detector, said signal processor processing the output signals to decode each reporter set associated with the encoded bead, thereby identifying each compound attached to the encoded bead.

17. The imaging system of claim 16, wherein said signal processor is adapted to generated sequence contigs from a plurality of decoded beads.

18. The imaging system of claim 17, wherein said sequence contigs identify at least one of a genomic DNA sequence, a polymorphic allele, and an expressed gene.

19. The imaging system of claim 16, wherein said signal processor is adapted to analyze said output signals to:
    (a) determine dispositions of the reporters on the encoded bead;
    (b) determine a signature of each reporter associated with the encoded bead based upon the dispositions of the reporters on the bead; and
    (c) determine a reporter set associated with the encoded bead based upon the reporter signatures; and
    (d) identify the each compound associated with the reporter set.

20. The imaging system of claim 16, wherein said signal processor is adapted to disregard all output signals relating to a reporter if signals from an identical reporter have already been analyzed, and to disregard all output signals for an encoded bead if said signals indicate that fewer than a predetermined number of reporters are associated with the encoded bead.

21. The imaging system of claim 16, wherein said signal processor is adapted to employ an encoded bead legend that relates each unique reporter set to a specific compound.

22. The imaging system of claim 21, wherein said signal processor is adapted to disregard all output signals for an encoded bead if it is determined that the encoded bead does not correspond to said encoded bead legend.

23. The imaging system of claim 16, wherein said signal processor is adapted to de-convolve the output signals if said dispersing component convolves the plurality of light beams.

24. The imaging system of claim 16, wherein said dispersing component provides one respective image corresponding to a binding signal produced by the encoded bead.

25. The imaging system of claim 24, wherein said signal processor is adapted to disregard all output signals for an encoded bead if said one respective image indicates that an encoded bead has not experienced a binding event.

26. The imaging system of claim 16, wherein said dispersing component comprises one of a dichroic filters and a prism.

27. The imaging system of claim 16, wherein said at least one pixilated detector comprises a time delay integration (TDI) detector.

28. The imaging system of claim 16, wherein said imaging lens focuses each one of said plurality of light beams onto a different region of said at least one pixilated detector.

* * * * *

UNITED STATES PATENT AND TRADEMARK OFFICE
CERTIFICATE OF CORRECTION

PATENT NO. : 7,567,695 B2
APPLICATION NO. : 11/078009
DATED : July 28, 2009
INVENTOR(S) : Frost et al.

It is certified that error appears in the above-identified patent and that said Letters Patent is hereby corrected as shown below:

| | |
|---|---|
| Column 5, line 7 | "compounds" should read --compound-- |
| Column 5, line 37 | "steps" should read --step-- |
| Column 6, line 10 | after "plurality" insert --of-- |
| Column 6, line 17 | "beam" should read --beams-- |
| Column 7, line 5 | "steps" should read --step-- |
| Column 11, line 52 | "affect" should read --effect-- |
| Column 11, line 67 | "a," should read --a-- |
| Column 12, line 5 | after "that" insert --the-- |
| Column 12, line 26 | "earlier" should read --later-- |
| Column 17, line 51 | "in" should read --is-- |
| Column 18, line 55 | "32 and 32" should read --32a and 32b-- |
| Column 24, line 13 | "and" should read --in-- |
| Column 27, line 1 | before "known" insert --are-- |
| Column 27, line 40 | after "point" delete "interpolation in a" |
| Column 27, line 58 | "multiplies" should read --multiplied-- |
| Column 29, line 27 | after "means" delete "for" |
| Column 29, line 64 | "flurochromes" should read --fluorochromes-- |
| Column 30, line 18 | "flurochromes" should read --fluorochromes-- |
| Column 31, line 45 | "no" should read --not-- |
| Column 32, line 48 | "sequence" should read --sequences-- |
| Column 35, line 2 | "there" should read --they-- |
| Column 52, line 31 (Claim 13) | "collections" should read --collection-- |
| Column 53, line 17 & 20 (Claim 19) | after "bend;" delete "and"; after "identify" delete "the" |

Signed and Sealed this

Eighth Day of June, 2010

David J. Kappos
*Director of the United States Patent and Trademark Office*